United States Patent
Humphreys et al.

(10) Patent No.: US 9,902,768 B2
(45) Date of Patent: *Feb. 27, 2018

(54) SEQUENCE ASYMMETRIC MODIFIED IGG4 BISPECIFIC ANTIBODIES

(71) Applicant: UCB Pharma S.A., Brussels (BE)

(72) Inventors: David Paul Humphreys, Slough (GB); Shirley Jane Peters, Slough (GB)

(73) Assignee: UCB BIOPHARMA SPRL, Brussels (BE)

(*) Notice: Subject to any disclaimer, the term of this patent is extended or adjusted under 35 U.S.C. 154(b) by 0 days.

This patent is subject to a terminal disclaimer.

(21) Appl. No.: 14/380,310

(22) PCT Filed: Feb. 22, 2013

(86) PCT No.: PCT/EP2013/053615
§ 371 (c)(1),
(2) Date: Aug. 21, 2014

(87) PCT Pub. No.: WO2013/124451
PCT Pub. Date: Aug. 29, 2013

(65) Prior Publication Data
US 2015/0017169 A1    Jan. 15, 2015

(30) Foreign Application Priority Data
Feb. 22, 2012 (GB) .................. 1203071.4

(51) Int. Cl.
*C07K 16/24* (2006.01)
*C07K 16/00* (2006.01)
*C07K 16/46* (2006.01)

(52) U.S. Cl.
CPC .............. *C07K 16/24* (2013.01); *C07K 16/00* (2013.01); *C07K 16/468* (2013.01); *C07K 2317/31* (2013.01); *C07K 2317/51* (2013.01); *C07K 2317/522* (2013.01); *C07K 2317/53* (2013.01); *C07K 2317/55* (2013.01); *C07K 2317/94* (2013.01)

(58) Field of Classification Search
CPC .... C07K 16/24; C07K 16/28; C07K 2317/55; C07K 2317/522; C07K 2317/53; C07K 2317/94; C07K 2317/31; C07K 2317/51
USPC ............... 424/136.1, 133.1; 435/320.1, 328; 530/387.3
See application file for complete search history.

(56) References Cited

U.S. PATENT DOCUMENTS

| | | |
|---|---|---|
| 4,741,900 A | 5/1988 | Alvarez et al. |
| 4,816,397 A | 3/1989 | Boss et al. |
| 5,219,996 A | 6/1993 | Bodmer et al. |
| 5,223,409 A | 6/1993 | Ladner et al. |
| 5,403,484 A | 4/1995 | Ladner et al. |
| 5,427,908 A | 6/1995 | Dower et al. |
| 5,516,637 A | 5/1996 | Huang et al. |
| 5,545,806 A | 8/1996 | Lonberg et al. |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,625,126 A | 4/1997 | Lonberg et al. |
| 5,633,425 A | 5/1997 | Lonberg et al. |
| 5,658,727 A | 8/1997 | Barbus et al. |
| 5,661,016 A | 8/1997 | Lonberg et al. |
| 5,667,425 A | 9/1997 | Pineau et al. |
| 5,677,425 A | 10/1997 | Bodmer et al. |
| 5,698,426 A | 12/1997 | Huse |
| 5,733,743 A | 3/1998 | Johnson et al. |
| 5,750,753 A | 5/1998 | Kimae et al. |
| 5,770,429 A | 6/1998 | Lonberg et al. |
| 5,780,225 A | 7/1998 | Wigler et al. |
| 5,821,047 A | 10/1998 | Garrard et al. |
| 5,969,108 A | 10/1999 | McCafferty et al. |
| 6,331,415 B1 | 12/2001 | Cabilly et al. |
| 2008/0063635 A1 | 3/2008 | Takahashi et al. |
| 2013/0323236 A1* | 12/2013 | Humphreys ..... A61K 39/39591 424/133.1 |
| 2015/0017169 A1 | 1/2015 | Humphreys et al. |
| 2015/0018529 A1* | 1/2015 | Humphreys ........... C07K 16/00 530/387.3 |

FOREIGN PATENT DOCUMENTS

| | | |
|---|---|---|
| EP | 0392745 | 10/1990 |
| EP | 0438474 | 7/1991 |
| EP | 0463151 | 1/1992 |
| EP | 0546073 | 6/1993 |
| EP | 1810979 | 7/2007 |

(Continued)

OTHER PUBLICATIONS

Salfeld (Nature Biotech. 25(12): 1369-1372 (2007)).*
Dall'Acqua (J. Immunol. 177:1129-1138 (2006)).*
Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*

(Continued)

*Primary Examiner* — Lynn A Bristol
(74) *Attorney, Agent, or Firm* — McDonnell Boehnen Hulbert & Berghoff LLP

(57) ABSTRACT

The present disclosure provides an asymmetric mixed antibody comprising two heavy chains or heavy chain fragments each comprising at least a variable region, a hinge region and a CH1 domain, wherein a first heavy chain or fragment thereof is a class IgG4 and has:
a the inter-chain cysteine at position 127, numbered according to the Kabat numbering system, in the CH1 domain is substituted with another amino acid; and
b optionally one or more of the amino acids positioned in the upper hinge region is substituted with cysteine, and
wherein the second heavy chain or fragment thereof is characterized in that part or all of the chain has a different amino acid sequence to said first heavy chain in at least the region outside the variable region (for example the constant region), formulations comprising the same, therapeutic used of both of the above, and processes for preparing the antibodies and formulation.

37 Claims, 36 Drawing Sheets

(56) References Cited

FOREIGN PATENT DOCUMENTS

| | | |
|---|---|---|
| EP | 2194066 | 6/2010 |
| EP | 2 409 990 A1 | 1/2012 |
| WO | WO 8601533 | 3/1986 |
| WO | WO 9002809 | 3/1990 |
| WO | WO 9109967 | 7/1991 |
| WO | WO 9110737 | 7/1991 |
| WO | WO 9201047 | 1/1992 |
| WO | WO 9202551 | 2/1992 |
| WO | WO 9218619 | 10/1992 |
| WO | WO 9306231 | 4/1993 |
| WO | WO 9311236 | 6/1993 |
| WO | WO 9515982 | 6/1995 |
| WO | WO 9520401 | 8/1995 |
| WO | WO 9820734 | 5/1997 |
| WO | WO 9825971 | 6/1997 |
| WO | WO 8900195 | 1/1999 |
| WO | WO 8901476 | 2/1999 |
| WO | WO 9222583 | 5/1999 |
| WO | WO 03031581 | 4/2003 |
| WO | WO 2004/003019 * | 6/2004 |
| WO | WO 2004051268 | 6/2004 |
| WO | WO 05117984 | 12/2005 |
| WO | WO 2008038024 | 4/2007 |
| WO | WO 2007106120 | 9/2007 |
| WO | WO 2004106377 | 12/2007 |
| WO | WO 2008145142 | 12/2007 |
| WO | WO 201063785 | 6/2010 |

OTHER PUBLICATIONS

Song et al. (Biochem Biophys Res Comm 268:390-394 (2000)).*
Ibragimova and Eade (Biophysical Journal, Oct. 1999, vol. 77, pp. 2191-2198).*
Dufner (Trends Biotechnol. 24(11):523-29 (2006)).*
Schuurman et al., "The inter-heavy chain disulfide bonds of IgG4 are in equilibrium with intra-chain disulfide bonds", Molecular Immunology, 2001, 38(1), 1-8.
Bloom et al., "Intrachain disulfide bond in the core hinge region of human IgG4", Protein Science, 1997, 6(2), 407-415.
Aalberse et al., "IgG4 breaking the rules", Immunology, 2002, 105(1), 9-19.
Kolfschoten et al., "Anti-inflmmatory activity of human IgG4 antibodies by dynamic Fab arm exchange", Science, 2007, 317(5844), 1554-1557.
Lu et al., "The Effect of a Point Mutation on the Stability of IgG4 as Monitored by Analytical Ultracentrifugation," Journal of Pharmaceutical Sciences, vol. 97, No. 2, Feb. 2008, pp. 960-969.
Schuurman et al., "Normal human immunoglobulin G4 is bispecific: it has two different antigen-combining sites," Immunology, 1999, 97, pp. 693-698.
Wypych et al., "Human IgG2 Antibodies Display Disulfide-mediated Structural Isoforms," Journal of Biological Chemistry, vol. 283, No. 23, Jun. 6, 2008, pp. 16194-16205.
Lefranc et al., Dev. Comp. Immunol., 39:185-203 (2005).
Chapman, Advanced Drug Delivery Reviews, 54:531-545 (2002).
Dubowchik et al., Pharmacology and Therapeutics, 83-67-123 (1999).
Thorpe et al., Immunol. Rev., 62:119-58 (1982).
Hellstrom et al., Controlled Drug Delivery, pp. 623-53 (1987).
Harris, R.J., Journal of Chromatography, 705:129-134 (1995).
Angal et al., Molecular Immunology, 30:105-108 (1993).
Verma et al., Journal of Immunological Methods, 216:165-181 (1998).
Mountain et al., Biotechnol. Genet. Eng. Rev., 10:1-142 (1992).
Bird et al., Science, 242:423-426 (1988).
Riechmann et al., Nature, 332:323-327 (1988).
Orlandi et al., Proc. Natl. Acad. Sci., 86:3833-3837 (1989).
Burton et al., Advances in Immunology, 57:191-280 (1994).
Persic et al., Gene, 187:9-18 (1997).
Kettleborough et al., Eur. J.Immunol., 24:952-958 (1994).
Brekke et al., Immunologist, 1994, 2:125-130.
Murray et al., Harper's Biochemistry, 23rd Edition, 1993, Chapter 4:24-28.
Silva et al., J. Biol. Chem. 290(9):5462-5469, Feb. 27, 2015.
Kohler et al., Nature, 256:495-497 (1975).
Kozbor et al., Immunology Today, 4:72-79 (1983).
Cole et al., Monoclonal Antibodies and Cancer Therapy, pp. 77-96 (1985).
Babcock et al., Proc. natl. Acad. Sci., 93:7843-7848 (1996).
Brinkman et al., J. Immunol. Methods, 182:41-50 (1995).
Ames et al., J. Immunol. Methods, 184:177-186 (1995).
Restriction Requirement dated Jun. 2, 2015, issued in connection with U.S. Appl. No. 14/380,309, filed Aug. 21, 2004, 7 pages.
Non-Final Office Action dated Nov. 13, 2015, issued in connection with U.S. Appl. No. 14/380,309, filed Aug. 21, 2004, 19 pages.
Final Office Action dated Jun. 14, 2016, issued in connection with U.S. Appl. No. 14/380,309, filed Aug. 21, 2004, 23 pages.
Non-Final Office Action dated Sep. 22, 2016, issued in connection with U.S. Appl. No. 14/380,309, filed Aug. 21, 2004, 25 pages.
Restriction Requirement dated Sep. 16, 2015, issued in connection with U.S. Appl. No. 13/817,961, filed Aug. 16, 2013, 7 pages.
Non-Final Office Action dated May 23, 2016, issued in connection with U.S. Appl. No. 13/817,961, filed Aug. 16, 2013, 17 pages.
Final Office Action dated Nov. 28, 2016, issued in connection with U.S. Appl. No. 13/817,961, filed Aug. 16, 2013, 13 pages.

* cited by examiner

Figure 1a

IgG1 wild type CH1 & hinge

(A) STKGPSVFPLAPSSKSTSGGTAALGCLVKDYFPEPVTVSWNSGALTSGVHTFPAVLQSSGLYSLSSVVTVPSSSLGTQTYICNVNH
KPSNTKVDKKV(E)PKSCDKTHTCPPCPAPELGGP    (SEQ ID NO:1)

IgG4 wild type CH1 & hinge

(A) STKGPSVFPLAPCSRSTSESTAALGCLVKDYFPEPVTVSWNSGALTSGVHTFPAVLQSSGLYSLSSVVTVPSSSLGTKTYTCNVDH
KPSNTKVDKRV(E)SKYGPPCPSCPAPEFLGGP    (SEQ ID NO:2)

Ig wild type kappa constant light chain

TVAAPSVFIFPPSDEQLKSGTASVVCLLNNFYPREAKVQWKVDNALQSGNSQESVTEQDSKDSTYSLSSTLTLSKADYEKHKVYACEVT
HQGLSSPVTKSFNRGEC    (SEQ ID NO:66)

Figure 1b

| Light chain | C_L | | | |
|---|---|---|---|---|
| Human κ | FNRGEC (SEQ ID NO:3) | | | |

| Heavy chain | C_H1 (N-term) | Hinge | | |
|---|---|---|---|---|
| | | UPPER | CORE | LOWER |
| Human IgGγ1 | LAPSSKSTS (SEQ ID NO:4) | EPKSCDKTHT (SEQ ID NO:5) | CPPCP | APELLGGP |
| Human IgGγ2 | LAPCSRSTS (SEQ ID NO:6) | ERK (SEQ ID NO:7) | CCVECPPCP | APPVA GP |
| Human IgGγ3 | LAPCSRSTS (SEQ ID NO:8) | ELKTPLGDTTHT (SEQ ID NO:9) | CPRCP(EPKSCDTPPPCPRCP)₃ | APELLGGP |
| Human IgGγ4 | LAPCSRSTS ↑ C127 (SEQ ID NO:10) | ESKYGPP ↑ G230 (SEQ ID NO:11) | CPSCP ↑ ↑ C239 C242 | APEFLGGP |

| Heavy chain | C_H1 (N-term) | Hinge | C_H1 (C-term) | C_H2 (N-term) |
|---|---|---|---|---|
| Human IgD | IISGCRHPK (SEQ ID NO:67) | (E)SPKAQASSVPTAQPQAEGSLAKATTAPATTRNT (SEQ ID NO:68) | EKNVPLP (SEQ ID NO:70) | (V)IAELPPKVSV (SEQ ID NO:71) |

| Heavy chain | C_H1 (N-term) | | | |
|---|---|---|---|---|
| Human IgM | LVSCENSPS (SEQ ID NO:69) | | | |

Figure 2a

| | CH1 | HINGE | | | | | | | | | | | | | | |
|---|---|---|---|---|---|---|---|---|---|---|---|---|---|---|---|---|
| EU Numbering for IgG1 | 131 | 216 | 217 | 218 | 221 | | | 222 | 223 | 224 | 225 | 226 | 227 | 228 | 229 | 230 |
| Kabat Numbering for IgG1 | 127 | 226 | 227 | 228 | 232 | 233 | 234 | 235 | 236 | 237 | 238 | 239 | 240 | 241 | 242 | 243 |
| IMGT Numbering for IgG1 | 10 | 1 | 2 | 3 | 4 | 5 | 6 | 7 | 8 | 9 | 10 | 11 | 12 | 13 | 14 | 15 |
| IgG1 wt residues | S | E | P | K | S | C | D | K | T | H | T | C | P | P | C | P |
| EU Numbering for IgG4 | 131 | 216 | 217 | 218 | 219 | 220 | 224 | 225 | | | | 226 | 227 | 228 | 229 | 230 |
| Kabat Numbering for IgG4 | 127 | 226 | 227 | 228 | 229 | 230 | 237 | 238 | | | | 239 | 240 | 241 | 242 | 243 |
| IMGT Numbering for IgG4 | 10 | 1 | 2 | 3 | 4 | 5 | 6 | 7 | | | | 8 | 9 | 10 | 11 | 12 |
| IgG4 wt residues | C | E | S | K | Y | G | P | P | - | - | - | C | P | S | C | P |
| Mutations to IgG4 | S | | C or P | C | C or S | C | D or A | K or A | A or T or G | A or H or G | A or T or G | S | | P | S | |

Figure 2b

|  | CH1 | HINGE | | | | | | |
|---|---|---|---|---|---|---|---|---|
| Kabat Numbering | 127 | 226 | 227 | 228 | 229 | 230 | 232 | 233 |
| IMGT Numbering for IgG3 | 10 | 1 | 2 | 3 | 4 | 5 | 6 | 7 |
| IgG3 wt residues | C | E | L | K | T | P | L | G |
| Mutations to IgG3 | S | C | C | C | C | C | C | C |

Figure 2c

|  | CH1 | | | | | CH2 | | |
|---|---|---|---|---|---|---|---|---|
| Kabat numbering for IgM | 127 | 223 | 223A | 223B | 223C | 243G | 243H | 243I |
| IMGT Numbering for IgM | 10 | 121 | 122 | 123 | 124 | 1.5 | 1.4 | 1.3 |
| IgM wt residues | C | V | P | L | P | V | I | A |
| Mutations to IgM | S | C | C | C | C | C | C | C |

Figure 2d

|  | CH1 | Hinge | | | | | | |
|---|---|---|---|---|---|---|---|---|
| Kabat numbering for IgD | 128 | 227 | 228 | 229 | 230 | 231 | 232 | 233 |
| IMGT Numbering for IgD | 11 | 1 | 2 | 3 | 4 | 5 | 6 | 7 |
| IgD wt residues | C | E | S | P | K | A | Q | A |
| Mutations to IgD | S | C | C | C | C | C | C | C |

Figure 3a

| Mutations | G4 | G1 | 1 | 2 | 3 | 4 | 5 | 5P | 6 | 7 | 8 | 9 | 10 | 11 | 12 | 13 | 14 | 15 | 16 |
|---|---|---|---|---|---|---|---|---|---|---|---|---|---|---|---|---|---|---|---|
| C127S |  |  | • |  |  |  |  |  |  |  |  |  |  |  |  |  |  |  |  |
| G230C |  |  |  | • | • | • |  | • | • | • | • | • | • | • |  |  |  | • | • |
| C239S |  |  |  | • |  | • | • |  |  |  |  | • | • | • |  |  | • |  |  |
| S241P |  |  |  |  |  |  |  | • |  |  |  |  |  |  |  |  |  |  |  |
| C242S |  |  |  |  | • | • |  |  |  | • | • | • |  | • |  | • | • |  |  |

Figure 3b

| HC Cys position | G4 | G1 | 1 | 2 | 3 | 4 | 5 | 5P | 6 | 7 | 8 | 9 | 10 | 11 | 12 | 13 | 14 | 15 | 16 |
|---|---|---|---|---|---|---|---|---|---|---|---|---|---|---|---|---|---|---|---|
| 127 | LC |  |  |  |  |  |  |  |  |  |  |  |  |  |  |  |  |  |  |
| 230 |  |  |  |  |  |  |  |  |  |  |  |  |  |  |  |  |  |  |  |
| 230 (G4) |  | LC |  |  |  |  |  |  |  |  |  |  |  |  |  |  |  |  |  |
| 233 (G1) | HC | HC | LC or HC | LC | LC |  | HC | HC | HC | HC | LC | LC | LC | LC | LC | LC | LC | HC or LC | 16 |
| 239 | HC | HC | LC or HC |  |  |  | HC | HC | HC | HC |  | HC | HC | HC | HC |  |  | HC or LC | HC or LC |
| 242 | HC | HC | LC or HC |  |  |  | HC | HC |  |  |  |  |  |  |  |  |  | HC or LC | HC or LC |

Figure 4a

| Mutations to G4 | G4 | G1 | 28 | 29 | 30 | 31 | 32 | 33 | 34 | 35 | 36 | 37 | 38 | 39 | 44 | 45 | 46 | 47 |
|---|---|---|---|---|---|---|---|---|---|---|---|---|---|---|---|---|---|---|
| C127S |   |   | • | • | • | • | • | • | • | • | • | • | • | • | • | • | • | • |
| S227C |   |   |   |   |   |   | • | • | • |   | • | • | • | • |   |   |   |   |
| K228C |   |   |   |   |   |   |   |   |   | • |   |   |   |   |   |   |   |   |
| Y229C |   |   | • | • | • | • |   |   |   |   |   |   |   |   |   |   |   |   |
| G230C |   |   |   | • |   | • |   | • |   | • |   | • |   |   | • | • |   |   |
| P238PAAA |   |   |   |   |   |   |   |   |   |   |   |   |   |   | • | • | • | • |
| C239S |   |   |   |   |   |   |   |   |   |   |   |   |   |   |   | • | • | • |
| S241P |   |   |   |   |   |   |   |   |   |   |   |   |   |   |   |   |   |   |
| C242S |   |   |   |   | • | • | • |   | • | • |   |   | • | • | • | • | • | • |

ANTIBODIES

Figure 4b

| HC Cys positi on | G4 | G1 | 28 | 29 | 30 | 31 | 32 | 33 | 34 | 35 | 36 | 37 | 38 | 39 | 44 | 45 | 46 | 47 |
|---|---|---|---|---|---|---|---|---|---|---|---|---|---|---|---|---|---|---|
| 127 | LC | | | | | | | | | | | | | | | | | |
| 227 | | | | | | | | | | | LC or HC | LC | LC | LC | | | | |
| 228 | | | LC or HC | | | | LC or HC | LC | LC | LC | | | | | | | | |
| 229 (G4) | | LC | | LC | LC | LC | | | | | | | | | | | | |
| 230 (G4) | | | HC or LC | | | | HC or LC | | HC | | | | | | LC or HC | LC | LC | LC |
| 233 (G1) | | | HC or LC | | | | HC or LC | | | | HC or LC | HC | HC | | | | | |
| 239 | HC | HC | | HC | HC | | | HC | | | HC or LC | | | | HC or LC | HC | HC | |
| 242 | HC | HC | | | | | | | | | | | | | HC or LC | | | |

FIG. 5A (Ab 6) (SEQ ID NO:12)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV(E) SKYCPPSPSCPAPEFLGGP (Ab 7) (SEQ ID NO:13)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV(E) SKYCPPCPSSPAPEFLGGP (Ab 8) (SEQ ID NO:14)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV(E) SKYCPPSPSSPAPEFLGGP (Ab 15) (SEQ ID NO:15)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV(E) SKYCPPCPSCPAPEFLGGP (Ab 16) (SEQ ID NO:16)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV(E) SKYCPPCPPCPAPEFLGGP (Ab 28) (SEQ ID NO:17)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV(E) SKCGPPCPSCPAPEFLGGP (Ab 29) (SEQ ID NO:18)
(A) STKGPSVFPLAPSSRSTSESTAALGCLVKDYFPEPVTVSWNSGALTSGVHTFPAVLQSSGLYSLSSVVTVPSSSLGTKTYTCNVDH KPSNTKVDKRV(E) SKCGPPSPSCPAPEFLGGP

FIG. 5B (Ab 30) (SEQ ID NO:19)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E) SKCGPPCPSSPAPEFLGGP (Ab 31) (SEQ ID NO:20)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E) SKCGPPSPSSPAPEFLGGP (Ab 32) (SEQ ID NO:21)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E) SCYGPPCPSCPAPEFLGGP (Ab 33) (SEQ ID NO:22)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E) SCYGPPSPSCPAPEFLGGP (Ab 34) (SEQ ID NO:23)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E) SCYGPPCPSSPAPEFLGGP (Ab 35) (SEQ ID NO:24)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E) SCYGPPSPSSPAPEFLGGP (Ab 36) (SEQ ID NO:25)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E) CKYGPPCPSCPAPEFLGGP (Ab 37) (SEQ ID NO:26)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E) CKYGPPSPSCPAPEFLGGP

FIG. 5C

(Ab 38) (SEQ ID NO:27)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E) CKYGPPCPSSPAPEFLGGP

(Ab 39) (SEQ ID NO:28)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E) CKYGPPSPSSPAPEFLGGP

(Ab 44) (SEQ ID NO:29)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E) SKYCPPAAACPSCPAPEFLGGP

(Ab 45) (SEQ ID NO:30)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E) SKYCPPAAASPSCPAPEFLGGP

(Ab 46) (SEQ ID NO:31)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E) SKYCPPAAACPSSPAPEFLGGP

(Ab 47) (SEQ ID NO:32)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E) SKYCPPAAASPSSPAPEFLGGP

(Ab 2) (SEQ ID NO:33)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E) SKYGPSPSCPAPEFLGGP

(Ab 3) (SEQ ID NO:34)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E) SKYGPPCPSSPAPEFLGGP

FIG. 5D (Ab 48) (SEQ ID NO:35)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV (E) PKSCDKTHTCPPCPAPEFLGGP (Ab 28P) (SEQ ID NO:36)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV (E) SKCGPPCPPCPAPEFLGGP (Ab 44P) (SEQ ID NO:37)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV (E) SKYCPPAAACPPCPAPEFLGGP (Ab 1) (SEQ ID NO:296)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV (E) SKYGPPCPSSPAPEFLGGP (Ab 4) (SEQ ID NO:297)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV (E) SKYGPPSPSSPAPEFLGGP

Ab5 (SEQ ID NO:298)
(A) STKGPSVFPLAPCSRSTSESTAALGCLVKDYFPEPVTVSWNSGALTSGVHTFPAVLQSSGLYSLSSVVTVPSSSLGTKTYTCNVDH
KPSNTKVDKRV (E) SKYCPPCPSCPAPEFLGGP

Ab5P (SEQ ID NO:299)
(A) STKGPSVFPLAPCSRSTSESTAALGCLVKDYFPEPVTVSWNSGALTSGVHTFPAVLQSSGLYSLSSVVTVPSSSLGTKTYTCNVDH
KPSNTKVDKRV (E) SKYCPPCPPCPAPEFLGGP

Ab9 (SEQ ID NO:300)
(A) STKGPSVFPLAPCSRSTSESTAALGCLVKDYFPEPVTVSWNSGALTSGVHTFPAVLQSSGLYSLSSVVTVPSSSLGTKTYTCNVDH
KPSNTKVDKRV (E) SKYCPPSPSCPAPEFLGGP

FIG. 5E

Ab10 (SEQ ID NO:301)
(A) STKGPSVFPLAPCSRSTSESTAALGCLVKDYFPEPVTVSWNSGALTSGVHTFPAVLQSSGLYSLSSVVTVPSSSLGTKTYTCNVDH
KPSNTKVDKRV(E) SKYCPPCPSSPAPEFLGGP

Ab11 (SEQ ID NO:302)
(A) STKGPSVFPLAPCSRSTSESTAALGCLVKDYFPEPVTVSWNSGALTSGVHTFPAVLQSSGLYSLSSVVTVPSSSLGTKTYTCNVDH
KPSNTKVDKRV(E) SKYCPPSPSSPAPEFLGGP

Ab12 (SEQ ID NO:303)
(A) STKGPSVFPLAPCSRSTSESTAALGCLVKDYFPEPVTVSWNSGALTSGVHTFPAVLQSSGLYSLSSVVTVPSSSLGTKTYTCNVDH
KPSNTKVDKRV(E) SKYGPPSPSCPAPEFLGGP

Ab13 (SEQ ID NO:304)
(A) STKGPSVFPLAPCSRSTSESTAALGCLVKDYFPEPVTVSWNSGALTSGVHTFPAVLQSSGLYSLSSVVTVPSSSLGTKTYTCNVDH
KPSNTKVDKRV(E) SKYGPPCPSSPAPEFLGGP

Ab14 (SEQ ID NO:305)
(A) STKGPSVFPLAPCSRSTSESTAALGCLVKDYFPEPVTVSWNSGALTSGVHTFPAVLQSSGLYSLSSVVTVPSSSLGTKTYTCNVDH
KPSNTKVDKRV(E) SKYGPPSPSSPAPEFLGGP

FIG. 6A

IgG4 CH2 and CH3: (SEQ ID NO:64)
SVFLFPPKPKDTLMISRTPEVTCVVVDVSQEDPEVQFNWYVDGVEVHNAKTKPREEQFNSTYRVVSVLTVLHQDWLNGKEYKCKVSNKG
LPSSIEKTISKAKGQPREPQVYTLPPSQEEMTKNQVSLTCLVKGFYPSDIAVEWESNGQPENNYKTTPPVLDSDGSFFLYSRLTVDKSR
WQEGNVFSCSVMHEALHNHYTQKSLSLSLGK IgG4 CH2 IgG1 CH3: (SEQ ID NO:65)
SVFLFPPKPKDTLMISRTPEVTCVVVDVSQEDPEVQFNWYVDGVEVHNAKTKPREEQFNSTYRVVSVLTVLHQDWLNGKEYKCKVSNKG
LPSSIEKTISKAKGQPREPQVYTLPPSRDELTKNQVSLTCLVKGFYPSDIAVEWESNGQPENNYKTTPPVLDSDGSFFLYSKLTVDKSR
WQQGNVFSCSVMHEALHNHYTQKSLSLSPGK (Ab 6) (SEQ ID NO:38)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E) SKYCPPSPSCPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK (Ab 7) (SEQ ID NO:39)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E) SKYCPPCPSPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK (Ab 8) (SEQ ID NO:40)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E) SKYCPPSPSPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK

FIG. 6B

(Ab 15) (SEQ ID NO:41)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E) S<u>K</u>YCPPPCSCPAPEFLGGPSVFLFPPKPKDTLMISRTPEVTCVVVDVSQEDPEVQFNWYVDGVEVHNAKTKPREE
QFNSTYRVVSVLTVLH<u>Q</u>D<u>W</u>LNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK

(Ab 16) (SEQ ID NO:42)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E) S<u>K</u>YCPPPC<u>P</u>CPAPEFLGGPSVFLFPPKPKDTLMISRTPEVTCVVVDVSQEDPEVQFNWYVDGVEVHNAKTKPREE
QFNSTYRVVSVLTVLH<u>Q</u>D<u>W</u>LNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK

(Ab 28) (SEQ ID NO:43)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E) S<u>K</u>CGPPCSCPAPEFLGGPSVFLFPPKPKDTLMISRTPEVTCVVVDVSQEDPEVQFNWYVDGVEVHNAKTKPREE
QFNSTYRVVSVLTVLH<u>Q</u>D<u>W</u>LNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK

(Ab 29) (SEQ ID NO:44)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E) S<u>K</u>CGPPSPSCPAPEFLGGPSVFLFPPKPKDTLMISRTPEVTCVVVDVSQEDPEVQFNWYVDGVEVHNAKTKPREE
QFNSTYRVVSVLTVLH<u>Q</u>D<u>W</u>LNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK

(Ab 30) (SEQ ID NO:45)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E) S<u>K</u>CGPPCSSPAPEFLGGPSVFLFPPKPKDTLMISRTPEVTCVVVDVSQEDPEVQFNWYVDGVEVHNAKTKPREE
QFNSTYRVVSVLTVLH<u>Q</u>D<u>W</u>LNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK

FIG. 6C (Ab 31) (SEQ ID NO:46)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E)SKCGPPSPSSPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK (Ab 32) (SEQ ID NO:47)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E)SCYGPPCPSCPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK (Ab 33) (SEQ ID NO:48)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E)SCYGPPSPSCPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK (Ab 34) (SEQ ID NO:49)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E)SCYGPPCPSCPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK (Ab 35) (SEQ ID NO:50)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E)SCYGPPSPSCPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK

FIG. 6D (Ab 36) (SEQ ID NO:51)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E) CKYGPPCPSCPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK (Ab 37) (SEQ ID NO:52)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E) CKYGPPSPSCPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK (Ab 38) (SEQ ID NO:53)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E) CKYGPPCPSSPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK (Ab 39) (SEQ ID NO:54)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E) CKYGPPSPSPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK (Ab 44) (SEQ ID NO:55)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E) SKYCPPAAACPSCPAPEFLGGPSVFLFPPKPKDTLMISRTPEVTCVVVDVSQEDPEVQFNWYVDGVEVHNAKTKP
REEQFNSTYRVVSVLTVLHQDWLNGKEYKCKVSNKGLPSSIEKTISKAKGQPREPQVYTLPPSQEEMTKNQVSLTCLVKGFYPSDIAVE
WESNGQPENNYKTTPPVLDSDGSFFLYSRLTVDKSRWQEGNVFSCSVMHEALHNHYTQKSLSLSLGK

FIG. 6E

(Ab 45) (SEQ ID NO:56)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E)SKYCPPAAASPSCPAPEFLGGPSVFLFPPKPKDTLMISRTPEVTCVVVDVSQEDPEVQFNWYVDGVEVHNAKTKP
REEQFNSTYRVVSVLTVLHQDWLNGKEYKCKVSNKGLPSSIEKTISKAKGQPREPQVYTLPPSQEEMTKNQVSLTCLVKGFYPSDIAVE
WESNGQPENNYKTTPPVLDSDGSFFLYSRLTVDKSRWQEGNVFSCSVMHEALHNHYTQKSLSLSLGK

(Ab 46) (SEQ ID NO:57)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E)SKYCPPAAACPSSPAPEFLGGPSVFLFPPKPKDTLMISRTPEVTCVVVDVSQEDPEVQFNWYVDGVEVHNAKTKP
REEQFNSTYRVVSVLTVLHQDWLNGKEYKCKVSNKGLPSSIEKTISKAKGQPREPQVYTLPPSQEEMTKNQVSLTCLVKGFYPSDIAVE
WESNGQPENNYKTTPPVLDSDGSFFLYSRLTVDKSRWQEGNVFSCSVMHEALHNHYTQKSLSLSLGK

(Ab 47) (SEQ ID NO:58)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E)SKYCPPAAASPSSPAPEFLGGPSVFLFPPKPKDTLMISRTPEVTCVVVDVSQEDPEVQFNWYVDGVEVHNAKTKP
REEQFNSTYRVVSVLTVLHQDWLNGKEYKCKVSNKGLPSSIEKTISKAKGQPREPQVYTLPPSQEEMTKNQVSLTCLVKGFYPSDIAVE
WESNGQPENNYKTTPPVLDSDGSFFLYSRLTVDKSRWQEGNVFSCSVMHEALHNHYTQKSLSLSLGK

(Ab 2) (SEQ ID NO:59)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E)SKYGPPSPSCPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK

(Ab 3) (SEQ ID NO:60)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E)SKYGPPCPSSPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK

FIG. 6F

(Ab 48) (SEQ ID NO:61)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E)PKSCDKTHTCPPCPAPEFLGGPSVFLFPPKPKDTLMISRTPEVTCVVVDVSQEDPEVQFNWYVDGVEHNAKTKP
REEQFNSTYRVVSVLTVLHQDWLNGKEYKCKVSNKGLPSSIEKTISKAKGQPREPQVYTLPPSQEEMTKNQVSLTCLVKGFYPSDIAVE
WESNGQPENNYKTTPPVLDSDGSFFLYSRLTVDKSRWQEGNVFSCSVMHEALHNHYTQKSLSLSLGK

(Ab 28P) (SEQ ID NO:62)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E)SKCGPPCPAPEFLGGPSVFLFPPKPKDTLMISRTPEVTCVVVDVSQEDPEVQFNWYVDGVEHNAKTKPREE
QFNSTYRVVSVLTVLHQDWLNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK

(Ab 44P) (SEQ ID NO:63)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E)SKYCPPAAACPPCPAPEFLGGPSVFLFPPKPKDTLMISRTPEVTCVVVDVSQEDPEVQFNWYVDGVEHNAKTKP
REEQFNSTYRVVSVLTVLHQDWLNGKEYKCKVSNKGLPSSIEKTISKAKGQPREPQVYTLPPSQEEMTKNQVSLTCLVKGFYPSDIAVE
WESNGQPENNYKTTPPVLDSDGSFFLYSRLTVDKSRWQEGNVFSCSVMHEALHNHYTQKSLSLSLGK

(Ab 1) (SEQ ID NO:306)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E)SKYGPPCPSCPAPEFLGGPSVFLFPPKPKDTLMISRTPEVTCVVVDVSQEDPEVQFNWYVDGVEHNAKTKPREE
QFNSTYRVVSVLTVLHQDWLNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK

(Ab 4) (SEQ ID NO:307)
(A) STKGPSVFPLAPSSRSTSESTAALGCLVKDYFPEPVTVSWNSGALTSGVHTFPAVLQSSGLYSLSSVVTVPSSSLGTKTYTCNVDH
KPSNTKVDKRV(E)SKYGPPSPSSPAPEFLGGPSVFLFPPKPKDTLMISRTPEVTCVVVDVSQEDPEVQFNWYVDGVEHNAKTKPREE
QFNSTYRVVSVLTVLHQDWLNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK

FIG. 6G

Ab5 (SEQ ID NO:308)
(A) STKGPSVFPLAPCSRSTSESTAALGCLVKDYFPEPVTVSWNSGALTSGVHTFPAVLQSSGLYSLSSVVTVPSSSLGTKTYTCNVDH
KPSNTKVDKRV(E)SKYCPPCPSCPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK

Ab5P (SEQ ID NO:309)
(A) STKGPSVFPLAPCSRSTSESTAALGCLVKDYFPEPVTVSWNSGALTSGVHTFPAVLQSSGLYSLSSVVTVPSSSLGTKTYTCNVDH
KPSNTKVDKRV(E)SKYCPPCPCPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK

Ab9 (SEQ ID NO:310)
(A) STKGPSVFPLAPCSRSTSESTAALGCLVKDYFPEPVTVSWNSGALTSGVHTFPAVLQSSGLYSLSSVVTVPSSSLGTKTYTCNVDH
KPSNTKVDKRV(E)SKYCPPSPSCPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK

Ab10 (SEQ ID NO:311)
(A) STKGPSVFPLAPCSRSTSESTAALGCLVKDYFPEPVTVSWNSGALTSGVHTFPAVLQSSGLYSLSSVVTVPSSSLGTKTYTCNVDH
KPSNTKVDKRV(E)SKYCPPSPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK

Ab11 (SEQ ID NO:312)
(A) STKGPSVFPLAPCSRSTSESTAALGCLVKDYFPEPVTVSWNSGALTSGVHTFPAVLQSSGLYSLSSVVTVPSSSLGTKTYTCNVDH
KPSNTKVDKRV(E)SKYCPPSPSPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK

FIG. 6H

Ab12 (SEQ ID NO:313)
(A) STKGPSVFPLAPCSRSTSESTAALGCLVKDYFPEPVTVSWNSGALTSGVHTFPAVLQSSGLYSLSSVVTVPSSSLGTKTYTCNVDH
KPSNTKVDKRV(E) SKYGPPSPSCPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK

Ab13 (SEQ ID NO:314)
(A) STKGPSVFPLAPCSRSTSESTAALGCLVKDYFPEPVTVSWNSGALTSGVHTFPAVLQSSGLYSLSSVVTVPSSSLGTKTYTCNVDH
KPSNTKVDKRV(E) SKYGPPCPSSPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK

Ab14 (SEQ ID NO:315)
(A) STKGPSVFPLAPCSRSTSESTAALGCLVKDYFPEPVTVSWNSGALTSGVHTFPAVLQSSGLYSLSSVVTVPSSSLGTKTYTCNVDH
KPSNTKVDKRV(E) SKYGPPSPSSPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYTQKSLSLSLGK

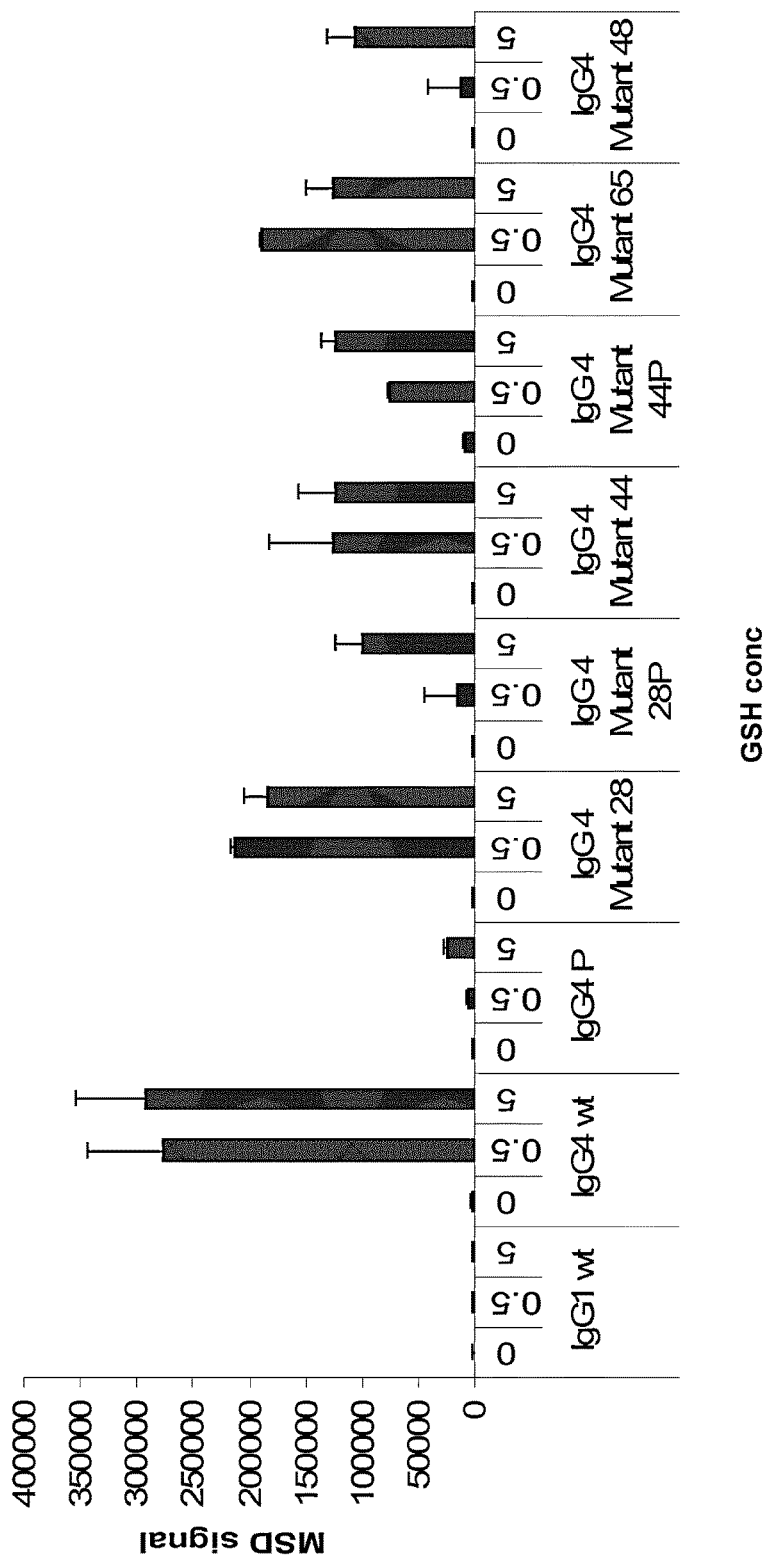
FIGURE 16 Heavy Chain Exchange at 16 hours for IgG1 Wild-Type, IgG4 Wild-Type and Various Mutants at Two Concentrations of GSH

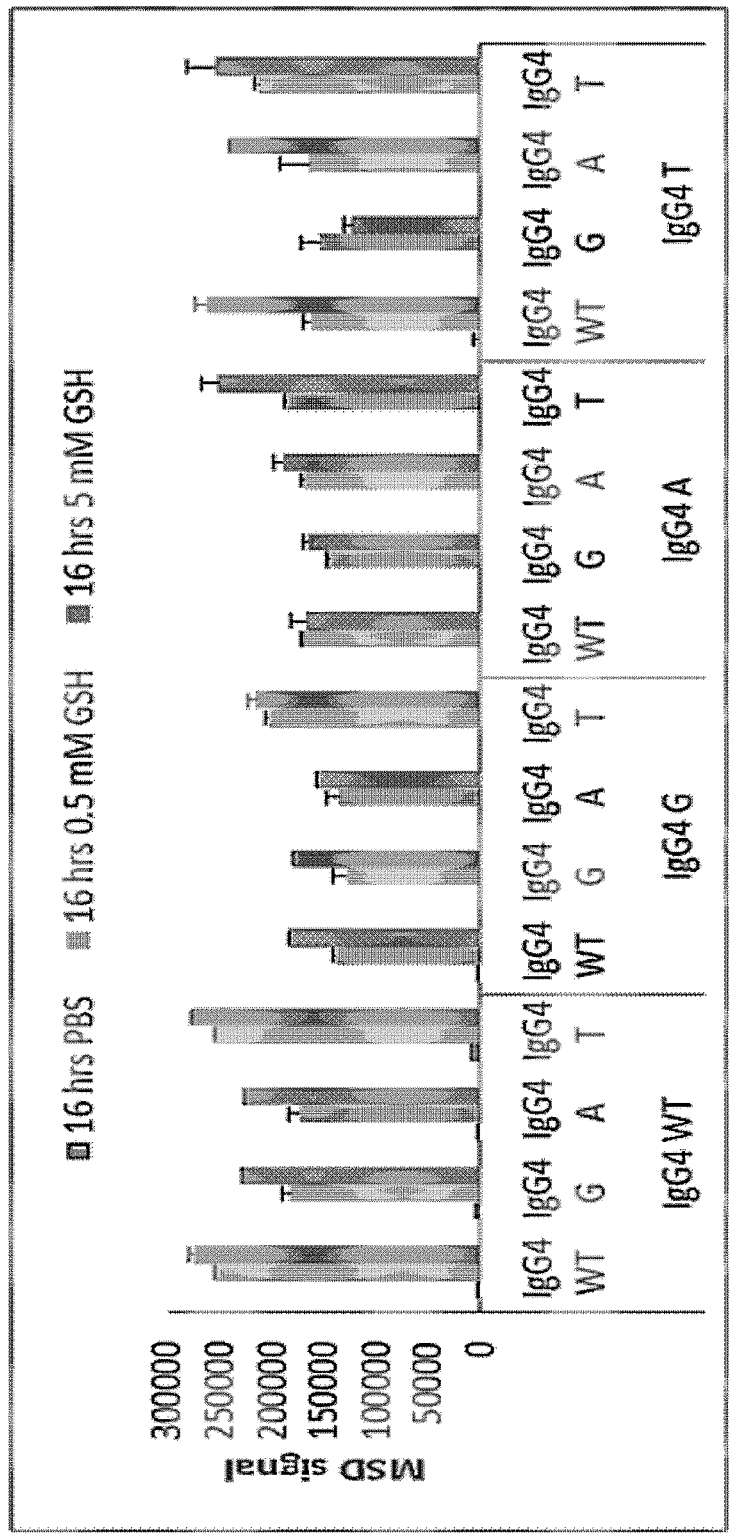
FIGURE 17  Asymmetric exchange analysis of mutants comprising type 1 variable regions with alternative residues at position 241 with type 2 variable regions.

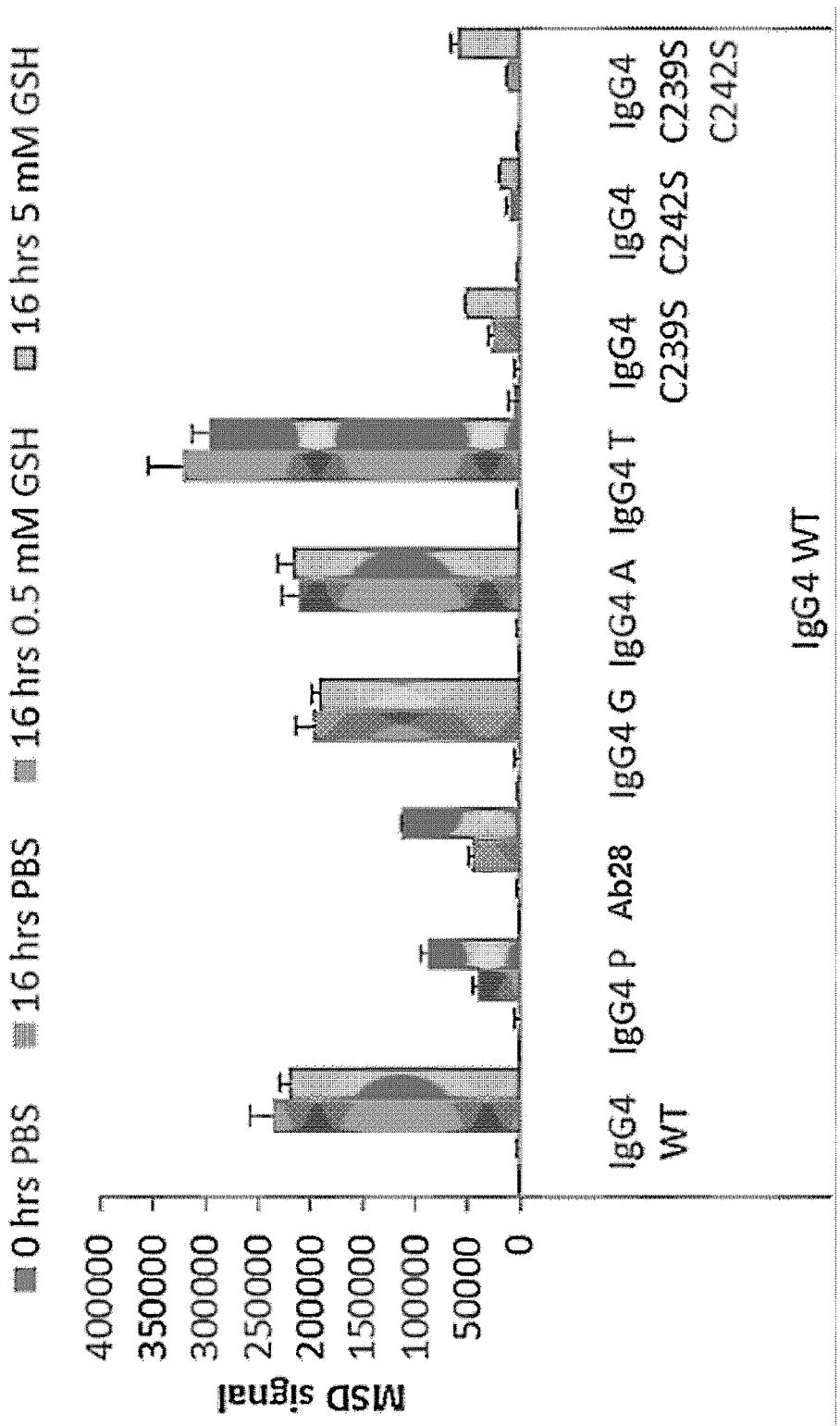
FIGURE 18 Asymetric exchange analysis of IgG4 WT with type 1 variable regions incubated with different S241 and core hinge cysteine mutants with type 2 variable regions.

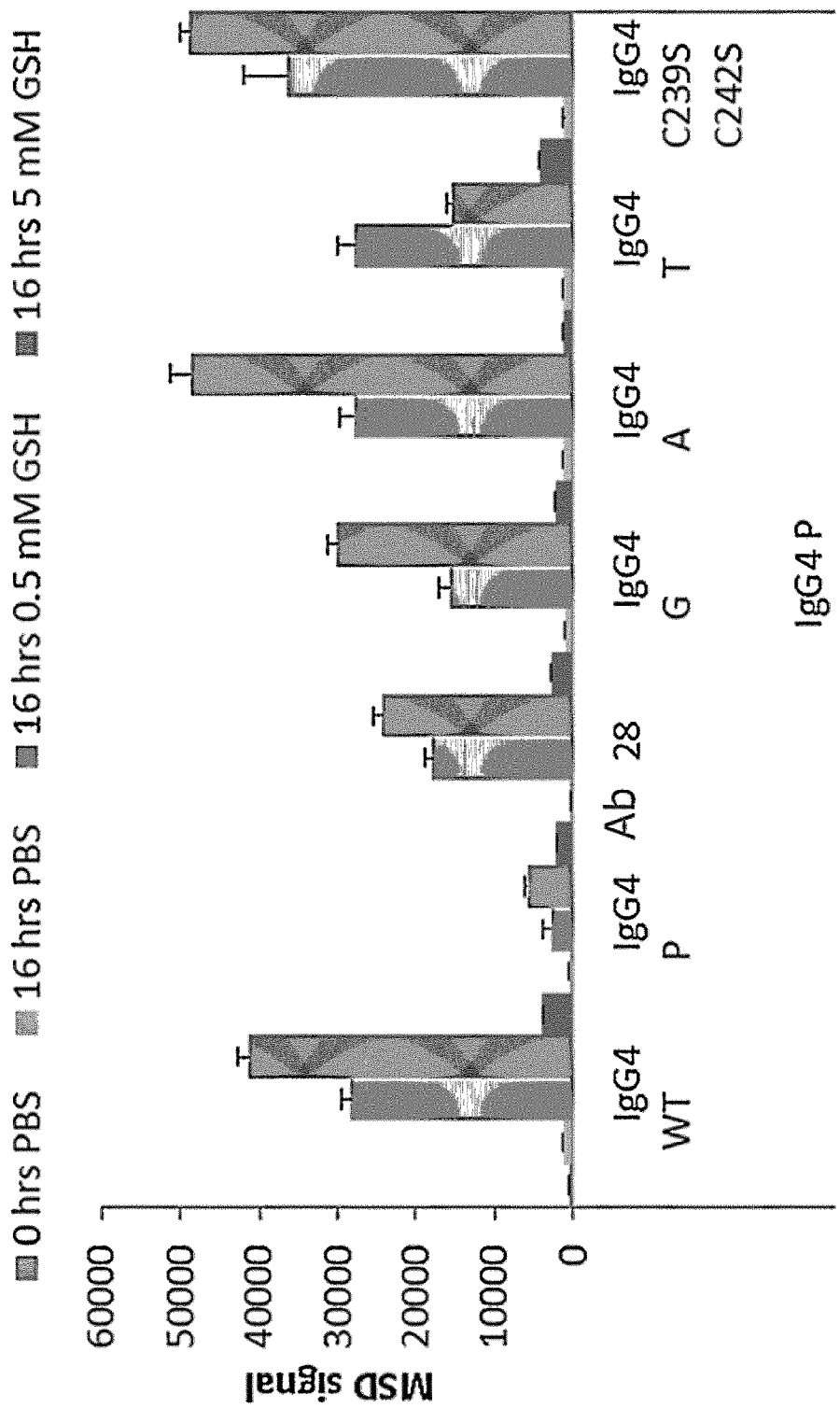
FIGURE 19 Asymetric exchange analysis of IgG4 S241P with type 1 variable regions incubated with different S241 mutants, IgG4 C127S Y229C (Ab 28) with type 2 variable regions.

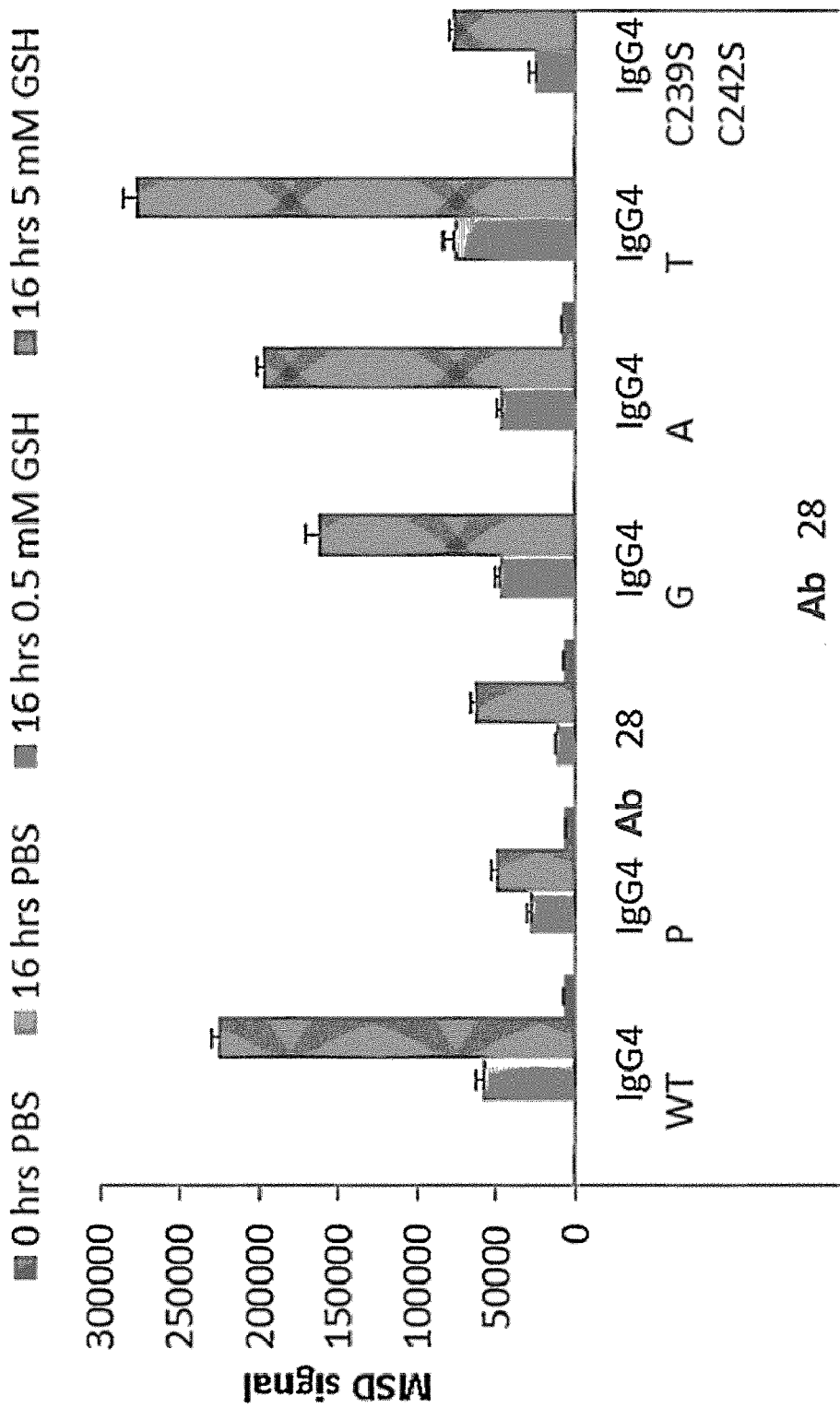
FIGURE 20  Asymetric exchange analysis of IgG4 C127S Y229C (number 28) with type 1 variable regions incubated with different S241 mutants and IgG4 WT with type 2 variable regions

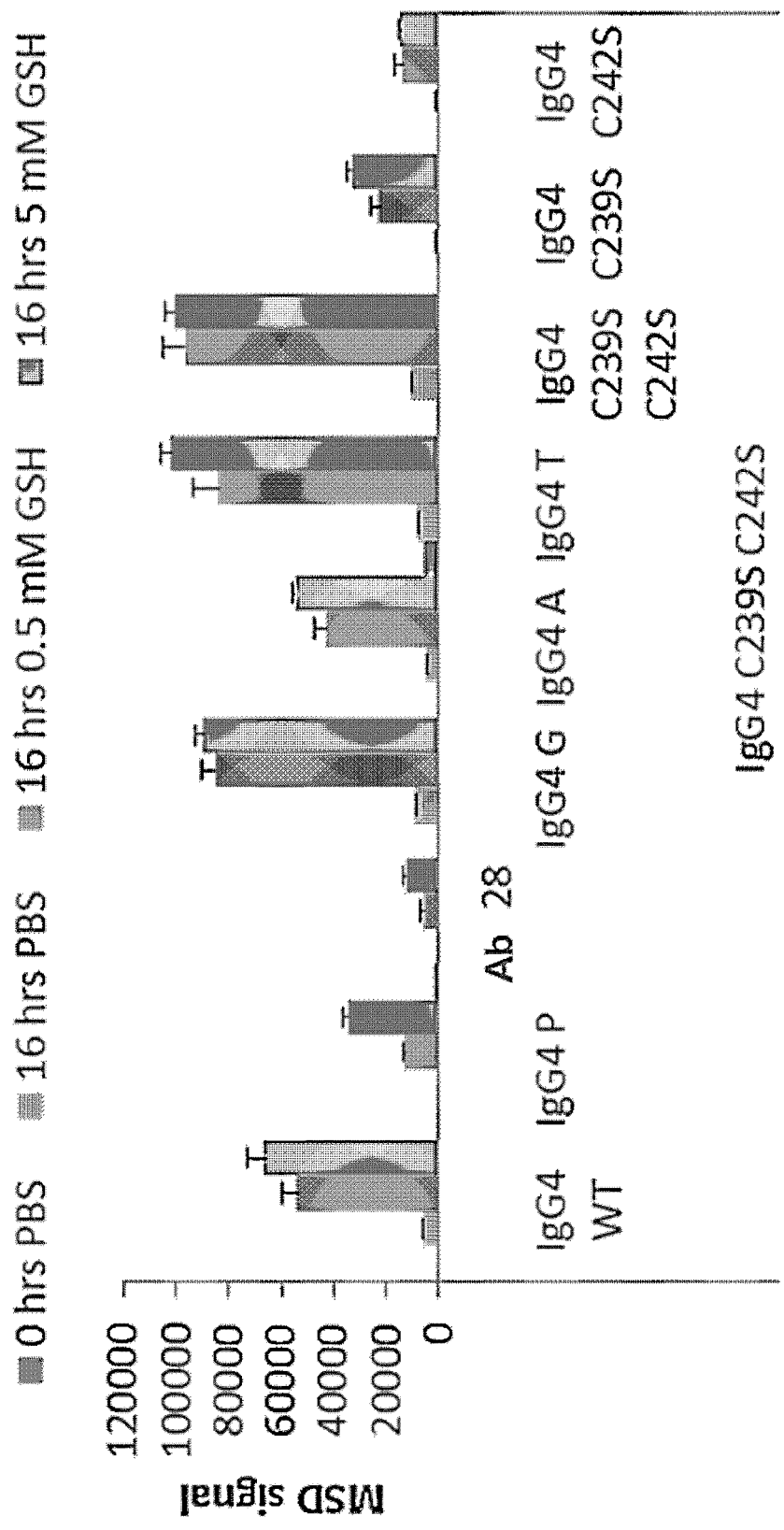
FIGURE 21 Asymetric exchange analysis of a double hinge mutants with type 1 variable regions incubated with multiple mutants with type 2 variable regions.

SEQUENCE ASYMMETRIC MODIFIED IGG4 BISPECIFIC ANTIBODIES

CROSS REFERENCE TO RELATED APPLICATIONS

This application is a US national phase of International Application No. PCT/EP2013/053615 filed on Feb. 22, 2013, which claims priority to Great Britain Patent Application No. 1203071.4 filed on Feb. 22, 2012 the disclosures of each of which are explicitly incorporated by reference in their entirety herein.

The present disclosure relates to asymmetric antibodies comprising an IgG4 heavy chain or fragment which is mutated and a second heavy chain or fragment which is distinct from said IgG4 chain. The disclosure also extends to compositions comprising said asymmetric antibodies and use of the antibodies and compositions comprising same for treatment. In a further aspect the disclosure extends to methods of preparing the antibodies and formulations, and vectors encoding the antibodies and hosts expressing same.

The biopharmaceutical industry encompassing recombinant proteins, monoclonal antibodies (mAbs) and nucleic acid-based drugs is growing rapidly. Antibody engineering has resulted in the design and production of antibody fragments or alternative formats. Preferred molecular format along with other aspects such as production yield, protein quality and storage stability are taken into consideration when selecting an antibody-based protein as a therapeutic agent.

The basic structure of all immunoglobulin (Ig) molecules comprises two identical heavy chains (HCs) and two identical light chains (LCs) which are coupled by disulphide bonds. Each LC consists of a variable ($V_L$) and constant domain ($C_L$). Based on the HC, five main Ig classes are recognized: IgG, IgA, IgD, IgE and IgM. For IgG, the HC consists of one variable domain ($V_H$) and three constant domains ($C_H1$-3). The $C_H2$ and $C_H3$ domains form the Fc part of the molecule that is responsible for stimulating effector function and is linked to the Fab fragment ($V_H V_L$ and $C_H C_L$) by a hinge region which confers flexibility to the IgG molecule. Two antigen recognition sites are located at the ends of the $V_L$ and $V_H$ domains. IgG is further subdivided into 4 different isotypes: IgG1, IgG2, IgG3 and IgG4.

Fc-mediated effector functions i.e. antibody dependent cytotoxicity (ADCC) or complement dependent cytotoxicity (CDC) are isotype dependent. Each isotype has evolved to perform a specific function within the body. The IgG1 isotype is currently the most widely used as a therapeutic due to its extended half-life, enhanced ADCC activation and complement activation. Other isotypes are employed as therapeutic agents depending on the target and desired effect. For instance, when target antigens are simply to be neutralized and effector functions are less important, alternative isotypes such as IgG2 and IgG4 can be used. Alternatively, IgG with re-engineered Fc/effector function may be considered.

IgG2 also has minimal associated effector function but is prone to dimerisation which is not fully understood.

IgG4 remains a useful isotype because of its relative lack of effector function induction. However, use of IgG4 also has some inherent practical difficulties namely its shorter serum half-life and its ability to undergo "Fab-arm exchange" (also referred to as dynamic heavy chain exchange or heavy chain exchange), wherein the heavy chain and its attached light chain of one antibody is exchanged with the heavy chain and its attached light chain of another antibody to form a whole antibody composed of two heavy chains and two attached light chains (van der Neut Kolfschoten et al., 2007 Science 317, 1554-1557).

In vivo, Fab-arm exchange results in bispecific antibodies that, due to their different variable domains, can co-engage distinct target antigens. This produces a large percentage of circulating IgG4 which have been observed to be bispecific, but functionally monovalent. (Schuurman, J., Van Ree, R., Perdok, G. J., Van Doorn, H. R., Tan, K. Y., Aalberse, R. C., 1999. Normal human immunoglobulin G4 can be bispecific: it has two different antigen-combining sites. Immunology 97, 693-698).

In vitro, when IgG4 antibodies are analysed by non-reducing SDS-PAGE, they have been observed to form so called 'half-molecules' each comprising a single covalently associated heavy-light chain pair caused by the absence of inter heavy chain disulphide bonds typically due to the formation of intra heavy chain disulphide bonds within the hinge region of one heavy chain. The heavy chain of a "half-molecule" may non-covalently associate with its heavy chain paired partner, the association being maintained by $C_H3:C_H3$ domain interactions. In solution such 'half-molecules' are actually observed using methods such as size exclusion chromatography to be full sized, that is approximately 150 kDa but on non-reducing SDS-PAGE are comprised of 75 kDa LC:HC pairings (so-called "half-molecule").

A Ser to Pro mutation at position 241 (numbered according to the Kabat numbering system) in the hinge reduces the appearance of these 'half molecules' by non-reducing, SDS-PAGE (Angal, S. et al., 1993. A single amino acid substitution abolishes the heterogeneity of chimeric mouse/human (IgG4) antibody as observed during SDS-PAGE analysis Mol Immunol 30, 105-108). In addition, this point mutation does not influence the compact structure of IgG4 thereby allowing IgG4 to retain its reduced ability to activate complement.

Following the discovery of the S241P mutation, further mutations to IgG4 have been investigated in order to understand the inter-heavy chain interaction in IgG4 antibodies, reduce IgG4 effector function and enhance structural stability. In Schuurman et al. (Schuurman, J et al., 2001. The inter-heavy chain disulphide bonds of IgG4 are in equilibrium with intra-heavy chain disulphide bonds. Molecular Immunology 38, 1-8), the observed instability of inter-heavy chain disulphide bonds of IgG4 was investigated using IgG4 mutants. In mutant M1 Cys 131 (numbered according to EU numbering system or Cys 127 according to Kabat numbering system), which is involved in the inter-heavy-light chain ($C_L$-$C_{H1}$) disulphide bond, was replaced by serine and it was found that this mutant resulted in the formation of dimers of light chains and dimers of heavy chains. In mutant M2 cysteine 226 (226 numbered according to EU numbering system or 239 according to Kabat numbering system), which is involved in an inter-heavy chain disulphide bond in the hinge, was replaced by serine and it was found that this mutant had a more stable inter-heavy chain linkage compared to IgG4 and prevents the formation of an intra-heavy chain disulphide bond.

The alteration of the number of cysteine residues present in the hinge region of antibodies has been previously investigated. U.S. Pat. No. 5,677,425 Bodmer et al. discloses that the number of cysteine residues in the hinge region may be increased in order to facilitate the use of the cysteine thiol groups for attaching effector or reporter molecules. U.S. Pat. No. 5,677,425 also teaches that the number of cysteine residues in the hinge region may be reduced to one in order to facilitate the assembly of the antibody molecules, since it will only be necessary to form a single disulphide bond, which will provide a specific target for attaching the hinge region either to another hinge region or to an effector or reporter molecule.

Given that IgG4 antibodies administered to a subject are susceptible to dynamic heavy chain exchange to form "mixed antibodies" this process can exploited in the present disclosure to prepare in vitro the antibodies of the present disclosure. Advantageously, this allows the characteristics of the antibodies to be manipulated.

There is still a need to provide new antibodies for use as a therapeutic. The present invention provides new mutant antibodies which may have advantageous properties including improved biophysical properties, for example compared to wild-type antibodies.

SUMMARY OF THE INVENTION

The present disclosure provides an asymmetric mixed antibody comprising two heavy chains or heavy chain fragments each comprising at least a variable region, a hinge region and a $C_H1$ domain, wherein a first heavy chain or fragment thereof is a class IgG 4 and has:
  a) the inter-chain cysteine at position 127, numbered according to the Kabat numbering system, in the $C_H1$ domain is substituted with another amino acid; and
  b) optionally one or more of the amino acids positioned in the upper hinge region is substituted with cysteine.
wherein the second heavy chain or fragment thereof is characterised in that part of all of the chain has a different amino acid sequence to said first heavy chain in at least the region outside the variable region.

In an alternative aspect the present disclosure relates to an asymmetric mixed antibody comprised of an IgG4 heavy chain or heavy chain fragment wherein the heavy chain or fragment comprises a variable region, a hinge region and a $C_H1$ domain wherein the hinge is mutated to be an IgG1 type hinge.

There is also provided an asymmetric mixed antibody comprising a first and second heavy chain or heavy chain fragments each comprising at least a variable region, a hinge region and a $C_H1$ domain wherein the first heavy chain or fragment thereof is a class IgG4 and has an IgG1 type hinge and the second heavy chain or fragment thereof has a different amino acid sequence to said first heavy chain in at least the region outside the variable region.

In one embodiment the hinge sequence of the two heavy chains is similar or identical.

The present disclosure is advantageous because it allows manipulation and control of the antibody properties by methods that are convenient and readily accessible.

The antibodies of the present invention may demonstrate reduced heavy chain exchange compared to wild-type IgG4, which provides an asymmetric (such as a bispecific antibody) which demonstrates little or no exchange with wild-type IgG4 in vivo due to its reduced propensity to exchange compared to IgG4 and also due to the relatively low concentration of an asymmetric mixed antibody in vivo compared to natural circulating IgG4 antibodies.

The antibodies of the present invention may demonstrate reduced heavy change exchange at concentrations greater than in vivo concentrations, for example concentrations of 0.5 mM or greater compared to IgG4 wild type. Whilst the antibodies of the invention demonstrate reduced heavy chain exchange compared to wild type IgG4, they do demonstrate a degree of heavy chain exchange, compared to IgG1 wt and IgG4 S241P, which is sufficient to create an asymmetric mixed (such as a bispecific antibody) from two different antibodies (such as two antibodies having different antigen specificities) in vitro.

Thus in one embodiment antibodies of the present disclosure can be exchange in vitro with 5 mM GSH but not with 0.5 mM GSH. The latter more closely mimics in vivo exchange barrier. FIG. 20 illustrates this in that Ab28 (C127S Y229C) does exchange with WT, S241G S241A or S241T at 5 mM GSH, but not at 0.5 mM.

Accordingly, the present invention also provides a method of generating an asymmetric mixed antibody, comprising the steps of taking a symmetrical antibody comprising a first heavy chain sequence or a fragment thereof as defined herein and mixing the said antibody in vitro with a second symmetrical antibody comprising a second heavy chain sequence or a fragment thereof which is different to said first heavy chain sequence, under conditions conducive to heavy chain exchange between the two antibodies, and optionally isolation of the asymmetric mixed antibody obtained therefrom. In one embodiment the method provides a bispecific antibody, which comprises mixing two antibodies, wherein the antigen specificity of variable regions in the first antibody is different to the antigen specificity of the variable regions in the second antibody.

In one embodiment the antibodies are monovalent.

The method of the present disclosure allows the properties to the antibody to be completely manipulated to provide final therapeutic molecule that is customized and optimized for the intended therapeutic use.

In addition the antibodies according the present disclosure may be advantageous in that they have low levels of effector function and/or do not participate in cross-linking.

BRIEF DESCRIPTION OF THE FIGURES

FIG. 1a shows the human $C_H1$ and hinge sequences of IgG1 wild type and IgG4 wild type, wherein the hinge residues are underlined, and the kappa light chain constant sequence.

FIG. 1b shows:
  the human kappa light chain constant sequence indicating the cysteine (underlined) that forms the inter-chain $C_L$-$C_H1$ disulphide bond;
  the human IgG 1, 2, 3 and 4 heavy chain N-terminal $C_H1$ residues and hinge region sequences wherein the cysteine position (in upper hinge for IgG1 and in N-terminal $C_H1$ for IgG 2, 3 and 4) is indicated (underlined) which forms the inter-chain $C_L$-$C_H1$ disulphide bond;
  the human IgD heavy chain N-terminal $C_H1$ residues and part of the hinge region sequences wherein the cysteine position in the N-terminal $C_H1$ sequence is indicated (underlined) which forms the inter-chain $C_L$-$C_H1$ disulphide bond;
  the human IgM heavy chain N-terminal $C_H1$, C-terminal $C_H1$ residues and selected N-terminal $C_H2$ residues wherein the cysteine position in the N-terminal $C_H1$ is indicated (underlined) which forms the inter-chain $C_L$-$C_H1$ disulphide bond; and
  the residues in the upper hinge of IgG3 and IgG4, the hinge of IgD and in the C-terminal $C_H1$ and the $C_H2$ of IgM where underlined residues indicate positions where one or more residues may be substituted with cysteine in the antibodies of the present invention.

FIG. 2a shows the $C_H1$ cysteine residue (C127) which forms the inter-chain disulphide bond with a cysteine in the light chain and the upper and core hinge residues of IgG1 wild type, IgG4 wild type and the positions where mutations have been introduced in the IgG4 antibodies of the present invention.

FIG. 2b shows the $C_H1$ cysteine residue (C127) which forms the inter-chain disulphide bond with a cysteine in the light chain and the hinge residues of IgG3 wild type and the positions where one or more residues are substituted with cysteine in the IgG3 antibodies of the present invention.

FIG. 2c shows the $C_H1$ cysteine residue (C127) which forms the inter-chain disulphide bond with a cysteine in the light chain and selected $C_H1$ and $C_H2$ residues of IgM wild type and the positions where one or more residues are substituted with cysteine in the IgM antibodies of the present invention.

FIG. 2d shows the $C_H1$ cysteine residue (C128) which forms the inter-chain disulphide bond with a cysteine in the light chain and the hinge residues of IgD wild type and the positions where one or more residues are substituted with cysteine in the IgD antibodies of the present invention.

FIG. 3a shows the mutations introduced in IgG4 antibodies according to the present invention.

FIG. 3b shows the positions of the residues in the mutated heavy chain of the IgG4 antibodies shown in FIG. 3a and the predicted disulphide bond that can form with a cysteine in either the light chain (LC) or with another mutated heavy chain (HC). Where the cysteine may bond with a cysteine in the LC or HC, the underlined chain is the predicted predominant disulphide bond arrangement.

FIG. 4a shows the mutations introduced in IgG4 antibodies according to the present invention.

FIG. 4b shows the positions of the cysteine residues in the IgG4 antibodies shown in FIG. 4a and predicted disulphide bond that can form with a cysteine in either the light chain (LC) or heavy chain (HC). Where the cysteine may bond with a cysteine in the LC or HC, the underlined chain is the predicted predominant disulphide bond arrangement.

FIGS. 5A-5E show various sequences

FIGS. 6A-6H show various sequences

Figure 7:
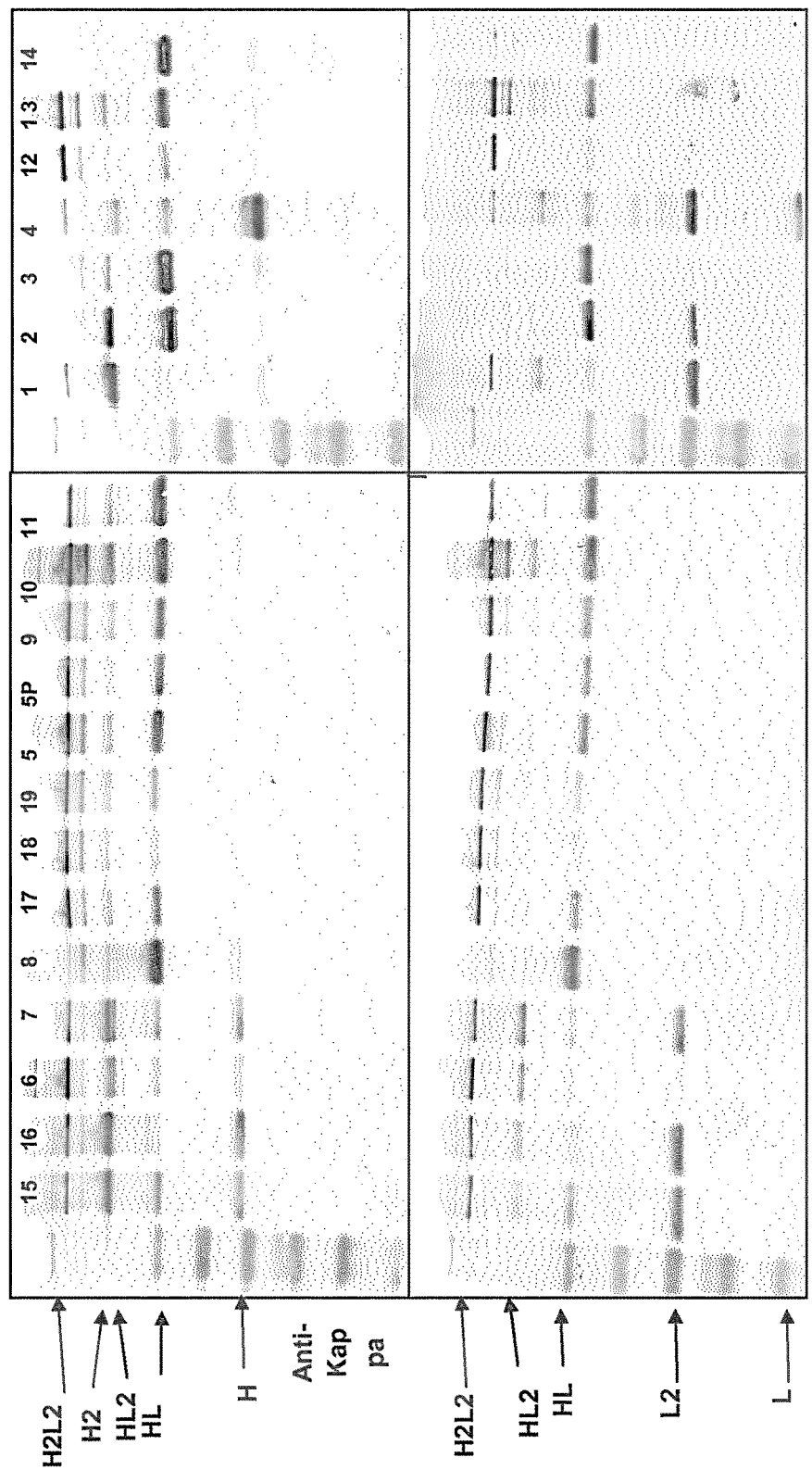

FIG. 7 shows the Western Blot analysis of antibodies according to the present invention with the top gel showing the results using an Anti-human Fc Antibody and the bottom gel showing the results using an Anti-Kappa Antibody.

Figure 8:
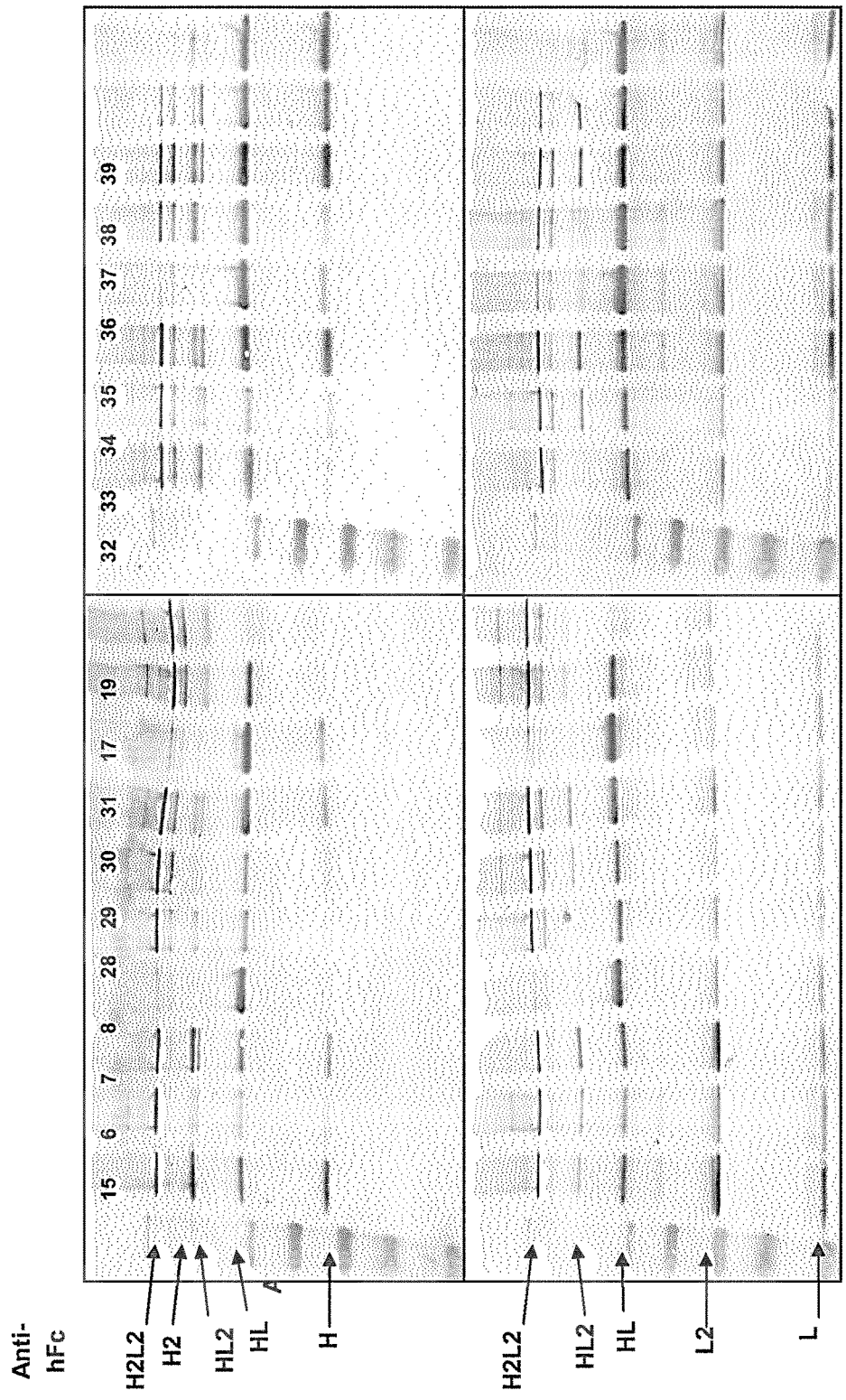

FIG. 8 shows the Western Blot analysis of antibodies according to the present invention with the top gel showing the results using an Anti-human Fc Antibody and the bottom gel showing the results using an Anti-human Kappa Antibody.

Figure 9:
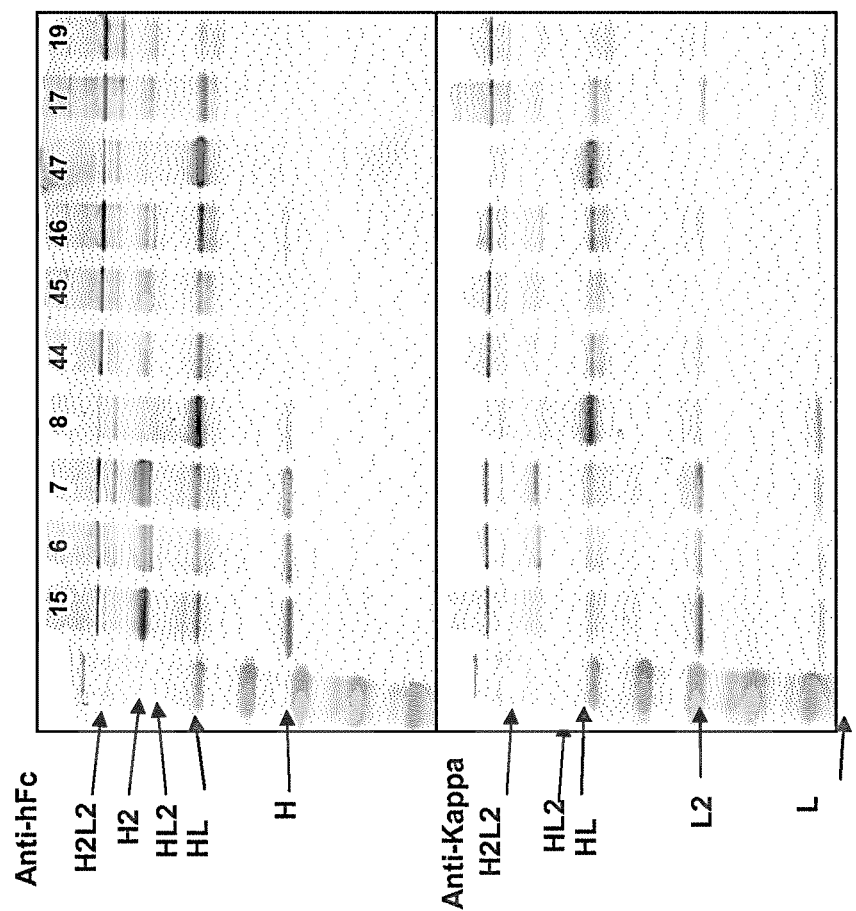

FIG. 9 shows the Western Blot analysis of antibodies according to the present invention with the top gel showing the results using an Anti-human Fc Antibody and the bottom gel showing the results using an Anti-human Kappa Antibody.

Figure 10:
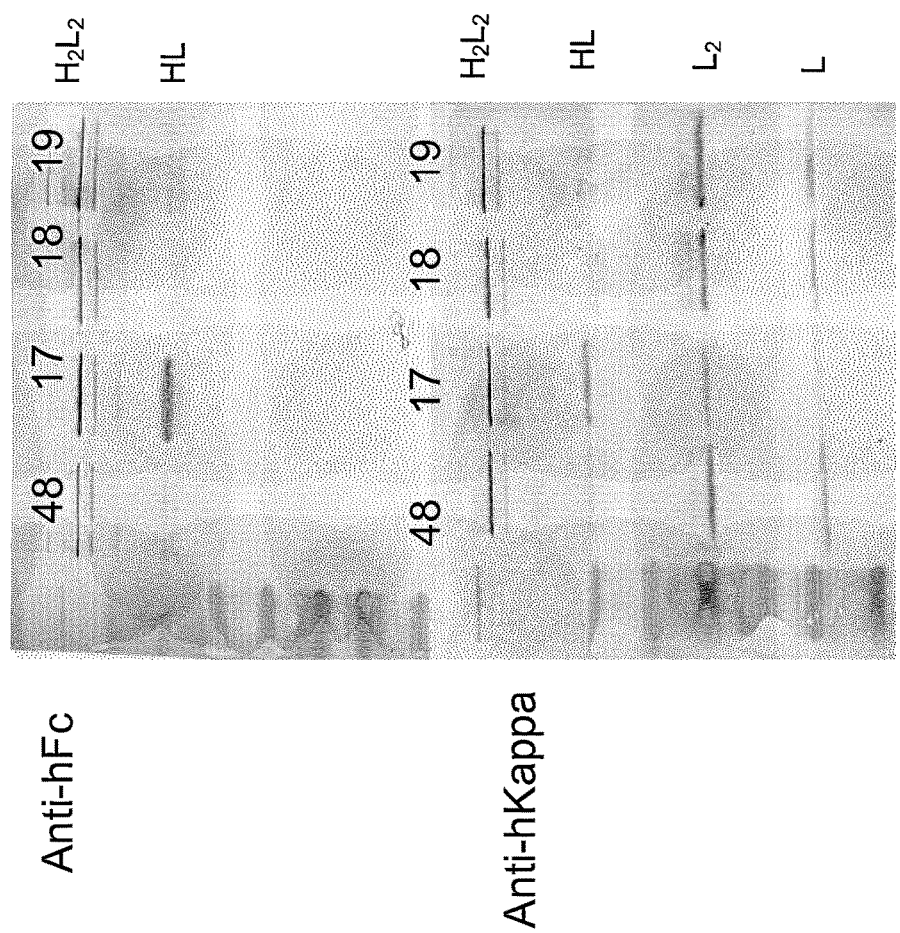

FIG. 10 shows the Western Blot analysis of an antibody according to the present invention with the top gel showing the results using an Anti-human Fc Antibody and the bottom gel showing the results using an Anti-human Kappa Antibody.

Figure 11:
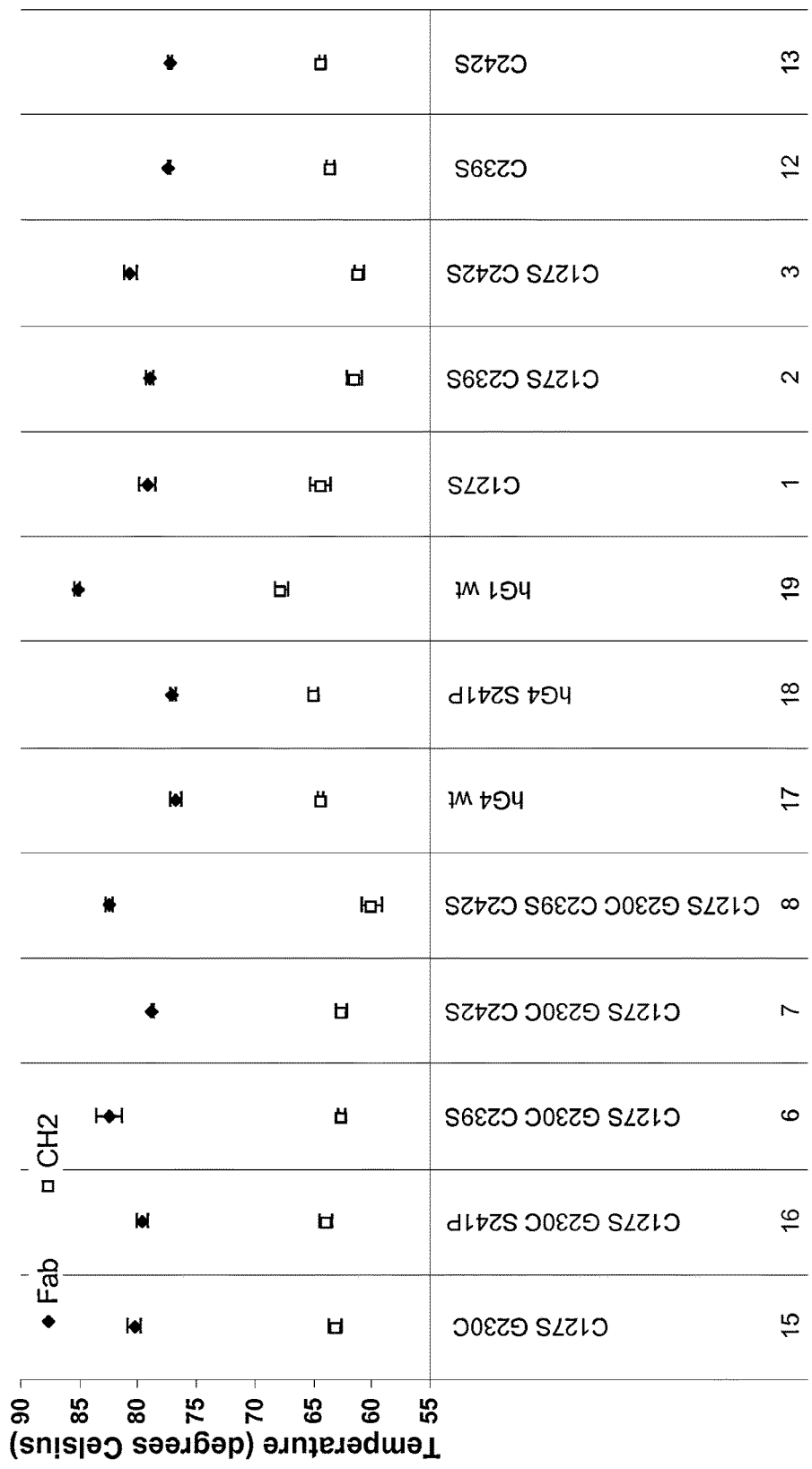

FIG. 11 shows the results of a Thermofluor analysis of antibodies of the present invention which shows the Fab and $C_H2$ domain thermostabilties.

Figure 12:
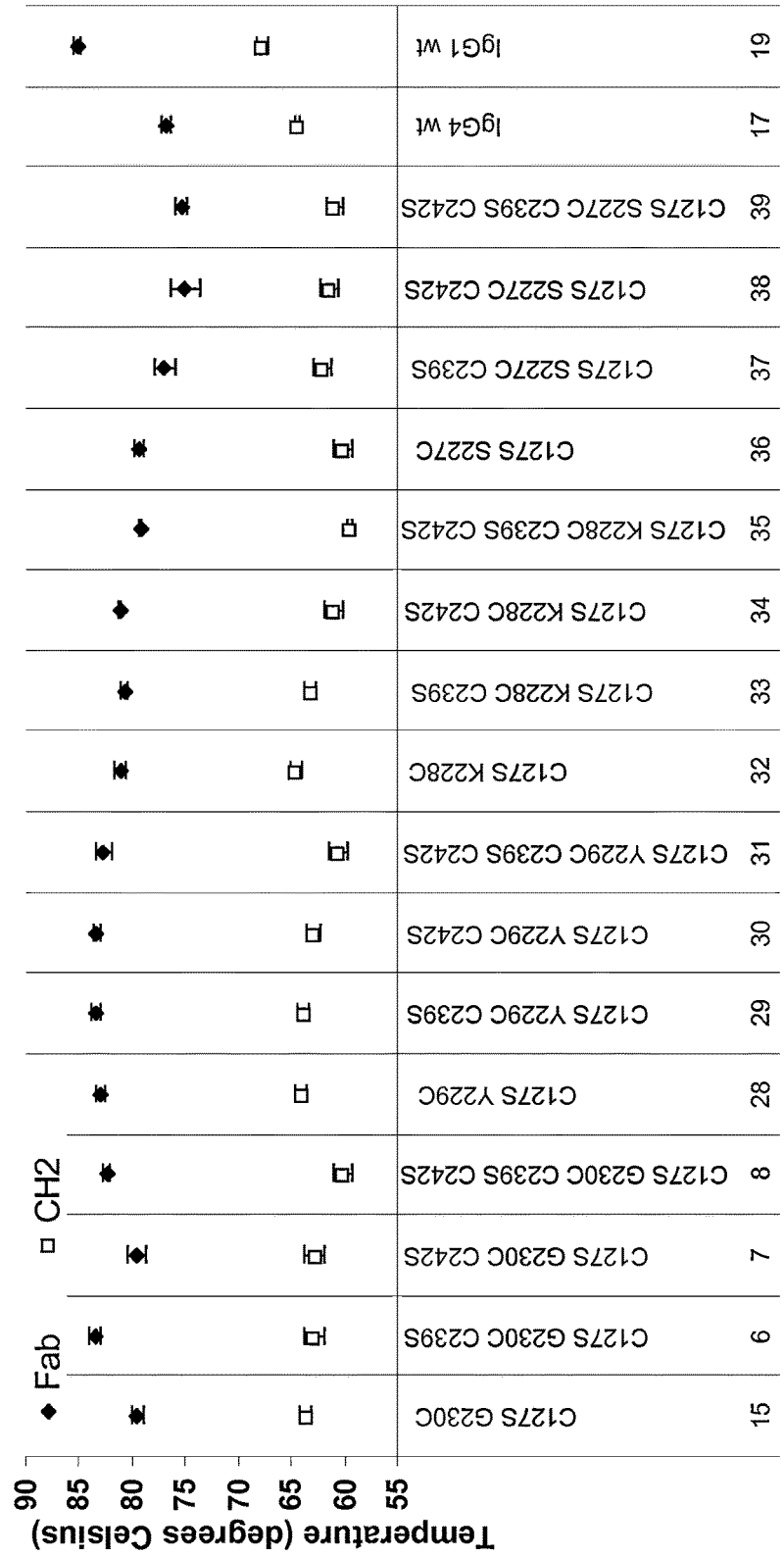

FIG. 12 shows the results of a Thermofluor analysis of antibodies of the present invention which shows the Fab and $C_H2$ domain thermostabilties.

Figure 13:
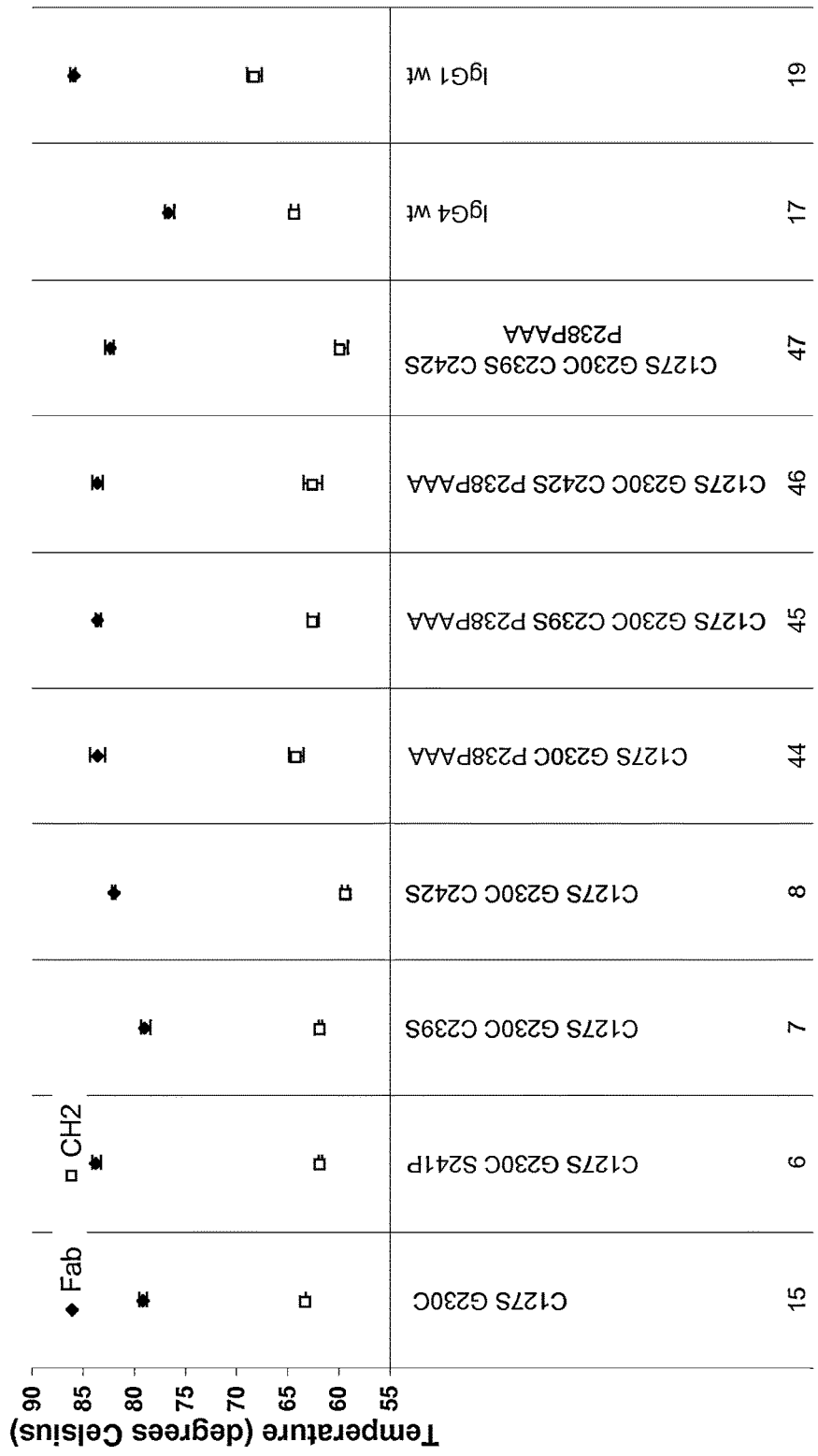

FIG. 13 shows the results of a Thermofluor analysis of antibodies of the present invention which shows the Fab and $C_H2$ domain thermostabilties.

Figure 14:
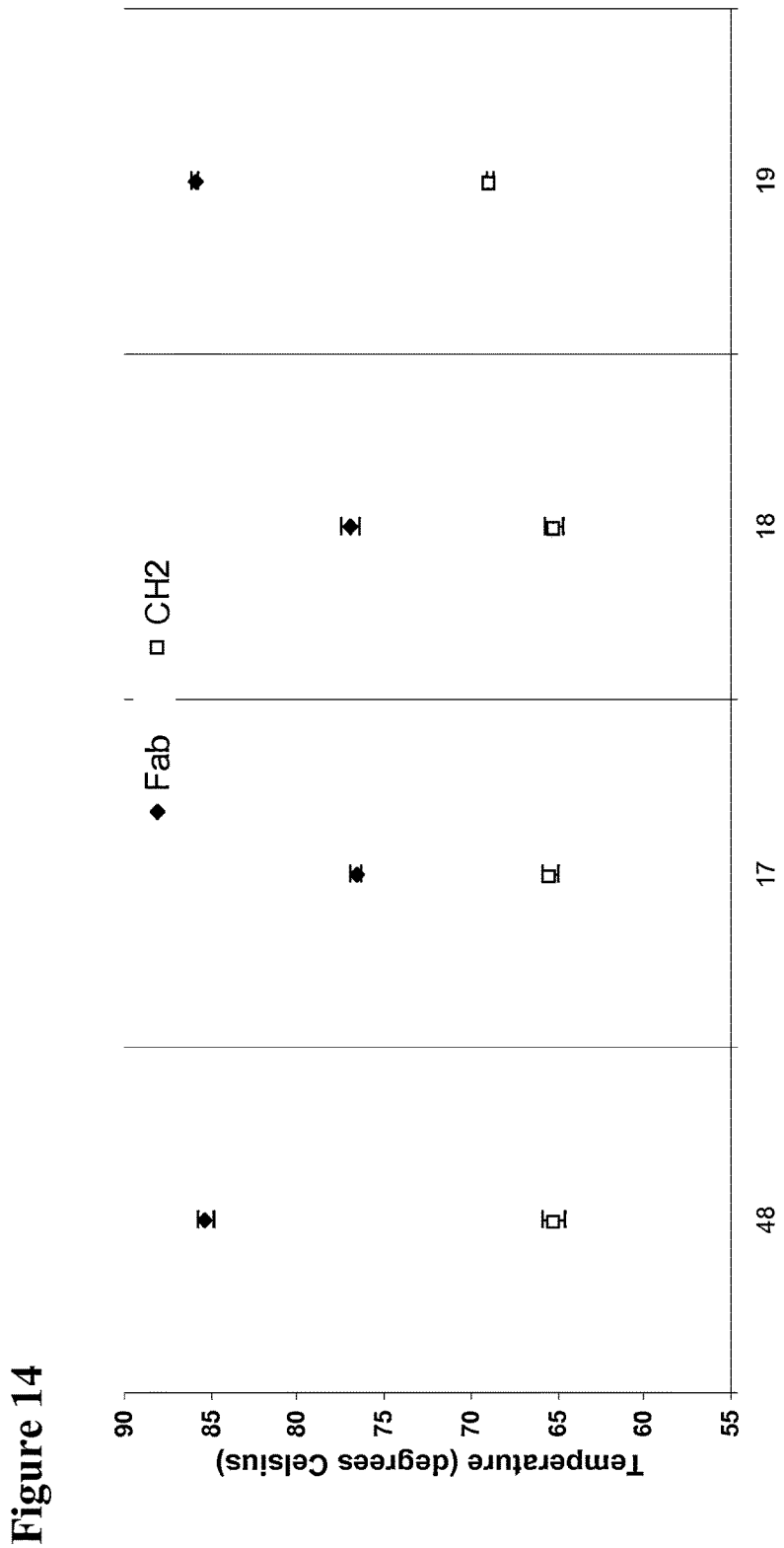

FIG. 14 shows the results of a Thermofluor analysis of antibodies of the present invention which shows the Fab and $C_H2$ domain thermostabilties.

Figure 15:
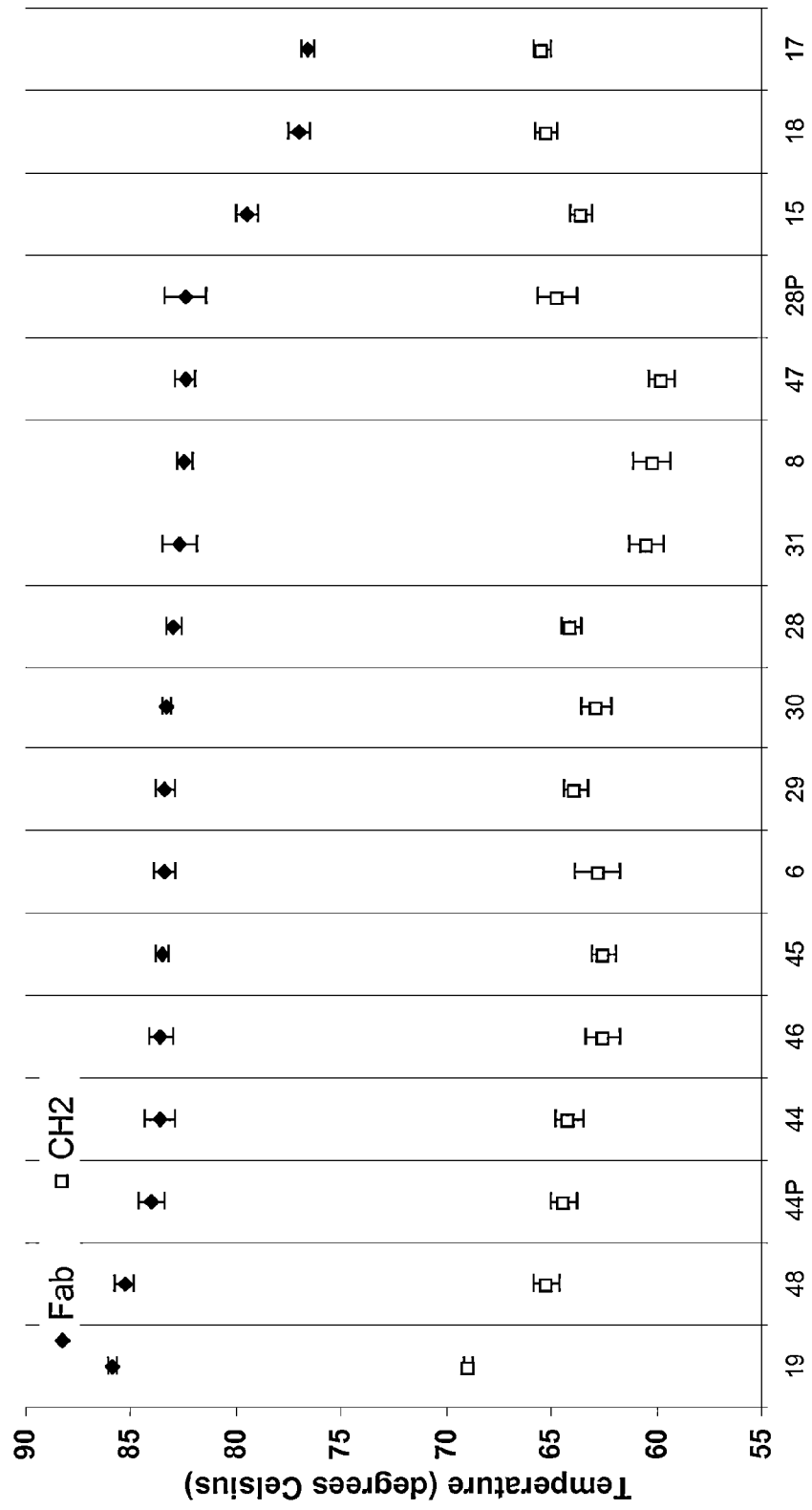

FIG. 15 shows the ranking of the Thermostabilities of selected antibodies of the present invention.

FIG. 16 shows heavy chain exchange at 16 hours wherein the first antibody is selected from IgG1 wild-type, IgG4 wild-type and various mutant antibodies and the second antibody is IgG4 wild-type at two concentrations of GSH. The figures show that the mutants have a little less exchange than the wild-type IgG4 antibodies and significantly greater exchange than the IgG1 wild-type antibody and the IgG4 P antibody. This is advantageous in that the exchange can be used to prepare the asymmetric antibodies of the present disclosure, which in vivo have less susceptibility to undergo exchange than wild type IgG4 antibodies. In some instances increasing the concentration of the reducing agent, such as GSH increases the amount of exchange observed.

FIG. 17 Asymmetric exchange analysis of mutants comprising type 1 variable regions with alternative residues at position 241 with type 2 variable regions.

FIG. 18 Asymmetric exchange analysis of IgG4 WT with type 1 variable regions incubated with different S241 and core hinge cysteine mutants with type 2 variable regions.

FIG. 19 Asymmetric exchange analysis of IgG4 S241P with type 1 variable regions incubated with different 5241 mutants, IgG4 C127S Y229C (Ab 28) with type 2 variable regions FIG. 20 Asymmetric exchange analysis of IgG4 C127S Y229C (number 28) with type 1 variable regions incubated with different S241 mutants and IgG4 WT with type 2 variable regions FIG. 21 Asymmetric exchange analysis of a double hinge mutants with type 1 variable regions incubated with multiple mutants with type 2 variable regions.

BRIEF DESCRIPTION OF THE SEQUENCES

SEQ ID NO: 1 shows the $C_H1$ and hinge region sequence of an IgG1 wild-type antibody.

SEQ ID NO: 2 shows the $C_H1$ and hinge region sequence of an IgG4 wild-type antibody.

SEQ ID NO: 3 shows a part of the constant region of a human wild-type kappa light chain.

SEQ ID NO: 4 shows a part of the N-terminal sequence of the $C_H1$ domain of a human IgG1 antibody.

SEQ ID NO: 5 shows the hinge region of a human IgG1 antibody.

SEQ ID NO: 6 shows a part of the N-terminal sequence of the CH1 domain of a human IgG2 antibody.

SEQ ID NO: 7 shows the hinge region of a human IgG2 antibody.

SEQ ID NO: 8 shows a part of the N-terminal sequence of the CH1 domain of a human IgG3 antibody.

SEQ ID NO: 9 shows the hinge region of a human IgG3 antibody.

SEQ ID NO: 10 shows a part of the N-terminal sequence of the $C_H1$ domain of a human IgG4 antibody.

SEQ ID NO: 11 shows the hinge region of a human IgG4 antibody.

SEQ ID NOs: 12 to 37 show the CH1 domain and hinge region sequences of antibodies 6, 7, 8, 15, 16, 28, 29, 30, 31, 32, 33, 34, 35, 36, 37, 38, 39, 44, 45, 46, 47, 2, 3, 48, 28P and 44P respectively.

SEQ ID NOs: 38 to 63 show the $C_H1$ domain, hinge region, $C_H2$ domain and $C_H3$ domain sequences of antibodies 6, 7, 8, 15, 16, 28, 29, 30, 31, 32, 33, 34, 35, 36, 37, 38, 39, 44, 45, 46, 47, 2, 3, 48, 28P and 44P respectively.

SEQ ID NO: 64 show the wild type IgG4 $C_H2$ and $C_H3$ domain sequences.

SEQ ID NO: 65 shows the wild type IgG4 $C_H2$ and wild type IgG1 $C_H3$ domain sequences.

SEQ ID NO: 66 shows the constant region sequence of a human wild-type kappa light chain.

SEQ ID NO: 67 shows a part of the N-terminal sequence of the $C_H1$ domain of a human IgD antibody.

SEQ ID NO: 68 shows a part of the hinge region of a human IgGD antibody.

SEQ ID NO: 69 shows a part of the N-terminal sequence of the $C_H1$ domain of a human IgM antibody.

SEQ ID NO: 70 shows a part of the C-terminal sequence of the $C_H1$ domain of a human IgM antibody.

SEQ ID NO: 71 shows a part of the $C_H2$ domain of a human IgM antibody.

SEQ ID NO: 72 to 295 shows various hinge regions.

SEQ ID NOs: 296 to 305 show the $C_H1$ domain and hinge region sequences of antibodies 1, 4, 5, 5P, 9, 10, 11, 12, 13 and 14 respectively.

SEQ ID NOs: 306 to 315 show the $C_H1$ domain, hinge region, $C_H2$ domain and $C_H3$ domain sequences of antibodies 1, 4, 5, 5P, 9, 10, 11, 12, 13 and 14 respectively.

SEQ ID NO: 316-322 show various hinge sequences and parts thereof.

DETAILED DESCRIPTION

An asymmetric antibody as employed herein is an antibody where the two heavy chains or fragments thereof have amino acid sequences which are partially or completely different in the regions outside the variable regions, for example having a similarity less than 98% over the relevant portion, such less than 97, 96 95% over the relevant portion. In one embodiment there are 1, 2, 3, 4, 5 amino acids different or added in a region of 10 consecutive amino acids. The amino acid sequences may also be different lengths which by necessity will result in a difference in the amino acid sequence. Parts of the heavy chains may have similar or identical sequences, for example the variable regions in the heavy chain may be the same or different.

In one embodiment the heavy chain sequences in the antibodies of the present disclosure are covalently linked, for example through an inter-chain disulfide bond, for example a bond that is present naturally in the corresponding wild-type fragment or a bond that has been genetically engineered to be present in the desired location in the chains.

In one aspect the antibodies of the present disclosure are characterized in that the first heavy chain IgG4 sequence or fragment has an IgG1 type hinge.

In one aspect the antibodies of the present disclosure are characterized in that both of the heavy chain sequences or fragments have an IgG1 type hinge.

The wild-type IgG1 upper and core hinge has the sequence EPKSCDKTHTCPPCP SEQ ID NO: 316.

The wild-type IgG4 upper and core hinge has the sequence ESKYGPPCPSCP SEQ ID NO: 317.

IgG1 type hinge as employed herein is intended to refer to wherein one or more, for example 1 to 5, such as 1, 2 or 3 amino acids are inserted into the IgG4 hinge, in particular between EPKYGPP SEQ ID NO: 318 and CPSC and/or one or more of the amino acids YGPP in the IgG4 hinge are replaced, for example to correspond to an amino acid in the IgG1 hinge, in particular G (from YGPP in the IgG4 hinge)

is replaced with C or where Y (from YGPP in the IgG4 hinge) is replaced with C or S.

Thus the present invention also provides an asymmetric mixed antibody comprising a first IgG4 heavy chain with an upper hinge, core and lower hinge, and said upper hinge and core in the heavy chain or each heavy chain therein is 13 to 17, such as 15 amino acids in length.

In one embodiment the asymmetric mixed antibody with a first IgG4 heavy chain has an upper hinge and core of 15 amino acids in length.

In one embodiment the upper hinge and core of at least the first heavy chain comprises the natural 12 amino acids found in an IgG4 hinge and a further three amino acids, for example 3 alanine residues, or 3 glycine residues or a combination thereof.

In one embodiment the hinge has the one of the following sequences:

ESKYGPPAAACPSCP;  SEQ ID No: 72

ESKYGPPGGGCPSCP;  SEQ ID No: 73

ESKYGPPTHTCPSCP;  SEQ ID No: 74

ESKYGDKTHTCPSCP;  SEQ ID No: 75

EPSKYGPPAAACPSCP;  SEQ ID No: 76

EPSKYGPPGGGCPSCP;  SEQ ID No: 77

EPSKYGPPTHTCPSCP;  SEQ ID No: 78

EPSKYGDKTHTCPSCP;  SEQ ID No: 79

ESKSYGPPAAACPSCP;  SEQ ID No: 80

ESKSYGPPGGGCPSCP;  SEQ ID No: 81

ESKSYGPPTHTCPSCP;  SEQ ID No: 82

ESKSYGDKTHTCPSCP;  SEQ ID No: 83

ESKYGPPAAACPPCP;  SEQ ID No: 84

ESKYGPPGGGCPPCP;  SEQ ID No: 85

ESKYGPPTHTCPPCP;  SEQ ID No: 86

ESKYGDKTHTCPPCP;  SEQ ID No: 87

EPSKYGPPAAACPPCP;  SEQ ID No: 88

EPSKYGPPGGGCPPCP;  SEQ ID No: 89

EPSKYGPPTHTCPPCP;  SEQ ID No: 90

EPSKYGDKTHTCPPCP;  SEQ ID No: 91

ESKSYGPPAAACPPCP;                SEQ ID No: 92

ESKSYGPPGGGCPPCP;                SEQ ID No: 93

ESKSYGPPTHTCPPCP;                SEQ ID No: 94

ESKSYGDKTHTCPPCP.                SEQ ID No: 95

In one embodiment the upper hinge and core in at least the first IgG4 heavy chain of the disclosure consists a natural IgG1 hinge i.e. EPKSCDKTHTCPPC SEQ ID No: 96 or a derivative thereof such as:

EPKSCDKAAACPPCP;                 SEQ ID No: 97

EPKSCDKGGGCPPCP;                 SEQ ID No: 98

EPKSCDKTHTSPPCP;                 SEQ ID No: 99

EPKSCDKTHTCPPSP;                 SEQ ID No: 100

EPKSCDKTHTSPPSP;                 SEQ ID No: 101

EPKSCDKAAASPPCP;                 SEQ ID No: 102

EPKSCDKAAACPPSP;                 SEQ ID No: 103

EPKSCDKAAASPPSP;                 SEQ ID No: 104

EPKSCDKGGGSPPCP;                 SEQ ID No: 105

EPKSCDKGGGCPPSP;                 SEQ ID No: 106

EPKSCDKGGGSPPSP.                 SEQ ID No: 107

Generally the hinge region in each of the heavy chains of the asymmetric mixed antibody will at least be compatible. That is to say when heavy chains are paired the arrangement will not be unstable, for example due to internal strain in the hinge region.

In one embodiment the hinge region of each heavy chain comprises a sequence independently selected from a hinge sequence disclosed herein.

In one embodiment the hinge in each of the heavy chains is similar or identical. This may be advantageous in that it may minimize incompatibility of the hinge regions of the two chains.

In a further aspect the invention provides an asymmetric mixed antibody comprising two IgG4 heavy chains which each comprises a variable region, a $C_H1$ domain and a hinge region, wherein in the first heavy chain:
  a. the inter-chain cysteine at position 127, numbered according to the Kabat numbering system, in the $C_H1$ domain is substituted with another amino acid; and
  b. the hinge in the heavy chain or each heavy chain therein is in the range 12 to 17, such as 15 amino acids in length
wherein part or all of the second heavy chain has a different amino acid sequence to said first heavy chain in at least the region outside the variable region.

Suitable hinges are described above.

In a further aspect, the present invention also provides an asymmetric antibody comprising two IgG4 heavy chains which each comprises a $C_H1$ domain and a hinge region, wherein in the first heavy chain:
  a. the cysteine at position 127, numbered according to the Kabat numbering system, is substituted with another amino acid; and
  b. the cysteine at position 239 or the cysteine at position 242, numbered according to the Kabat numbering system, are substituted with another amino acid
wherein part or all of the second heavy chain has a different amino acid sequence to said first heavy chain in at least the region outside the variable region.

In one embodiment according to the latter aspect of the invention at least the IgG4 heavy chain contains 22 amino acids in the hinge, for example as described above.

The second heavy chain sequences and fragments include any antibody heavy chain, including IgG1, IgG2, IgG3, IgG4 (including of the type described above), IgD and IgM.

In a further embodiment, the present invention also provides an asymmetric mixed antibody comprising two IgG3 heavy chains which each comprises a $C_H1$ domain and a hinge region, for example wherein in the first heavy chain
  a. the cysteine in the $C_H1$ domain which forms an inter-chain disulphide bond with a cysteine in a light chain is substituted with another amino acid; and
  b. one or more of the amino acids positioned in the upper hinge region is substituted with cysteine.
wherein part or all of the second heavy chain has a different amino acid sequence to said first heavy chain in at least the region outside the variable region.

In a further embodiment, the present invention provides an asymmetric mixed antibody further comprising two IgM heavy chains which each comprises a $C_H1$ domain and a $C_H2$ domain, for example wherein in the first heavy chain:
  a. the cysteine in the $C_H1$ domain which forms an inter-chain disulphide bond with a cysteine in a light chain is substituted with another amino acid; and
  b. one or more of the amino acids positioned in the $C_H1$ domain or $C_H2$ domain is substituted with cysteine;
wherein part or all of the second heavy chain has a different amino acid sequence to said first heavy chain in at least the region outside the variable region.

In a further embodiment, the present invention provides an asymmetric mixed antibody further comprising two IgD heavy chain, for example which each comprise a $C_H1$ domain and a hinge region, wherein in the first heavy chain:
  a. the cysteine in the $C_H1$ domain which forms an inter-chain disulphide bond with a cysteine in a light chain is substituted with another amino acid; and
  b. one or more of the amino acids positioned in the hinge region is substituted with cysteine
wherein part or all of the second heavy chain has a different amino acid sequence to said first heavy chain in at least the region outside the variable region.

Whilst not wishing to be bound by theory it is suspected that the $C_H3$ region of the IgG4 antibodies has a function to play in the dynamic exchange process. Therefore replacement of $C_H3$ region of a non-IgG4 class antibody with a $C_H3$ domain from an IgG4 antibody may render the mutated antibody more conducive to exchange.

In one embodiment the one or more cysteine(s) which would naturally be involved in the formation of an inter-chain disulphide bond between the light chain and heavy chain is replaced by a non-cysteine amino acid, as described in WO2005/003170 and WO2005/003171 both incorporated herein by reference.

In one embodiment the human kappa light in an antibody or fragment according to the present disclosure has one or more of residues 171, 156, 202 or 203 replaced as described in WO2008/038024 incorporated herein by reference.

The skilled person will appreciate that the mutations made to the IgG4 antibody may also be applied to other antibody isotypes or classes which have the same disulphide bond arrangement as an IgG4 antibody in order to provide an improved antibody. Specific examples of antibodies which have the same disulphide bond arrangement as an IgG4 antibody are IgG3 antibodies, IgM antibodies and IgD antibodies. As shown in FIG. 1b, IgG3 and IgM have a cysteine at position 127 in the $C_H1$ domain and IgD has a cysteine at position 128 in the $C_H1$ domain which is equivalent to the C127 in the $C_H1$ domain of IgG4 which forms an inter-chain disulphide bond with a cysteine in the light chain. Further, it can also be seen from FIG. 1b that upper hinge regions of IgG3 and IgD and the C-terminal region of the $C_H1$ domain and the N-terminal region of the $C_H2$ domain in IgM do not contain a cysteine residue which is equivalent to the residues of the upper hinge region of IgG1. Accordingly, the present invention further provides an IgG3 antibody, an IgD antibody and an IgM antibody wherein the cysteine in the $C_H1$ domain which forms an inter-chain disulphide bond with a cysteine in a light chain is substituted with another amino acid and wherein one or more amino acids which are in a structurally analogous position to the upper hinge region of IgG1 or IgG4 are substituted with cysteine. These mutated heavy chains may be employed, for example as the second heavy chain of antibodies according to the disclosure.

In one embodiment the antibody according to the disclosure comprises two IgG4 class heavy chains.

In one embodiment the antibody according to the present disclosure further comprises two light chains.

In one embodiment the antibody according to the present disclosure comprises two variable regions.

In one embodiment the two variable regions have the same specificity, that is to say they are specific to the same antigen.

In one aspect the present disclosure provides an asymmetric mixed antibody with wherein the variable regions are have a different specificity, i.e. a bi-specific antibody. That is to say where the antibody comprises two heavy chain variable regions each variable region is specific for a different antigen.

In one embodiment each variable region can independently bind the target antigen.

The present antibody format is advantageous in that is readily accessible from routine antibody production methods and utilizing naturally occurring mechanisms.

In one embodiment the one or both heavy chain C-terminus is/are fused to a domain antibody, for example with specificity for a distinct antigen, that is an antigen that the variable regions of the heavy chains are not specific to.

Single variable domains also known as single domain antibodies or dAbs for use in the present invention can be generated using methods known in the art and include those disclosed in WO2005118642, Ward et al., 1989, Nature, 341, 544-546 and Holt et al., 2003, *Trends in Biotechnology*, 21, 484-490. In one embodiment a single domain antibody for use in present invention is a heavy chain variable domain (VH) or a light chain domain (VL). Each light chain domain may be either of the kappa or lambda subgroup. Methods for isolating VH and VL domains have been described in the art, see for example EP0368684 and Ward et al., supra. Such domains may be derived from any suitable species or antibody starting material. In one embodiment the single domain antibody may be derived from a rodent, a human or other species. In one embodiment the single domain antibody is humanised.

In one embodiment the single domain antibody is derived from a phage display library, using the methods described in for example, WO2005/118642, Jespers et al., 2004, *Nature Biotechnology*, 22, 1161-1165 and Holt et al., 2003, *Trends in Biotechnology*, 21, 484-490. Preferably such single domain antibodies are fully human but may also be derived from other species. It will be appreciated that the sequence of the single domain antibody once isolated may be modified to improve the characteristics of the single domain antibody, for example solubility, as described in Holt et al., supra.

In one embodiment the or each domain antibody is a VH or VHH.

In one embodiment there are two domain antibodies, one fused to each heavy chain, wherein the two domain antibodies form a VH/VL pairing which bind to the antigen to which they are specific co-operatively.

In one embodiment the antibody of the disclosure is isolated, that is to say not located in a human or an animal body.

The terms "protein" and "polypeptide" are used interchangeably herein, unless the context indicates otherwise. "Peptide" is intended to refer to 10 or less amino acids.

The terms "polynucleotide" includes a gene, DNA, cDNA, RNA, mRNA etc unless the context indicates otherwise.

As used herein, the term "comprising" in context of the present specification should be interpreted as "including".

The term "wild-type" in the context of the present invention means an antibody as it may occur in nature or may be isolated from the environment, which does not comprise any genetically engineered mutations.

The designation for a substitution mutant herein consists of a letter followed by a number followed by a letter. The first letter designates the amino acid in the wild-type protein. The number refers to the amino acid position where the amino acid substitution is being made, and the second letter designates the amino acid that is used to replace the wild-type amino acid.

The residues in antibody variable and constant domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)").

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

Alternatively, the numbering of amino acid residues may be performed by the EU-index or EU numbering system (also described in Kabat et al., Sequences of Proteins of Immunological Interest, 5th Ed. Public Health Service, National Institutes of Health, Bethesda, Md. (1991)).

A further numbering system of amino acid residues in antibodies is the IMGT numbering system (Lefranc, M.-P. et al., Dev. Comp. Immunol., 29, 185-203 (2005)).

The Kabat numbering system is used in the present specification except where otherwise indicated that the EU numbering system or IMGT numbering system is used.

Between the four IgG isotypes, the intrachain disulphide bonding arrangements in the heavy and light chain are similar whereas the interchain disulphide bonding arrangements are unique for each isotype [Reviewed by (Wypych, J., Li, M., Guo, A., Zhang, Z., Martinez, T., Allen, M. J., Fodor, S., Kelner, D. N., Flynn, G. C., Liu, Y. D., Bondarenko, P. V., Ricci, M. S., Dillon, T. M., Balland, A., 2008. Human IgG2 antibodies display disulphide-mediated structural isoforms. J Biol Chem. 283, 16194-16205)].

As shown in FIG. 1b, the hinge region sequences of the four IgG isotypes differ. The complete or genetic hinge region typically consists of residues 226 to 251 (numbering based on Kabat numbering system). FIG. 1b shows the upper, core and lower sections of the hinge regions of the four IgG isotypes. For the IgG1 isotype, the upper hinge region is residues 226 to 238, the core hinge region is residues 239 to 243 and the lower hinge region is residues 244 to 251. For the IgG4 isotype, the upper hinge region is residues 226 to 238, the core hinge region is residues 239 to 243 and the lower hinge region is residues 244 to 251.

Thus the hinge comprising the upper hinge, core and lower hinge in an IgG1 is 23 amino acids in length as shown in FIG. 1a. The upper hinge is 10 amino acids. The core is 5 amino acids and the lower hinge is 8, see for example FIG. 1b.

The hinge comprising the upper hinge, core and lower hinge in an IgG4 is 20 amino acids in length as shown in FIG. 1a. The upper hinge is 7 amino acids. The core is 5 amino acids and the lower hinge is 8, see for example FIG. 1b.

The new mutant IgG4 antibodies according to the present invention have been developed by modifying the interchain disulphide bond arrangements within IgG4, specifically the $C_L$-$C_H1$ interchain disulphide bond arrangement between the light chain (LC) and heavy chain (HC) has been modified.

FIG. 1b shows sections of the human IgG heavy and light chain sequences for the IgG 1-4 isotypes indicating the cysteine positions (underlined) that form the $C_L$-$C_H1$ interchain disulphide bonds. The inter $C_L$-$C_H1$ disulphide bond of IgG1 is formed between the LC C214 (Kabat numbering system) and C233 (Kabat numbering system) of the HC just before the hinge region. In contrast, the $C_H1$-$C_L$ disulphide bond for IgG2, 3 and 4 is formed between the LC C214 and C127 N-terminal to the intrachain disulphide bond of the HC. The LC and HC sequences surrounding the cysteine residues involved in the $C_L$-$C_H1$ disulphide bond formation are shown and aligned in FIG. 1b.

The present invention has investigated how the $C_L$-$C_H1$ disulphide bond affects the properties of an IgG4 antibody including the thermostability, structural stability, disulphide isoform heterogeneity, affinity and half-molecule exchange of the antibody.

Mutants of IgG4 may be generated by substitution of the cysteine residue in $C_H1$ at position 127 with another amino acid as well as substituting one or more of the amino acids in the upper hinge region, preferably amino acids at positions selected from 227, 228, 229 and 230, numbered according to the Kabat numbering system of IgG4, with cysteine. Positions 227, 228, 229 or 230 are at or near to the equivalent structural position that the IgG1 cysteine 233 is situated.

Each heavy chain may comprise further mutations including the substitution of one or both cysteine residues 239 and 242 in the IgG4 hinge region with another amino acid. A mutation to lengthen the IgG4 upper hinge region by three amino acids between positions 238 and 239 to be the same length as the IgG1 hinge may also be included in some antibodies. The S241P mutation was also introduced in some antibodies.

Hence in one embodiment, an IgG4 antibody is provided in which the cysteine 127 is substituted for another amino acid and the cysteine of the light chain is linked via a disulphide bond to an engineered cysteine at position 227, 228, 229 or 230.

In one embodiment the upper hinge and core region is selected from one of the following sequences:

|  |  |
|---|---|
| ESKYGPPCPSCP; | SEQ ID No: 108 |
| ESKYGDKCPSCP; | SEQ ID No: 109 |
| EPSKYGPPCPSCP; | SEQ ID No: 110 |
| EPSKYGDKCPSCP; | SEQ ID No: 111 |
| ESKSYGPPCPSCP; | SEQ ID No: 112 |
| ESKSYGDKCPSCP; | SEQ ID No: 113 |
| ESKYGPPAACPSCP; | SEQ ID No: 114 |
| ESKYGPPGGCPSCP; | SEQ ID No: 115 |
| ESKYGPPHTCPSCP; | SEQ ID No: 116 |
| ESKYGDKHTCPSCP; | SEQ ID No: 117 |
| EPSKYGPPAACPSCP; | SEQ ID No: 118 |
| EPSKYGPPGGCPSCP; | SEQ ID No: 119 |
| EPSKYGPPHTCPSCP; | SEQ ID No: 120 |
| EPSKYGDKHTCPSCP; | SEQ ID No: 121 |
| ESKSYGPPAACPSCP; | SEQ ID No: 122 |
| ESKSYGPPGGCPSCP; | SEQ ID No: 123 |
| ESKSYGPPHTCPSCP; | SEQ ID No: 124 |
| ESKSYGDKHTCPSCP; | SEQ ID No: 125 |
| ESKYGPPACPSCP; | SEQ ID No: 126 |

-continued

ESKYGPPGCPSCP; SEQ ID No: 127

ESKYGPPTTCPSCP; SEQ ID No: 128

ESKYGDKTTCPSCP; SEQ ID No: 129

EPSKYGPPACPSCP; SEQ ID No: 130

EPSKYGPPGCPSCP; SEQ ID No: 131

EPSKYGPPTTCPSCP; SEQ ID No: 132

EPSKYGDKTTCPSCP; SEQ ID No: 133

ESKSYGPPACPSCP; SEQ ID No: 134

ESKSYGPPGCPSCP; SEQ ID No: 135

ESKSYGPPTTCPSCP; SEQ ID No: 136

ESKSYGDKTTCPSCP; SEQ ID No: 137

ESKYGPPTHCPSCP; SEQ ID No: 138

ESKYGDKTHCPSCP; SEQ ID No: 139

EPSKYGPPTHCPSCP; SEQ ID No: 140

EPSKYGDKTHCPSCP; SEQ ID No: 141

ESKSYGPPTHCPSCP; SEQ ID No: 142

ESKSYGDKTHCPSCP; SEQ ID No: 143

ESKYGPPHTCPSCP; SEQ ID No: 144

ESKYGDKHTCPSCP; SEQ ID No: 145

EPSKYGPPHTCPSCP; SEQ ID No: 146

EPSKYGDKHTCPSCP; SEQ ID No: 147

ESKSYGPPHTCPSCP; SEQ ID No: 148

ESKSYGDKHTCPSCP; SEQ ID No: 149

ESKYGPPTCPSCP; SEQ ID No: 150

ESKYGDKTCPSCP; SEQ ID No: 151

EPSKYGPPTCPSCP; SEQ ID No: 152

EPSKYGDKTCPSCP; SEQ ID No: 153

ESKSYGPPTCPSCP; SEQ ID No: 154

ESKSYGDKTCPSCP; SEQ ID No: 155

ESKYGPPHCPSCP; SEQ ID No: 156

ESKYGDKHCPSCP; SEQ ID No: 157

EPSKYGPPHCPSCP; SEQ ID No: 158

EPSKYGDKHCPSCP; SEQ ID No: 159

ESKSYGPPHCPSCP; SEQ ID No: 160

ESKSYGDKHCPSCP; SEQ ID No: 161

EPKSCDKAACPPCP; SEQ ID No: 162

EPKSCDKGGCPPCP; SEQ ID No: 163

EPKSCDKHTSPPCP; SEQ ID No: 164

EPKSCDKHTCPPSP; SEQ ID No: 165

EPKSCDKHTSPPSP; SEQ ID No: 166

EPKSCDKAASPPCP; SEQ ID No: 167

EPKSCDKAACPPSP; SEQ ID No: 168

EPKSCDKAASPPSP; SEQ ID No: 169

EPKSCDKGGSPPCP; SEQ ID No: 170

EPKSCDKGGCPPSP; SEQ ID No: 171

EPKSCDKGGSPPSP; SEQ ID No: 172

EPKSCDKACPPCP; SEQ ID No: 173

EPKSCDKGCPPCP; SEQ ID No: 174

EPKSCDKTSPPCP; SEQ ID No: 175

EPKSCDKTCPPSP; SEQ ID No: 176

EPKSCDKTSPPSP; SEQ ID No: 177

EPKSCDKASPPCP; SEQ ID No: 178

EPKSCDKACPPSP; SEQ ID No: 179

EPKSCDKASPPSP; SEQ ID No: 180

EPKSCDKGSPPCP; SEQ ID No: 181

EPKSCDKGCPPSP; SEQ ID No: 182

EPKSCDKGSPPSP; SEQ ID No: 183

EPKSCDKCPPCP; SEQ ID No: 184

EPKSCDKCPPCP; SEQ ID No: 185

EPKSCDKSPPCP; SEQ ID No: 186

EPKSCDKCPPSP; SEQ ID No: 187

EPKSCDKSPPSP; SEQ ID No: 188

EPKSCDKSPPCP; SEQ ID No: 189

EPKSCDKCPPSP; SEQ ID No: 190

EPKSCDKSPPSP; SEQ ID No: 191

EPKSCDKSPPCP; SEQ ID No: 192

EPKSCDKCPPSP; SEQ ID No: 193

EPKSCDKSPPSP; SEQ ID No: 194

EPKSCDKTTSPPCP; SEQ ID No: 195

EPKSCDKTTCPPSP; SEQ ID No: 196

EPKSCDKTTSPPSP; SEQ ID No: 197

EPKSCDKTHSPPCP; SEQ ID No: 198

EPKSCDKTHCPPSP; SEQ ID No: 199

EPKSCDKTHSPPSP; SEQ ID No: 200

ESKYGPPCPPCP; SEQ ID No: 201

ESKYGPPCPPCP; SEQ ID No: 202

ESKYGPPCPPCP; SEQ ID No: 203

ESKYGDKCPPCP; SEQ ID No: 204

EPSKYGPPCPPCP; SEQ ID No: 205

EPSKYGPPCPPCP; SEQ ID No: 206

EPSKYGPPCPPCP; SEQ ID No: 207

EPSKYGDKCPPCP; SEQ ID No: 208

ESKSYGPPCPPCP; SEQ ID No: 209

ESKSYGPPCPPCP; SEQ ID No: 210

ESKSYGPPCPPCP; SEQ ID No: 211

ESKSYGDKCPPCP; SEQ ID No: 212

ESKYGPPAACPPCP; SEQ ID No: 213

ESKYGPPGGCPPCP; SEQ ID No: 214

ESKYGPPHTCPPCP; SEQ ID No: 215

ESKYGDKHTCPPCP; SEQ ID No: 216

EPSKYGPPAACPPCP; SEQ ID No: 217

EPSKYGPPGGCPPCP; SEQ ID No: 218

EPSKYGPPHTCPPCP; SEQ ID No: 219

EPSKYGDKHTCPPCP; SEQ ID No: 220

ESKSYGPPAACPPCP; SEQ ID No: 221

ESKSYGPPGGCPPCP; SEQ ID No: 222

ESKSYGPPHTCPPCP; SEQ ID No: 223

ESKSYGDKHTCPPCP; SEQ ID No: 224

ESKYGPPACPPCP; SEQ ID No: 225

ESKYGPPGCPPCP; SEQ ID No: 226

ESKYGPPTTCPPCP; SEQ ID No: 227

ESKYGDKTTCPPCP; SEQ ID No: 228

EPSKYGPPACPPCP; SEQ ID No: 229

EPSKYGPPGCPPCP; SEQ ID No: 230

EPSKYGPPTTCPPCP; SEQ ID No: 231

EPSKYGDKTTCPPCP; SEQ ID No: 232

ESKSYGPPACPPCP; SEQ ID No: 233

ESKSYGPPGCPPCP; SEQ ID No: 234

ESKSYGPPTTCPPCP; SEQ ID No: 235

ESKSYGDKTTCPPCP; SEQ ID No: 236

ESKYGPPTHCPPCP; SEQ ID No: 237

ESKYGDKTHCPPCP; SEQ ID No: 238

EPSKYGPPTHCPPCP; SEQ ID No: 239

EPSKYGDKTHCPPCP; SEQ ID No: 240

ESKSYGPPTHCPPCP; SEQ ID No: 241

ESKSYGDKTHCPPCP; SEQ ID No: 242

ESKYGPPHTCPPCP; SEQ ID No: 243

ESKYGDKHTCPPCP; SEQ ID No: 244

EPSKYGPPHTCPPCP; SEQ ID No: 245

EPSKYGDKHTCPPCP; SEQ ID No: 246

ESKSYGPPHTCPPCP; SEQ ID No: 247

ESKSYGDKHTCPPCP; SEQ ID No: 248

ESKYGPPTCPPCP; SEQ ID No: 249

ESKYGDKTCPPCP; SEQ ID No: 250

EPSKYGPPTCPPCP; SEQ ID No: 251

EPSKYGDKTCPPCP; SEQ ID No: 252

ESKSYGPPTCPPCP; SEQ ID No: 253

ESKSYGDKTCPPCP; SEQ ID No: 254

ESKYGPPHCPPCP; SEQ ID No: 255

ESKYGDKHCPPCP; SEQ ID No: 256

EPSKYGPPHCPPCP; SEQ ID No: 257

EPSKYGDKHCPPCP; SEQ ID No: 258

ESKSYGPPHCPPCP; SEQ ID No: 259

ESKSYGDKHCPPCP; SEQ ID No: 260

EPKSCDKTHTCPPCP; SEQ ID No: 261

EPKSCDKTHTCPSCP; SEQ ID No: 262

ESKYCPPACPSCP; SEQ ID No: 263

ESKYCPPAACPSCP; SEQ ID No: 264

ESKYCPPAAACPSCP; SEQ ID No: 265

ESKYCPPAAASPSCP; SEQ ID No: 266

ESKYCPPAAACPSSP; SEQ ID No: 267

ESKCGPPAAACPSCP; SEQ ID No: 268

ESKYCPPAAAACPSCP; SEQ ID No: 269

ESKYCPPAAAAACPSCP; SEQ ID No: 270

ESKYCPPGGGCPSCP; SEQ ID No: 271

ESKYCPPSSSCPSCP; SEQ ID No: 272

ESKYCPPTCPSCP; SEQ ID No: 273

ESKYCPPTHCPSCP; SEQ ID No: 274

ESKYCPPTHTCPSCP; SEQ ID No: 275

ESKYCPKTHTCPSCP; SEQ ID No: 276

ESKYCDKTHTCPSCP; SEQ ID No: 277

ESKYCDKTHCPSCP; SEQ ID No: 278

ESKYCDKTCPSCP; SEQ ID No: 279

ESKYCDKAAACPSCP; SEQ ID No: 280

ESKYCDKCPSCP; SEQ ID No: 281

ESKSCDKTHTCPSCP; SEQ ID No: 282

EPKYCDKTHTCPSCP; SEQ ID No: 283

EPKSCPPCPSCP; SEQ ID No: 284

ESKSCPPCPSCP; SEQ ID No: 285

EPKYCPPCPSCP; SEQ ID No: 286

ECKYGPPCPSCP; SEQ ID No: 287

ECKYGPPSPSCP; SEQ ID No: 288

ECKYGPPCPSSP; SEQ ID No: 289

ESCYGPPCPSCP; SEQ ID No: 290

ESCYGPPSPSCP; SEQ ID No: 291

ESCYGPPCPSSP; SEQ ID No: 292

ESKCGPPCPSCP; SEQ ID No: 293

ESKCGPPSPSCP; SEQ ID No: 294

ESKCGPPCPSSP. SEQ ID No: 295

In one embodiment the core hinge region in one or both heavy chain sequences or fragments thereof has the sequence CPPCP SEQ D3 NO: 322.

Whilst not wishing to be bound by theory it is thought that this sequence is likely to block dynamic exchange of the antibody arms at "in vivo" type concentrations for example concentration of less than 0.5 mM reductant, in particular concentrations of reductant in the order of 5 uM are thought to be physiologically relevant (Zilmer et al., 2005 Drug Design Reviews vol. 2, no. 2, pp. 121-127, 2005).

The mutations to the antibodies of the present invention will now be described in further detail. The methods for replacing amino acids are well known in the art of molecular biology. Such methods include for example site directed mutagenesis using methods such as PCR to delete and/or substitute amino acids or de novo design of synthetic sequences.

FIG. 2a shows the hinge residues of IgG1 wild type, IgG4 wild type and the positions where mutations have been introduced in the antibodies of the present invention. Numbering based on Kabat numbering system.

The antibodies according to the present invention comprise a mutation at position 127 (C127), wherein the cysteine residue is replaced by another amino acid, preferably an amino acid that does not contain a thiol group. By replace or substitute we mean that where the interchain cysteine 127 would normally be found in the antibody heavy chain another amino acid is in its place. The mutation at C127 may be any suitable mutation to one, two or three of the nucleotides encoding the amino acid at position 127 which changes the amino acid residue from cysteine to another suitable amino acid. Examples of suitable amino acids include serine, threonine, alanine, glycine or any polar amino acid. A particularly preferred amino acid is serine.

The substitution of the cysteine at position 127 with another amino acid removes the cysteine in the $C_H 1$ domain which normally forms a disulphide bond with a cysteine in the light chain in the wild-type IgG4. Therefore, in order to form a light chain and heavy chain pairing via an inter-chain disulphide bond the light chain must form a disulphide bond with a cysteine which is positioned in the hinge region of the heavy chain.

In a first aspect of the invention, antibodies according to the present invention comprise a heavy chain wherein one or more of the amino acids at positions selected from 227, 228, 229 and 230, numbered according to the Kabat numbering system, is substituted with cysteine. Accordingly, antibodies according to the present invention may carry one or more of the following mutations: S227C; K228C; Y229C; G230C.

Preferably only one residue selected from 227, 228, 229 and 230 is substituted with a cysteine residue.

Particularly preferred antibodies of the present invention carry the mutation Y229C or G230C.

The inclusion of a cysteine residue at a position selected from 227, 228, 229 and 230, in the hinge region of the heavy chain provides a new position for an inter-chain disulphide bond to form between the heavy chain and the light chain.

Further mutations may be introduced to the antibodies of this aspect of the present invention. In one embodiment the cysteine at position 239 (C239) and/or the cysteine at position 242 (C242), numbered according to the Kabat numbering system, in the heavy chain are substituted with another amino acid, preferably an amino acid that does not contain a thiol group. By replace or substitute we mean that where the cysteine 239 and/or the cysteine 242 would normally be found in the antibody heavy chain another amino acid is in its place. The mutation at C239 and/or C242 may be any suitable mutation to one, two or three of the nucleotides encoding the amino acid which changes the amino acid residue from cysteine to another suitable amino acid. Examples of suitable amino acids include serine, threonine, alanine, glycine or any polar amino acid. A particularly preferred amino acid is serine.

In one embodiment the cysteine at position 239 in the heavy chain is substituted with another amino acid and the cysteine at position 242 in the heavy chain is substituted with another amino acid. In this embodiment, the substitution of both C239 and C242 removes both cysteine residues in the hinge region of the heavy chain which normally form inter-heavy chain disulphide bonds with the corresponding cysteines in another heavy chain. The resulting half-molecules may form whole antibody molecules through non-covalent bonding between two heavy chains.

In an alternative embodiment the cysteine at position 239 in the heavy chain is substituted with another amino acid. In this embodiment the cysteine at position 242 is not substituted with another amino acid.

In a further alternative embodiment the cysteine at position 242 in the heavy chain is substituted with another amino acid. In this embodiment the cysteine at position 239 is not substituted with another amino acid.

The substitution of either C239 or C242, leaves one cysteine in the heavy chain which is capable of forming an inter-heavy chain disulphide bond with a cysteine in another heavy chain. Without being bound by theory it is thought that the substitution of one cysteine in the hinge region, particularly substitution of C239, reduces the formation of an intra-chain disulphide bond in the hinge region and therefore may reduce the formation of half antibody molecules.

In one embodiment of the present invention the proline at position 240 may be substituted with another amino acid.

In one embodiment of the present invention the serine at position 241 may be substituted with another amino acid.

In one embodiment of the present invention, wherein the serine at position 227 is substituted with a cysteine, the antibody preferably does not comprise mutations at positions C239 and C242. In another embodiment, wherein the serine at position 227 is substituted with a cysteine, the cysteine at position 239 in the heavy chain is preferably substituted with another amino acid but the cysteine at position 242 is not substituted with another amino acid.

In one embodiment the antibodies of the present invention comprise an IgG4 heavy chain which is mutated to insert one or more amino acids between amino acids 226-243. The number of amino acids inserted may be 1 to 10, 1 to 5, 1 to 3, preferably 1, 2, 3 or 4 amino acids are inserted. The amino acids are preferably inserted between amino acids 238 and 239. Any suitable amino acids may be inserted in the hinge region, such as alanines, glycines, serines or threonines and combinations thereof. Preferably three alanines (AAA), three glycines (GGG), three serines (SSS) or three threonines (TTT) are inserted or a threonine, histidine and another threonine (THT). It is believed that antibodies of the present invention comprising an IgG4 heavy chain which has been mutated to insert three amino acids in the hinge region show improved stability, for example thermostability.

A further mutation which may be introduced in the antibodies according to the present invention is the mutation S241P. This mutation has been previously shown to reduce the formation of half molecules at biologically relevant concentrations (Angal, S. et al., 1993. A single amino acid substitution abolishes the heterogeneity of chimeric mouse/human (IgG4) antibody. Mol Immunol 30, 105-108). It has been surprisingly found that mutant antibodies of the present invention which comprise the S241P mutation demonstrate some heavy chain exchange in vitro under strong reducing conditions compared to IgG4 P (IgG4 with S241P). This allows the creation of bispecific antibodies in vitro from mutant IgG4 antibodies of the present invention.

The antibodies according to the present invention may comprise one or more further mutations in the hinge region. For example the antibodies may further comprise one or more of the following mutations S227P, Y229S, P237D and P238K.

In one embodiment the antibody according to the present invention effectively comprises an IgG1 hinge region from residue 226 to 243 (upper hinge and core hinge). Accordingly, the antibody of the present invention comprises a hinge region wherein the glycine at position 230 is substituted with cysteine, the serine at position 227 is substituted with proline, the tyrosine at position 229 is substituted with serine, the proline at position 237 is substituted with aspartic acid, the proline at position 238 is substituted with lysine, the amino acid sequence threonine-histidine-threonine is inserted between positions 238 and 239 and the serine at position 241 is substituted with proline. These mutations may also be written as S227P, Y229S, G230C, P237D, P238KTHT and S241P, as shown in FIG. 2a.

The antibody according to the present invention preferably has an IgG4 lower hinge from residue 244 to 251 (APEFLGGP SEQ ID NO: 321). Without being bound by theory it is believed that the IgG4 lower hinge region contributes to the lack of effector function of an IgG4 antibody.

In a second aspect of the present invention, the asymmetric mixed antibody of the present disclosure comprises a heavy chain wherein the cysteine at position 127 is substituted with another amino acid, as described above, and the cysteine at position 239 or the cysteine at position 242, numbered according to the Kabat numbering system, in the heavy chain is substituted with another amino acid. In this second aspect, none of the residues at positions 227, 228, 229 and 230 are substituted with a cysteine residue. Accordingly, there is provided:

an asymmetric mixed antibody comprising two heavy chains each comprising at least a variable region, a hinge region and a $C_H1$ domain, wherein in a first heavy chain or fragment thereof is characterised in that it is a class IgG4 and has:
  a. the inter-chain cysteine at position 127, numbered according to the Kabat numbering system, is substituted with another amino acid; and
  b. optionally the cysteine at position 239 or the cysteine at position 242, numbered according to the Kabat numbering system, is substituted with another amino acid wherein the second heavy chain or fragment thereof is characterised in that it has a different amino acid sequence to said first heavy chain in a region outside the variable region.

In the second aspect of the present invention, the antibody may comprise one or more further mutations. In one embodiment the antibody comprises at least a first IgG4 heavy chain which is mutated to insert three amino acids between amino acids 226-243, preferably between amino acids 238 and 239, as described above. In a further embodiment the antibody comprises the mutation S241P. In a further embodiment, the antibody may further comprise one or more of the following mutations S227P, Y229S, P237D and P238K.

In a one embodiment, the present invention provides an asymmetric mixed antibody comprising two heavy chains which each comprise a variable region, a $C_H1$ domain and hinge (such as two heavy chains independently), each heavy chain independently comprising a sequence selected from one of the following sequences: SEQ ID NO: 12, SEQ ID NO: 13, SEQ ID NO: 14, SEQ ID NO: 15, SEQ ID NO: 16, SEQ ID NO: 17, SEQ ID NO:18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37.

In a one embodiment the asymmetric mixed antibody of the present invention comprises two heavy chains which each comprise a variable region, a $C_H1$ domain and hinge (such as two heavy chains independently), each heavy chain independently comprises a sequence selected from one of the following sequences: SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 29, SEQ ID NO: 30, SEQ ID NO: 31, SEQ ID NO: 32, SEQ ID NO: 35, SEQ ID NO: 36 and SEQ ID NO: 37. More specifically, the asymmetric mixed antibody of the present invention comprises two heavy chains which each comprise a variable region, a $C_H1$ domain and hinge (such as two heavy chains independently), each heavy chain independently comprises a sequence selected from one of the following sequences: SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 29, SEQ ID NO: 30, SEQ ID NO: 31, SEQ ID NO: 32, SEQ ID NO: 35, SEQ ID NO: 36 and SEQ ID NO: 37.

Accordingly, the present invention provides an asymmetric mixed antibody two heavy chains, each comprising, a variable domain, a $C_H1$ domain and hinge, a $C_H2$ domain and a $C_H3$ domain (such as two heavy chains independently) each comprising a sequence independently selected from one of the following sequences: SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62 and SEQ ID NO: 63.

In one embodiment asymmetric mixed antibody of the present invention comprises two heavy chains which each comprise a variable region, a $C_H1$ domain and a hinge region, wherein each heavy chain independently comprises SEQ ID NO: 36 (antibody 28P), SEQ ID NO: 37 (antibody 44P) or SEQ ID NO: 35 (antibody 48).

In one embodiment an asymmetric mixed antibody of the present invention comprises two heavy chains which each comprise a variable region, a $C_H1$ domain, a hinge region, a $C_H2$ domain and a $C_H3$ domain wherein each heavy chain independently comprises SEQ ID NO: 62 (antibody 28P), SEQ ID NO: 63 (antibody 44P) or SEQ ID NO: 61 (antibody 48).

In any of the embodiments above the second heavy chain of the antibody may be selected from any heavy chain sequence disclosed herein.

Table 1 below lists example antibodies with mutations which have been introduced compared to the IgG4 wild-type sequence. Table 1 also includes wild-type IgG1 and IgG4 antibodies and control antibodies. Table 1:

TABLE 1

| Antibody Number | Heavy Chain Mutations (Kabat Numbering) | $C_H1$ domain & Hinge SEQ ID NO: | $C_H1$, Hinge, $C_H2$ & $C_H3$ SEQ ID NO: |
|---|---|---|---|
| 1 | C127S | 296 | 306 |
| 2 | C127S, C239S | 33 | 59 |
| 3 | C127S, C242S | 34 | 60 |
| 4 | C127S, C242S, C239S | 297 | 307 |
| 5 | G230C | 298 | 308 |
| 5P | G230C, S241P | 299 | 309 |
| 6 | C127S, G230C, C239S | 12 | 38 |
| 7 | C127S, G230C, C242S | 13 | 39 |
| 8 | C127S, G230C, C239S, C242S | 14 | 40 |
| 9 | G230C, C239S | 300 | 310 |
| 10 | G230C, C242S | 301 | 311 |
| 11 | G230C, C239S, C242S | 302 | 312 |
| 12 | C239S | 303 | 313 |
| 13 | C242S | 304 | 314 |
| 14 | C239S, C242S | 305 | 315 |
| 15 | C127S, G230C | 15 | 41 |
| 16 | C127S, G230C, S241P | 16 | 42 |
| 17 | Human IgG4 wild type | 2 | — |
| 18 | S241P | — | — |
| 19 | Human IgG1 wild type | 1 | — |
| 28 | C127S Y229C | 17 | 43 |
| 28P | C127S Y229C, S241P | 36 | 62 |
| 29 | C127S Y229C C239S | 18 | 44 |
| 30 | C127S Y229C C242S | 19 | 45 |
| 31 | C127S Y229C C239S C242S | 20 | 46 |
| 32 | C127S K228C | 21 | 47 |
| 33 | C127S K228C C239S | 22 | 48 |
| 34 | C127S K228C C242S | 23 | 49 |
| 35 | C127S K228C C239S C242S | 24 | 50 |
| 36 | C127S S227C | 25 | 51 |
| 37 | C127S S227C C239S | 26 | 52 |
| 38 | C127S S227C C242S | 27 | 53 |
| 39 | C127S S227C C239S C242S | 28 | 54 |
| 44 | C127S G230C P238PAAA | 29 | 55 |
| 44P | C127S G230C P238PAAA, S241P | 37 | 63 |
| 45 | C127S G230C P238PAAA C239S | 30 | 56 |
| 46 | C127S G230C P238PAAA C242S | 31 | 57 |
| 47 | C127S G230C P238PAAA C239S C242S | 32 | 58 |
| 48 | C127S, S227P, Y229S, G230C, P237D, P238KTHT, S241P | 35 | 61 |
| 49 | C127S G230C P238PA | | |
| 50 | C127S G230C P238PAA S241P | | |
| 51 | C127S, G230C, P238PAAAA | | |
| 52 | C127S, G230C, P238PAAAAA | | |
| 55 | C127S, G230C, P238PTHT | | |
| 56 | C127S, G230C, P237D, P238KTHT | | |
| 57 | C127S, G230C, P238PGGG | | |
| 60 | C127S, S227P, G230C | | |
| 62 | C127S, Y229S, G230C | | |
| 64 | C127S, S227P, Y229S, G230C | | |
| 65 | C127S, S227P, Y229S, G230C, P237D, P238KTHT | | |
| 66 | C127S, G230C, P237D, P238KTH | | |
| 67 | C127S, G230C, P237D, P238KT | | |
| 68 | C127S, G230C, P237D, P238K | | |
| 69 | C127S, G230C P237D, P238KAAA | | |

TABLE 1-continued

| Antibody Number | Heavy Chain Mutations (Kabat Numbering) | $C_H1$ domain & Hinge SEQ ID NO: | $C_H1$, Hinge, $C_H2$ & $C_H3$ SEQ ID NO: |
|---|---|---|---|
| 71 | C127S, S227P, G230C, P237D, P238KTHT | | |
| 73 | C127S, Y229S, G230C, P237D, P238KTHT | | |
| 74 | C127S Y229C core hinge SPPCP | | |
| 75 | C127S G230C core hinge CPPSP | | |
| 76 | C127S Y229C core hinge CPPSP | | |
| 77 | C127S G230C core hinge SPPCP | | |

In one embodiment a first IgG4 heavy chain sequence is combined with a second IgG4 heavy chain sequence each comprising the $C_H1$ and upper hinge mutations and core hinge sequences as described in Table 2:

TABLE 2

| FIRST HEAVY CHAIN | SECOND HEAVY CHAIN |
|---|---|
| C127S Y229C (Ab 28) | C127S Y229C S241P (Ab 28P) |
| C127S Y229C S241P (Ab 28P) | IgG4 WT |
| C127S Y229C (Ab 28) | IgG4 WT |
| C127S G230C (Ab 15) | C127S G230C S241P (Ab 16) |
| C127S G230C S241P (Ab 15P) | IgG4 WT |
| C127S G230C (Ab 15) | IgG4 WT |
| C127S + IgG1 hinge (Ab 48) | C127S G230C (Ab 15) |
| C127S + IgG1 hinge (Ab 48) | C127S G230C S241P (Ab 15P) |
| C127S + IgG1 hinge (Ab 48) | C127S Y229C (Ab 28) |
| C127S + IgG1 hinge (Ab 48) | C127S Y229C S241P (Ab 28P) |
| C127S + IgG1 hinge (Ab 48) | C127S, S227P, Y229S, G230C, P237D, P238KTHT (Ab 65) |
| C127S Y229C core hinge SPPCP (Ab 74) | C127S Y229C core hinge CPPCP or core hinge CPSCP (Ab 28P or 28) |
| C127S Y229C core hinge SPSCP (Ab 29) | C127S Y229C core hinge CPPCP or core hinge CPSCP (Ab 28P or 28) |
| C127S G230C core hinge SPSCP (Ab 6) | C127S G230C core hinge CPPCP or core hinge CPSCP (Ab 16 or 15) |
| C127S G230C core hinge CPPSP (Ab 75) | C127S G230C core hinge CPPCP or core hinge CPSCP (Ab 16 or 15) |
| C127S G230C core hinge CPPSP (Ab75) | C127S Y229C core hinge CPPCP or core hinge CPSCP (Ab 28P or 28) |
| C127S Y229C core hinge CPPSP (Ab 76) | C127S Y229C core hinge CPPCP or core hinge CPSCP (Ab 28P or 28) |
| C127S Y229C core hinge CPPSP (Ab 76) | C127S G230C core hinge CPPCP or core hinge CPSCP (Ab 16 or 15) |
| C127S G230C P238PAAA (Ab 44) | C127S G230C P238PAAA S241P (Ab 44P) |
| C127S G230C P238PAAA (Ab 44) | IgG4 WT P238PAAA |
| C127S G230C P238PAAA (Ab 44) | IgG4 WT |
| C127S G230C P238PAAA S241P (Ab 44P) | IgG4 WT |
| C127S + IgG1 hinge (Ab 48) | IgG4 WT |
| C127S, S227P, Y229S, G230C, P237D, P238KTHT (Ab 65) | IgG4 WT |
| IgG4 wild type (S241) | S241G |
| | S241A |
| | S241D |
| | S241E |
| | S241K |
| | S241T |
| | S241P |
| | C127C and Y229C |
| IgG4 S241G | S241A |
| | S241T |
| | S241D |
| | S241E |
| | S241K |
| IgG4 S241T | S241A |
| IgG4 wild type (S241) | C239S |
| | C242S |
| | C239C and C242C |
| | C127C and Y229C |
| IgG4 S241P | C127C and Y229C |
| | S241G |
| | S241A |
| | S241T |
| | S241D |
| | S241E |
| | S241K |
| | C239C and C242C |
| IgG4 C127S and Y229C | S241G |
| | S241A |
| | S241T |
| | S241D |
| | S241E |
| | S241K |
| | C239C and C242C |
| IgG4 C239C and C242C | S241G |
| | S241A |
| | S241T |
| | S241D |
| | S241K |
| | S241E |
| | C239C and C242C |
| | C239S |
| | C242S |

Accordingly the present invention provides an asymmetric mixed antibody comprising two heavy chains each comprising at least a variable region, a hinge region and a $C_H1$ domain, wherein a first heavy chain and second heavy chain sequences are IgG4 heavy chain sequences selected from the combinations of first and second heavy chain sequence mutations listed in Table 2.

The asymmetric mixed antibody may comprise a first and second heavy chain, wherein each heavy chain constant sequence comprises mutations to the $C_H1$ domain and hinge region as described above, and wherein the mutations to the $C_H1$ domain and hinge region in each heavy chain are different. Alternatively, the first heavy chain constant sequences may comprise mutations to the $C_H1$ domain and hinge region as described above and the second heavy chain constant sequence is IgG4 wild type or IgG4 wild type with S241P mutation.

In one embodiment of the present invention, the asymmetric mixed antibody is a bispecific antibody, wherein each heavy chain has different variable regions. The antibody preferable also comprises two light chains, wherein each heavy-light chain pair (Fab) has different variable regions.

"Different variable regions" as employed herein is intended to refer to wherein the said variable regions have specificity for different antigens. That is to say that the antigen to which each variable region is specific is a different antigen or a different part of an antigen, eg a different epitope.

"Specific" as employed herein refers to the fact the binding domains recognized a target antigen with greater affinity and/avidity than other antigens to which it is not specific (for example 10, 20, 50, 10 or 1000 greater). It does not necessarily imply that the specific binding region does not bind any non-target antigens but rather the interaction with the target is such that it can be used to purify the target antigen (to which it is specific) from a complex mixture of antigens, including antigens in the same family of proteins.

In one embodiment the antibody according to the present disclosure is isolated.

Isolated as employed herein is intended to refer to an antibody that is isolated from the human body, for example: prepared by recombinant techniques, purified using a technique such as chromatography, and/or in a pharmaceutical formulation.

The term 'antibody' as used herein includes intact (whole) antibodies and functionally active fragments which comprise two heavy chains which each comprise a $V_H$ domain, a $C_H1$ domain and a hinge region. The antibody according to the present invention preferably comprises at least one light chain. Accordingly, the term "antibody" in the present invention covers bi, tri or tetra-valent antibodies, a dimer of Fab' and F(ab')$_2$ fragments and whole antibody molecules comprising two light chain and heavy chain pairings.

As is well known in the art, a typical Fab' molecule comprises a heavy and a light chain pair in which the heavy chain comprises a variable region $V_H$, a constant domain $C_H1$ and a hinge region and the light chain comprises a variable region VL and a constant domain $C_L$.

In one embodiment there is provided a dimer of Fab' according to the present disclosure for example dimerisation may be through the hinge.

In one embodiment the heavy chain comprises a $C_H2$ domain and a $C_H3$ domain and optionally a $C_H4$ domain. In one embodiment the antibody comprises two heavy chains each of which is as defined above in the first or second aspect of the present invention. The antibodies according to the present invention also preferably comprise two light chains, which may be the same or different. In the embodiment of the present invention which provides a bispecific antibody which comprises two heavy chains, as defined above, and two light chains, the two light chains have different variable regions and may have the same or different constant regions.

In one embodiment the $C_H2$ and $C_H3$ domains employed may be mutated, for example in order to reduce the formation of aggregates of IgG4 antibodies. US 2008/0063635 Takahashi et al. has investigated a mutant of IgG4 in which arginine at position 409 (409 numbered according to EU numbering system or 440 numbered according to the Kabat numbering system) in the $C_H3$ domain is substituted with lysine, threonine, methionine or leucine in order to inhibit aggregate formation at low pH. Further mutations at L235, D265, D270, K322, P329 and P331 (L235, D265, D270, K322, P329 and P331 numbered according to EU numbering system or L248, D278, D283, K341, P348 and P350 numbered according to the Kabat numbering system) are also taught in order to attenuate CDC activity. WO2008/145142 Van de Winkel et al. discloses stable IgG4 antibodies that have a reduced ability to undergo "Fab-arm exchange" (referred to herein as dynamic heavy chain exchange) by substitution of the arginine residue at position 409, the Phe residue at position 405 or the Lys at position 370 (R409, F405 and K370 numbered according to EU numbering system or R440, F436 and K393 numbered according to the Kabat numbering system) even in the absence of the S228P (S228 numbered according to EU numbering system or S241 according to the Kabat numbering system) mutation in the hinge region.

In one embodiment the antibody of the present invention is a whole asymmetric mixed antibody comprising two light chains and two heavy chains, wherein each heavy chain comprises an IgG4 $C_H1$ wherein the cysteine at position 127, numbered according to the Kabat numbering system is substituted with another amino acid, an IgG1 upper and middle hinge region, an IgG4 lower hinge region, a $C_H2$ domain and a $C_H3$ domain.

The complete hinge region of an IgG4 antibody typically consists of residues 226 to 251 (numbering based on Kabat numbering system. However the hinge region may be shortened or lengthened as required. For example, antibodies according to the first aspect of the present invention, the wild type amino acid is substituted with a cysteine residue at position 227, 228, 229 or 230, the hinge region may end after the new cysteine residue at position 227, 228, 229 or 230. Antibodies according to the present invention may also comprise one or more further amino acids positioned N-terminal and/or C-terminal of the hinge region. In addition other characteristics of the hinge can be controlled, such as the distance of the hinge cysteine(s) from the light chain interchain cysteine, the distance between the cysteines of the hinge and the composition of other amino acids in the hinge that may affect properties of the hinge such as flexibility e.g. glycines may be incorporated into the hinge to increase rotational flexibility or prolines may be incorporated to reduce flexibility. Alternatively combinations of charged or hydrophobic residues may be incorporated into the hinge to confer multimerisation or purification properties. Other modified hinge regions may be entirely synthetic and may be designed to possess desired properties such as length, composition and flexibility.

The constant region domains, in particular in the Fc domain, where present, employed in the present invention, are preferably of IgG4 isotype where antibody effector functions are not required. According each heavy chain preferably comprises an IgG4 $C_H2$ domain and a $C_H3$ domain, as shown in SEQ ID NO: 64.

It will be appreciated that sequence variants of the Fc constant region domains may also be used.

In one embodiment each heavy chain comprises IgG4 $C_H2$ and $C_H3$ domains wherein the arginine at position 409 (EU numbering) is substituted with lysine, threonine, methionine or leucine in order to inhibit aggregate formation at low pH (US 2008/0063635 Takahashi et al.) Mutations at L235, D265, D270, K322, P331 and P329 (numbered according to EU numbering system) are also taught in order to attenuate CDC activity (US 2008/0063635 Takahashi et al.).

Each heavy chain may comprise the mutations as taught in WO2008/145142 Van de Winkel et al. which discloses stable IgG4 antibodies that have a reduced ability to undergo Fab-arm exchange by substitution of the arginine residue at position 409, the Phe residue at position 405 or the Lys at position 370 (numbered according to EU numbering system).

In one embodiment each heavy chain comprises an IgG4 $C_H2$ domain and an IgG1 $C_H3$ domain, as shown in SEQ ID NO: 65.

In the embodiment of the present invention wherein the antibody is a mutated IgG3, IgD or IgM antibody, each heavy chain preferably comprises a $C_H2$ domain and a $C_H3$ domain, and optionally a $C_H4$ domain. In the IgG3 antibody each heavy chain preferably comprises IgG3 $C_H2$ domain and a IgG3 $C_H3$ domain. In the IgD antibody each heavy chain preferably comprises IgD $C_H2$ domain and a IgD $C_H3$ domain. In the IgM antibody each heavy chain preferably comprises IgM $C_H2$ domain, a IgM $C_H3$ domain and a IgM $C_H4$ domain.

In one embodiment, the antibody is a monoclonal, fully human, humanized or chimeric antibody fragment. In one embodiment the antibody is fully human or humanised.

Monoclonal antibodies may be prepared by any method known in the art such as the hybridoma technique (Kohler & Milstein, *Nature*, 1975, 256, 495-497), the trioma technique, the human B-cell hybridoma technique (Kozbor et al., *Immunology Today*, 1983, 4, 72) and the EBV-hybridoma technique (Cole et al., "Monoclonal Antibodies and Cancer Therapy", pp. 77-96, Alan R. Liss, Inc., 1985).

Antibodies for use in the invention may also be generated using single lymphocyte antibody methods by cloning and expressing immunoglobulin variable region cDNAs generated from single lymphocytes selected for the production of specific antibodies by, for example, the methods described by Babcook, J. et al., *Proc. Natl. Acad. Sci. USA*, 1996, 93(15), 7843-7848, WO 92/02551, WO2004/051268 and WO2004/106377.

Humanized antibodies are antibody molecules from non-human species having one or more complementarity determining regions (CDRs) from the non-human species and a framework region from a human immunoglobulin molecule which optionally comprise one or more donor residues from the non-human species (see, for example, U.S. Pat. No. 5,585,089).

The antibodies for use in the present invention can also be generated using various phage display methods known in the art and include those disclosed by Brinkman et al., *J. Immunol. Methods*, 1995, 182, 41-50; Ames et al., *J. Immunol. Methods*, 1995, 184, 177-186; Kettleborough et al. *Eur. J. Immunol.*, 1994, 24, 952-958; Persic et al., *Gene*, 1997 187, 9-18; and Burton et al., *Advances in Immunology*, 1994, 57, 191-280; WO 90/02809; WO 91/10737; WO 92/01047; WO 92/18619; WO 93/11236; WO 95/15982; and WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743; and 5,969,108. Also, transgenic mice, or other organisms, including other mammals, may be used to generate humanized antibodies.

Fully human antibodies are those antibodies in which the variable regions and the constant regions (where present) of both the heavy and the light chains are all of human origin, or substantially identical to sequences of human origin, not necessarily from the same antibody. Examples of fully human antibodies may include antibodies produced for example by the phage display methods described above and antibodies produced by mice in which the murine immunoglobulin variable and/or constant region genes have been replaced by their human counterparts eg. as described in general terms in EP0546073 B1, U.S. Pat. No. 5,545,806, U.S. Pat. No. 5,569,825, U.S. Pat. No. 5,625,126, U.S. Pat. No. 5,633,425, U.S. Pat. No. 5,661,016, U.S. Pat. No. 5,770,429, EP 0438474 B1 and EP0463151 B1.

The antibody starting material for use in the present invention may be prepared by the use of recombinant DNA techniques involving the manipulation and re-expression of DNA encoding the antibody variable and constant region(s). Standard molecular biology techniques may be used to modify, add or delete amino acids or domains as desired.

Any alterations to the variable or constant regions are still encompassed by the terms 'variable' and 'constant' regions as used herein.

The antibody starting material may be obtained from any species including for example mouse, rat, rabbit, hamster, camel, llama, goat or human. Parts of the antibody may be obtained from more than one species, for example the antibody may be chimeric. In one example, the constant regions are from one species and the variable regions from another. The antibody starting material may also be modified. In another example, the variable region of the antibody has been created using recombinant DNA engineering techniques. Such engineered versions include those created for example from natural antibody variable regions by insertions, deletions or changes in or to the amino acid sequences of the natural antibodies. Particular examples of this type include those engineered variable region domains containing at least one CDR and, optionally, one or more framework amino acids from one antibody and the remainder of the variable region domain from a second antibody. The methods for creating and manufacturing these antibodies are well known in the art (see for example, Boss et al., U.S. Pat. No. 4,816,397; Cabilly et al., U.S. Pat. No. 6,331,415; Shrader et al., WO 92/02551; Ward et al., 1989, Nature, 341, 544; Orlandi et al., 1989, Proc. Natl. Acad. Sci. USA, 86, 3833; Riechmann et al., 1988, Nature, 322, 323; Bird et al, 1988, Science, 242, 423; Queen et al., U.S. Pat. No. 5,585,089; Adair, WO91/09967; Mountain and Adair, 1992, Biotechnol. Genet. Eng. Rev, 10, 1-142; Verma et al., 1998, Journal of Immunological Methods, 216, 165-181).

In one embodiment the antibody comprises a variable domain pair forming a binding domain is a cognate pair. Cognate pair as employed herein is intended to refer to a natural pair of variable domains, that is to say isolated from a single antibody or antibody expressing cell.

Variable domains may have been optimized and/or humanized.

Optimised/humanized variable domains derived from a cognate pair will still be considered a cognate pair after optimization/humanization.

Thus the invention extends to human, humanized or chimeric molecules.

In one embodiment the molecule specifically binds a target antigen. Specifically binds as employed herein is intended to refer to molecules having high affinity for a target antigen (to which it is specific) and which binds antigens to which it is not specific with a low or much lower affinity (or not at all). Methods of measuring affinity are known to those skilled in the art and include such assays as BIAcore™.

The antibody molecules of the present invention suitably have a high binding affinity, in particular, nanomolar or picomolar. Affinity may be measured using any suitable method known in the art, including BIAcore™. In one embodiment the molecule of the present invention has a binding affinity of about 100 pM or better. In one embodiment the molecule of the present invention has a binding affinity of about 50 pM or better. In one embodiment the molecule of the present invention has a binding affinity of about 40 pM or better. In one embodiment the molecule of the present invention has a binding affinity of about 30 pM or better. In one embodiment the molecule of the present invention is fully human or humanised and has a binding affinity of about 100 pM or better.

A derivative of a naturally occurring domain as employed herein is intended to refer to where one, two, three, four or five amino acids in a naturally occurring sequence have been replaced or deleted, for example to optimize the properties of the domain such as by eliminating undesirable properties but wherein the characterizing feature(s) of the domain is/are retained.

In one embodiment the antibody molecules of the present invention comprise one or more albumin binding peptides. In vivo the peptide binds albumin, which increases the half-life of the molecule.

The albumin binding peptide may be appended from one or more variable regions, a hinge or C-terminal of the molecule or any location that does not interfere with the molecules antigen binding properties.

Examples of albumin binding peptides are provided in WO 2007/106120.

It will also be understood by one skilled in the art that the antibody may undergo a variety of posttranslational modifications. The type and extent of these modifications often depends on the host cell line used to express the molecule as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. *Journal of Chromatography* 705: 129-134, 1995).

If desired a molecule for use in the present invention may be conjugated to one or more effector molecule(s). It will be appreciated that the effector molecule may comprise a single effector molecule or two or more such molecules so linked as to form a single moiety that can be attached to the antibody molecule of the present invention. Where it is desired to obtain an antibody according to the invention linked to an effector molecule, this may be prepared by standard chemical or recombinant DNA procedures in which the antibody is linked either directly or via a coupling agent to the effector molecule. Techniques for conjugating such effector molecules to an antibody are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, *Pharmacology and Therapeutics*, 83, 67-123). Particular chemical procedures include, for example, those described in WO 93/06231, WO 92/22583, WO 89/00195, WO 89/01476 and WO03031581. Alternatively, where the effector molecule is a protein or polypeptide the linkage may be achieved using recombinant DNA procedures, for example as described in WO 86/01533 and EP0392745.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarrnycins), and anti-mitotic agents (e.g. vincristine and vinblastine).

Other effector molecules may include chelated radionuclides such as $^{111}$In and $^{90}$Y, Lu$^{177}$, Bismuth$^{213}$, Californium$^{252}$, Iridium$^{192}$ and Tungsten$^{188}$/Rhenium$^{188}$; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, *pseudomonas* exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO 05/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Specific naturally occurring polymers include lactose, amylose, dextran, glycogen or derivatives thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody of the disclosure and the polymer.

The size of the polymer may be varied as desired, but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Suitable polymers include a polyalkylene polymer, such as a poly(ethyleneglycol) or, especially, a methoxypoly(ethyleneglycol) or a derivative thereof, and especially with a molecular weight in the range from about 15000 Da to about 40000 Da.

In one example an antibody for use in the present invention is attached to poly(ethyleneglycol) (PEG) moieties. In one particular example the PEG molecules may be attached through any available amino acid side-chain or terminal amino acid functional group located in the antibody, for example any free amino, imino, thiol, hydroxyl or carboxyl group. Such amino acids may occur naturally in the antibody or may be engineered into the antibody using recombinant DNA methods (see for example U.S. Pat. No. 5,219,996; U.S. Pat. No. 5,667,425; WO 98/25971). In one example the molecule of the present invention is a modified antibody wherein the modification is the addition to the C-terminal end of its heavy chain one or more amino acids to allow the attachment of an effector molecule. Multiple sites can be used to attach two or more PEG molecules.

In one embodiment a PEG molecule is linked to a cysteine 171 in the light chain, for example see WO2008/038024 incorporated herein by reference.

Suitably PEG molecules are covalently linked through a thiol group of at least one cysteine residue located in the antibody. Each polymer molecule attached to the modified antibody may be covalently linked to the sulphur atom of a cysteine residue located in the antibody. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

The present invention also provides isolated DNA encoding an antibody molecule described herein.

In a further aspect there is provided a vector comprising said DNA.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

In a further aspect there is provided a host cell comprising said vector and/or DNA.

Any suitable host cell/vector system may be used for expression of the DNA sequences encoding the molecule of the present invention. Bacterial, for example E. coli, and other microbial systems may be used or eukaryotic, for example mammalian, host cell expression systems may also be used. Suitable mammalian host cells include CHO, myeloma or hybridoma cells.

The present invention also provides a process for the production of an antibody molecule as described herein comprising culturing a host cell containing a vector (and/or DNA) of the present invention under conditions suitable for leading to expression of protein from DNA encoding an antibody molecule of the present invention, and isolating an antibody molecule.

For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

The antibody molecules according to the present disclosure are expressed at suitable levels from host cells making them conducive to commercial processing.

The antibody may be specific for any target antigen. The antigen may be a cell-associated protein, for example a cell surface protein on cells such as bacterial cells, yeast cells, T-cells, endothelial cells or tumour cells, or it may be a soluble protein. Antigens of interest may also be any medically relevant protein such as those proteins upregulated during disease or infection, for example receptors and/or their corresponding ligands. Particular examples of cell surface proteins include adhesion molecules, for example integrins such as β1 integrins e.g. VLA-4, E-selectin, P selectin or L-selectin, CD2, CD3, CD4, CD5, CD7, CD8, CD11a, CD11b, CD18, CD19, CD20, CD23, CD25, CD33, CD38, CD40, CD40L, CD45, CDW52, CD69, CD134 (OX40), ICOS, BCMP7, CD137, CD27L, CDCP1, CSF1 or CSF1-Receptor, DPCR1, DPCR1, dudulin2, FLJ20584, FLJ40787, HEK2, KIAA0634, KIAA0659, KIAA1246, KIAA1455, LTBP2, LTK, MAL2, MRP2, nectin-like2, NKCC1, PTK7, RAIG1, TCAM1, SC6, BCMP101, BCMP84, BCMP11, DTD, carcinoembryonic antigen (CEA), human milk fat globulin (HMFG1 and 2), MHC Class I and MHC Class II antigens, KDR and VEGF, PD-1, DC-SIGN, TL1A, DR3, IL-7 receptor A and where appropriate, receptors thereof.

Soluble antigens include interleukins such as IL-1, IL-2, EL-3, IL-4, IL-5, IL-6, IL-8, IL-12, IL-13, IL-14, IL-16 or IL-17, such as IL17A and/or IL17F, viral antigens for example respiratory syncytial virus or cytomegalovirus antigens, immunoglobulins, such as IgE, interferons such as interferon α, interferon β or interferon γ, tumour necrosis factor TNF (formerly known as tumour necrosis factor-α and referred to herein as TNF or TNFα), tumor necrosis factor-β, colony stimulating factors such as G-CSF or GM-CSF, and platelet derived growth factors such as PDGF-α, and PDGF-β, WISP-1 and where appropriate receptors thereof. Other antigens include bacterial cell surface antigens, bacterial toxins, viruses such as influenza, EBV, HepA, B and C, bioterrorism agents, radionuclides and heavy metals, and snake and spider venoms and toxins.

In one embodiment, the antibody may be used to functionally alter the activity of the antigen of interest. For example, the antibody may neutralize, antagonize or agonise the activity of said antigen, directly or indirectly.

In one embodiment the present disclosure extends to a method of generating an asymmetric mixed antibody according to the present disclosure comprising the steps of taking a symmetrical antibody (i.e. one where both the heavy chains are the same/identical) comprising a first heavy chain sequence or a fragment thereof as defined herein and mixing the said antibody in vitro with a second symmetrical antibody comprising a second heavy chain sequence or a fragment thereof which is different to said first heavy chain sequence, under conditions conducive to heavy chain exchange between the two antibodies, and optionally isolation of the asymmetric mixed antibody.

In vitro conditions conducive to dynamic exchange include reducing conditions. Suitable reducing agents include GSH, 2-mercaptoethanol, 2-mercaptoethylamine, TBP, TCEP, cysteine-HCl and DTT.

Suitable concentrations of the reducing agents are in the range 0.01 to 10 mM such as 0.5 to 5 mM. In addition, reduction may be achieved using redox buffers, that is to say different relative ratios of oxidised and reduced variants of reagents such as for example: GSH:GSSG and Cys:diCys Suitable conditions include ratios of antibodies are in the range 0.5:5 to 5:05, such as 1:1 or 1:2.

Suitable temperature include 15 to 40° C., such as 37° C.

The reducing conditions may be selected to be between the reductive stabilities of the homodimers and the heterodimers.

In an alternative embodiment the antibodies if the disclosure are prepared employing a mixed cell culture, for example ~50% exchange occurs. This may yield in the region of 1-2 g/l of the desired bispecific.

In one embodiment there is provided an asymmetric antibody obtained or obtainable from a method described herein and a formulation comprising same, in particular for use in treatment.

The antibody molecules of the present invention are useful in the treatment and/or prophylaxis of a pathological condition.

Thus there is provided an antibody according to the present invention for use in treatment, by administering a therapeutically effective amount thereof, for example in a pharmaceutical formulation. In one embodiment the antibody according to the invention is administered topically to the lungs, for example by inhalation.

The antibodies provided by the present invention are useful in the treatment of diseases or disorders including inflammatory diseases and disorders, immune disease and disorders, fibrotic disorders and cancers.

The term "inflammatory disease" or "disorder" and "immune disease or disorder" includes rheumatoid arthritis, psoriatic arthritis, still's disease, Muckle Wells disease, psoriasis, Crohn's disease, ulcerative colitis, SLE (Systemic Lupus Erythematosus), asthma, allergic rhinitis, atopic dermatitis, multiple sclerosis, vasculitis, Type I diabetes mellitus, transplantation and graft-versus-host disease.

The term "fibrotic disorder" includes idiopathic pulmonary fibrosis (IPF), systemic sclerosis (or scleroderma), kidney fibrosis, diabetic nephropathy, IgA nephropathy, hypertension, end-stage renal disease, peritoneal fibrosis (continuous ambulatory peritoneal dialysis), liver cirrhosis, age-related macular degeneration (ARMD), retinopathy, cardiac reactive fibrosis, scarring, keloids, burns, skin ulcers, angioplasty, coronary bypass surgery, arthroplasty and cataract surgery.

The term "cancer" includes a malignant new growth that arises from epithelium, found in skin or, more commonly, the lining of body organs, for example: breast, ovary, prostate, lung, kidney, pancreas, stomach, bladder or bowel. Cancers tend to infiltrate into adjacent tissue and spread (metastasize) to distant organs, for example: to bone, liver, lung or the brain.

The present invention also provides a pharmaceutical or diagnostic composition comprising an antibody of the present invention in combination with one or more of a pharmaceutically acceptable excipient, diluent or carrier. Accordingly, provided is the use of an antibody of the invention for the manufacture of a medicament. The composition will usually be supplied as part of a sterile, pharmaceutical composition that will normally include a pharmaceutically acceptable carrier. A pharmaceutical composition of the present invention may additionally comprise a pharmaceutically-acceptable adjuvant.

The present invention also provides a process for preparation of a pharmaceutical or diagnostic composition comprising adding and mixing the antibody of the present invention together with one or more of a pharmaceutically acceptable excipient, diluent or carrier.

The antibody of the disclosure may be the sole active ingredient in the pharmaceutical or diagnostic composition or may be accompanied by other active ingredients including other antibody ingredients, for example anti-TNF, anti-IL-10, anti-T cell, anti-IFNγ or anti-LPS antibodies, or non-antibody ingredients such as xanthines. Other suitable active ingredients include antibodies capable of inducing tolerance, for example, anti-CD3 or anti-CD4 antibodies.

In a further embodiment the antibody or composition according to the disclosure is employed in combination with a further pharmaceutically active agent, for example a corticosteroid (such as fluticasone propionate) and/or a beta-2-agonist (such as salbutamol, salmeterol or formoterol) or inhibitors of cell growth and proliferation (such as rapamycin, cyclophosphmide, methotrexate) or alternative a CD28 and/or CD40 inhibitor. In one embodiment the inhibitor is a small molecule. In another embodiment the inhibitor is an antibody specific to the target.

The pharmaceutical compositions suitably comprise a therapeutically effective amount of the antibody of the invention. The term "therapeutically effective amount" as used herein refers to an amount of a therapeutic agent needed to treat, ameliorate or prevent a targeted disease or condition, or to exhibit a detectable therapeutic or preventative effect. The therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgment of the clinician. Generally, a therapeutically effective amount will be from 0.01 mg/kg to 50 mg/kg, for example 0.1 mg/kg to 20 mg/kg. Pharmaceutical compositions may be conveniently presented in unit dose forms containing a predetermined amount of an active agent of the invention per dose.

Compositions may be administered individually to a patient or may be administered in combination (e.g. simultaneously, sequentially or separately) with other agents, drugs or hormones.

The dose at which an antibody of the present invention is administered depends on the nature of the condition to be treated, for example the extent of the disease/inflammation present and on whether the molecule is being used prophylactically or to treat an existing condition.

The frequency of dose will depend on the half-life of the antibody and the duration of its effect. If the antibody has a short half-life (e.g. 2 to 10 hours) it may be necessary to give one or more doses per day. Alternatively, if the antibody has a long half-life (e.g. 2 to 15 days) it may only be necessary to give a dosage once per day, once per week or even once every 1 or 2 months.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g. by injection or infusion, for example by bolus injection or continuous infusion.

Where the product is for injection or infusion, it may take the form of a suspension, solution or emulsion in an oily or aqueous vehicle and it may contain formulatory agents, such as suspending, preservative, stabilising and/or dispersing agents. Alternatively, the molecule of the disclosure may be in dry form, for reconstitution before use with an appropriate sterile liquid.

Once formulated, the compositions of the invention can be administered directly to the subject. The subjects to be treated can be animals. However, in one or more embodiments the compositions are adapted for administration to human subjects.

Suitably in formulations according to the present disclosure, the pH of the final formulation is not similar to the value of the isoelectric point of the antibody, for example if the pH of the formulation is 7 then a pI of from 8-9 or above may be appropriate. Whilst not wishing to be bound by theory it is thought that this may ultimately provide a final formulation with improved stability, for example the antibody remains in solution.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be an antibody. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

In one embodiment the formulation is provided as a formulation for topical administrations including inhalation.

Suitable inhalable preparations include inhalable powders, metering aerosols containing propellant gases or inhalable solutions free from propellant gases. Inhalable powders according to the disclosure containing the active substance may consist solely of the abovementioned active substances or of a mixture of the abovementioned active substances with physiologically acceptable excipient.

These inhalable powders may include monosaccharides (e.g. glucose or arabinose), disaccharides (e.g. lactose, saccharose, maltose), oligo- and polysaccharides (e.g. dextrans), polyalcohols (e.g. sorbitol, mannitol, xylitol), salts (e.g. sodium chloride, calcium carbonate) or mixtures of these with one another. Mono- or disaccharides are suitably used, the use of lactose or glucose, particularly but not exclusively in the form of their hydrates.

Particles for deposition in the lung require a particle size less than 10 microns, such as 1-9 microns for example from 0.1 to 5 µm, in particular from 1 to 5 µm. The particle size of the active ingredient (such as the antibody) is of primary importance.

The propellent gases which can be used to prepare the inhalable aerosols are known in the art. Suitable propellent gases are selected from among hydrocarbons such as n-propane, n-butane or isobutane and halohydrocarbons such as chlorinated and/or fluorinated derivatives of methane, ethane, propane, butane, cyclopropane or cyclobutane. The abovementioned propellent gases may be used on their own or in mixtures thereof.

Particularly suitable propellent gases are halogenated alkane derivatives selected from among TG 11, TG 12, TG 134a and TG227. Of the abovementioned halogenated hydrocarbons, TG134a (1,1,1,2-tetrafluoroethane) and TG227 (1,1,1,2,3,3,3-heptafluoropropane) and mixtures thereof are particularly suitable.

The propellent-gas-containing inhalable aerosols may also contain other ingredients such as cosolvents, stabilisers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active ingredient.

Alternatively topical administrations to the lung may also be by administration of a liquid solution or suspension formulation, for example employing a device such as a nebulizer, for example, a nebulizer connected to a compressor (e.g., the Pari LC-Jet Plus® nebulizer connected to a Pari Master® compressor manufactured by Pari Respiratory Equipment, Inc., Richmond, Va.).

The antibody of the invention can be delivered dispersed in a solvent, e.g., in the form of a solution or a suspension. It can be suspended in an appropriate physiological solution, e.g., saline or other pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 mL of water so as to achieve a pH of about 4.0 to 5.0. A suspension can employ, for example, lyophilised molecule.

The therapeutic suspensions or solution formulations can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent/solution used for the for the formulation, aseptic suspension of the molecule in the sterile buffered solvent solution, and dispensing of the formulation into sterile receptacles by methods familiar to those of ordinary skill in the art.

Nebulizable formulation according to the present disclosure may be provided, for example, as single dose units (e.g., sealed plastic containers or vials) packed in foil envelopes. Each vial contains a unit dose in a volume, e.g., 2 mL, of solvent/solution buffer.

The antibody of the present disclosure are thought to be particularly suitable for delivery via nebulisation.

Comprising in the context of the present specification is intended to meaning including.

Where technically appropriate embodiments of the invention may be combined.

"Asymmetric" and "asymmetric mixed" are employed interchangeably herein.

The invention will now be described with reference to the following examples, which are merely illustrative and should not in any way be construed as limiting the scope of the present invention.

EXAMPLES

1 Mutagenesis of IgG4 Heavy Chain and Generation of Mutated IgG4 Heavy Chain Single Gene Vectors.

Amino acid mutations were performed using the Quickchange® Lightening Multi Site Directed Mutagenesis (SDM) kit or the Quickchange® DSM kit (obtained from Stratagene®) (catalogue numbers 210516 and 200521 respectively) and performed according to manufacturer's instructions.

Mutations were verified by DNA sequencing. The IgG4 heavy chains of antibodies 1 to 47 in the following table were produced:

| Antibody Number | Heavy Chain Mutations (Kabat Numbering) | $C_H1$ domain & Hinge SEQ ID NO: | $C_H1$, Hinge, $C_H2$ & $C_H3$ SEQ ID NO: |
|---|---|---|---|
| 1 | C127S | 296 | 306 |
| 2 | C127S, C239S | 33 | 59 |
| 3 | C127S, C242S | 34 | 60 |
| 4 | C127S, C242S, C239S | 297 | 307 |
| 5 | G230C | 298 | 308 |
| 5P | G230C, S241P | 299 | 309 |
| 6 | C127S, G230C, C239S | 12 | 38 |
| 7 | C127S, G230C, C242S | 13 | 39 |
| 8 | C127S, G230C, C239S, C242S | 14 | 40 |
| 9 | G230C, C239S | 300 | 310 |
| 10 | G230C, C242S | 301 | 311 |
| 11 | G230C, C239S, C242S | 302 | 312 |
| 12 | C239S | 303 | 313 |
| 13 | C242S | 304 | 314 |
| 15 | C127S, G230C | 15 | 41 |
| 16 | C127S, G230C, S241P | 16 | 42 |

-continued

| Antibody Number | Heavy Chain Mutations (Kabat Numbering) | $C_H1$ domain & Hinge SEQ ID NO: | $C_H1$, Hinge, $C_H2$ & $C_H3$ SEQ ID NO: |
|---|---|---|---|
| 17 | Human IgG4 wild type | 2 | — |
| 18 | S241P | — | — |
| 19 | Human IgG1 wild type | 1 | — |
| 28 | C127S Y229C | 17 | 43 |
| 28P | C127S Y229C, S241P | 36 | 62 |
| 29 | C127S Y229C C239S | 18 | 44 |
| 30 | C127S Y229C C242S | 19 | 45 |
| 31 | C127S Y229C C239S C242S | 20 | 46 |
| 32 | C127S K228C | 21 | 47 |
| 33 | C127S K228C C239S | 22 | 48 |
| 34 | C127S K228C C242S | 23 | 49 |
| 35 | C127S K228C C239S C242S | 24 | 50 |
| 36 | C127S S227C | 25 | 51 |
| 37 | C127S S227C C239S | 26 | 52 |
| 38 | C127S S227C C242S | 27 | 53 |
| 39 | C127S S227C C239S C242S | 28 | 54 |
| 44 | C127S G230C P238PAAA | 29 | 55 |
| 44P | C127S G230C P238PAAA, S241P | 37 | 63 |
| 45 | C127S G230C P238PAAA C239S | 30 | 56 |
| 46 | C127S G230C P238PAAA C242S | 31 | 57 |
| 47 | C127S G230C P238PAAA C239S C242S | 32 | 58 |
| 48 | C127S, S227P, Y229S, G230C, P237D, P238KTHT, S241P | 35 | 61 |
| 49 | C127S G230C P238PA | | |
| 50 | C127S G230C P238PAA S241P | | |
| 51 | C127S, G230C, P238PAAAA | | |
| 52 | C127S, G230C, P238PAAAAA | | |
| 55 | C127S, G230C, P238PTHT | | |
| 56 | C127S, G230C, P237D, P238KTHT | | |
| 57 | C127S, G230C, P238PGGG | | |
| 60 | C127S, S227P, G230C | | |
| 62 | C127S, Y229S, G230C | | |
| 64 | C127S, S227P, Y229S, G230C | | |
| 65 | C127S, S227P, Y229S, G230C, P237D, P238KTHT | | |
| 66 | C127S, G230C, P237D, P238KTH | | |
| 67 | C127S, G230C, P237D, P238KT | | |
| 68 | C127S, G230C, P237D, P238K | | |
| 69 | C127S, G230C P237D, P238KAAA | | |
| 71 | C127S, S227P, G230C, P237D, P238KTHT | | |
| 73 | C127S, Y229S, G230C, P237D, P238KTHT | | |

Other antibodies prepared are described in the table above.

The heavy chain of antibody 48 (Sequence ID NO: 266) was generated by PCR and restriction enzyme cloning. The PCR product was generated by a forward oligo encoding the IgG1 upper and core hinge region sequence and a restriction site BglII and a reverse oligo encoding the restriction enzyme DraIII. The PCR fragment was then digested with above mentioned enzymes and ligated into the hG4 single gene vector containing the appropriate variable region.

2. Expression of the Mutated IgG4 Antibodies

All mutant DNA was transfected into CHOK1 cells. Cells ($2\times10^8$ cells/ml) were resuspended in 1 ml Earles Balance Salt Solution (Sigma) and mixed with 400 µg of DNA (200 µg heavy chain DNA and 200 µg kappa light chain DNA). 800 µl aliquots were transferred to 0.4 cm cuvettes (Biorad). For a 500 ml culture, six cuvettes were electroporated under the following parameters: 1 ms, 9.6 Amps; 10 ms, 0 Amps; 40 ms, 3.2 Amps. The transfected cells were incubated for 24 hrs, shaking at 140 rpm in a 5% $CO_2$ humidified environment at 37° C. and continued from day 2 post transfection at 32° C. for 10-13 days. On day 4 post transfection 1.6 mls 1 M sodium butyrate was added to the culture. Once the cells reached 40% viability or up to day 13, the supernatant was harvested. Cultures were centrifuged for 45 minutes at 4000 rpm. The supernatant was put through a 0.22 µM Stericup filter (Millipore) to be purified.

3. Purification of Mutated IgG4 Antibodies

Supernatants (200-500 ml) were purified using a Protein A 5 ml HiTrap Mab Select SuRe column (GE Healthcare, Amersham UK). Samples were prepared by adding $\frac{1}{50}^{th}$ of the supernatant volume of 2 M Tris-HCl pH 8.5. Samples were loaded onto the column at 1 ml/min. The column was washed with PBS pH 7.4. To elute the samples, 0.1 M sodium citrate, pH 3.4 was run through the column at 1 ml/min and 0.5 ml fractions were collected. Peak fractions were neutralised by adding 0.125 ml of 2 M Tris-HCl pH8.5 to each. UV detection was set at 280 nm.

4. Characterization of Purified Mutated IgG4 Antibodies

SDS PAGE Analysis:

Crude supernatant was centrifuged at 1200 rpm for 5 mins and quantified on the OCTET. Antibody samples (25-30 ng) were prepared by adding the appropriate amounts of antibody, 4× Loading Buffer (Invitrogen) and 2 µl 100 mM NEM. A total volume of 20 µl was made up using $dH_2O$. The samples were then boiled for 3 mins at 100° C. and loaded onto a 15 well 1.5 mm 4-20% Tris-Glycine gel. Gels were run at 150 V for 1.5 hrs in 1× Tank buffer. Antibodies were transferred to a nitrocellulose membrane using the iBlot dry transfer system set to transfer for 8 mins. The membrane was incubated for 1 hr at room temperature (RT) in PBS-TM on a shaking platform, followed by incubation with a rabbit anti-human IgG Fc HRP conjugated antibody (Jackson Immunoresearch) or goat anti-human Kappa light chain HRP conjugated antibody (Bethyl) for 1 hr, shaking at RT. This was followed by 3 washes of 5 mins each with PBS-T. The blots were revealed using a metal enhanced DAB substrate kit according to the manufacturer's instructions (Pierce).

The results of the immuno-blot analysis is shown in FIGS. 7, 8, 9 and 10. In FIG. 7-10, H stands for heavy chain and L for light chain, H2L2 is a whole antibody molecule comprising two heavy chains and two light chains and HL is a half molecule comprising one heavy chain and one light chain.

FIG. 7 shows the immuno-blot analysis for antibodies 15, 16, 6, 7, 8, 17, 18, 19, 5, 5P, 9, 10, 11, 1, 2, 3, 4, 12, 13 and 14. It can be seen from FIG. 7 that the antibodies show a good level of H2L2 except for antibodies 4, 8 and 14 which show no or very little H2L2 due to the presence of both hinge mutations C239S and C242S. However, antibodies 4, 8 and 14 can form H2L2 by non-covalent bonding between the heavy chains. Mutant 3 also shows little H2L2, this mutant retains C239 but is unable to form inter heavy chain disulphides in the hinge, presumably due to efficient formation of a disulphide between the C-terminal light chain (LC) cysteine and the hinge C239. It can also be seen that antibodies which comprise the mutation C239S but not C242S (antibodies 2, 6, 9 and 12) show reduced formation of HL compared to antibodies which comprise neither C239S nor C242S or antibodies which comprise C242S but not C239S. Antibodies 5P and 16 which comprise the S241P mutation also show reduced formation of HL. A comparison of mutants 2 and 3 shows the extent of the 'reach' of the C-terminal cysteine of light chain to form a disulphide bond with the heavy chain, it appears that the light chain cysteine bonds more efficiently to C239 than to C242 in the heavy chain.

FIG. 8 shows the immuno-blot analysis for antibodies 15, 6, 7, 8, 28, 29, 30, 31, 17, 19, 32, 33, 33, 34, 35, 36, 37, 38 and 39. It can be seen from FIG. 8 that the antibodies show a good level of H2L2 except for antibodies 8, 31, 35 and 39 which show no or very little H2L2 due to the presence of mutations C239S and C242S in the hinge region and therefore no disulphide bonds form between two heavy chains. However, antibodies 8, 31, 35 and 39 can form H2L2 by non-covalent bonding between the heavy chains. It can also be seen that antibodies which comprise the mutation C239S but not C242S (antibodies 6, 29, 33 and 37) show reduced formation of HL compared to antibodies which comprise neither C239S nor C242S or antibodies which comprise C242S but not C239S. Mutant 15 is able to form a disulphide bond between the light chain and G230C in the $C_H1$ and inter heavy chain disulphides hence resulting in a fully assembled and disulphide bonded protein. Furthermore, a comparison of mutants 15(C127S G230C), 28(C127S Y229C), 32(C127S K228C) and 36(C127S S227C) shows that the position of the introduced cysteine in the upper hinge improves inter LC-HC disulphide bond formation. G230 and Y229 are particularly preferred positions to introduce a cysteine. Mutant 28 (C127S Y229C) shows a low level of HL and H2 and therefore has low disulphide bond heterogeneity.

FIG. 9 shows the immuno-blot analysis for antibodies 15, 6, 7, 8, 44, 45, 46, 47, 17 and 19. It can be seen from FIG. 9 that the antibodies show a good level of H2L2 except for antibodies 8 and 47 which show no or very little H2L2 due to the presence of mutations C239S and C242S in the hinge region and therefore no disulphide bonds form between two heavy chains. However, antibodies 8 and 47 can form H2L2 by non-covalent bonding between the heavy chains. It can also be seen that antibodies which comprise the mutation C239S but not C242S (antibodies 6 and 45) show reduced formation of HL compared to antibodies which comprise neither C239S nor C242S or antibodies which comprise C242S but not C239S. In particular, mutant 44 shows that insertion of three amino acids in the upper hinge can also reduce the formation of HL and H2 and hence has lower levels of disulphide heterogeneity than the comparable mutant 15.

FIG. 10, shows the immuno-blot analysis for antibodies 48, 17, 18 and 19. It can be seen from FIG. 10, that antibody 48 shows a good level of H2L2 and very little HL. Mutant 48 contains the IgG1 upper hinge sequence EPKSCDKTHT SEQ ID NO: 319 in place of the IgG4 upper hinge sequence along with a core hinge S241P mutation. Hence mutant 48 has the upper and core hinge sequence EPKSCDKTHTCP-PCP SEQ ID NO: 320, Mutant 48 shows lower levels of disulphide bond heterogeneity compared to the wild type IgG4 antibody 17 and approximately equivalent low levels of disulphide bond heterogeneity compared to the IgG4 S241P mutant 18 and wild type IgG1 antibody 19.

Thermofluor Assay:

Thermostabilities of purified mAbs were analyzed in a thermofluor assay using SYPRO® Orange to monitor the thermal unfolding process of proteins. 5 µl of mAb at 1 mg/ml, 5 µl of 30×dye, and 40 µl of PBS were added together. Ten µl of the mix was dispensed in quadruplicate to a 384 PCR optical well plate and was run on the 7900HT Fast Real-Time PCR System (Agilent Technologies UK Ltd, Wokingham UK). This PCR System contains a heating device for accurate temperature control set at 20° C. to 99° C.; a charged coupled device simultaneously monitors the fluorescence changes in the wells.

FIGS. 11, 12, 13, 14 and 15 show the results of the thermostability analysis of the IgG4 Antibody mutants compared to wild-type IgG1 and IgG4 antibodies.

A comparison of mutant 15 with wild type IgG4 (mutant 17) shows and increase in the Fab Tm due to the altered disulphide arrangement. A comparison of mutant 15 and 28 shows further improvement in Fab Tm for mutant 28 comprising Y229C mutation compared to mutant 15 comprising G230C mutation. A comparison of mutant 15 and 44 shows that the Fab Tm of a G230C mutant can be further increased further by insertion of three amino acids in the upper hinge. Comparison of mutants 17 and 18 show that the S241P middle hinge mutation does not increase Fab Tm even though it significantly reduces HL formation. Mutant 48 also shows significantly improved Fab Tm when compared to both wild type IgG4 (mutant 17) and mutant 15.

FIG. 15 shows the overall ranking of the thermostabilites of selected IgG4 mutants according to the present invention. Mutants 48, 44, 44P, 46, 45, 6, 29, 30, 28, 28P, 31, 8, 47 and 15 all show significantly higher Fab Tm values compared to the wild type IgG4 (mutant 17) and wild type IgG4 S241P (mutant 18).

5. Fab Arm Exchange a) In Vitro Heavy Chain Exchange

A first IgG4 antibody and a second IgG4 antibody, each having different antigen specifities, were mixed in a 1:2 molar ratio at a total concentration of 100 ug/ml in phosphate buffered saline (PBS) (in mM: 150 NaCl, 10

NaH$_2$PO$_4$; pH 7.4). To allow disulphide bond reduction, samples were supplemented with reduced Glutathione (GSH; Sigma) to a final concentration of 0, 0.5 or 5 mM. At the start of the experiment (t=0 hours) an aliquot of the mixture was taken, quenched with N-ethylmaleimide (NEM; Sigma) to a final concentration of 10 mM (to inactivate potentially reactive thiol groups) and incubated alongside the rest of the mixture for 16 hours at 37° C. (t=16 hours). After incubation, the t=16 hours sample was quenched as above. The combinations of first and second antibodies tested are shown in the following table:

| Antibody 1 | Antibody 1 (Mutations compared to wild type IgG4) | Antibody 2 |
|---|---|---|
| IgG1 wt (wild type) | — | IgG4 wt (wild type) |
| IgG4 wt (wild type) | — | IgG4 wt (wild type) |
| IgG4 P | S241P | IgG4 wt (wild type) |
| IgG4 mutant 28 | C127S Y229C | IgG4 wt (wild type) |
| IgG4 mutant 28 P | C127S Y229C S241P | IgG4 wt (wild type) |
| IgG4 mutant 44 | C127S G230C P238PAAA | IgG4 wt (wild type) |
| IgG4 mutant 44P | C127S G230C P238PAAA, S241P | IgG4 wt (wild type) |
| IgG4 mutant 48 | C127S, S227P, Y229S, G230C, P237D, P238KTHT, S241P | IgG4 wt (wild type) |
| IgG4 mutant 65 | C127S, S227P, Y229S, G230C, P237D, P238KTHT | IgG4 wt (wild type) |
| IgG4 | IgG4 wild type (S241) | S241G |
| IgG4 | | S241A |
| IgG4 | | S241T |
| IgG4 | | S241P |
| IgG4 | | C127C and Y229C |
| IgG4 | IgG4 S241G | S241A |
| IgG4 | | S241T |
| IgG4 | IgG4 S241T | S241A |
| IgG4 | IgG4 wild type (S241) | C239S |
| IgG4 | | C242S |
| IgG4 | | C239C and C242C |
| IgG4 | | C127C and Y229C |
| IgG4 | IgG4 S241P | C127C and Y229C |
| IgG4 | | S241G |
| IgG4 | | S241A |
| IgG4 | | S241T |
| IgG4 | | C239C and C242C |
| IgG4 | IgG4 C127S and Y229C | S241G |
| IgG4 | | S241A |
| IgG4 | | S241T |
| IgG4 | | C239C and C242C |
| IgG4 | IgG4 C239C and C242C | S241G |
| IgG4 | | S241A |
| IgG4 | | S241T |
| IgG4 | | C239C and C242C |
| IgG4 | | C239S |
| IgG4 | | C242S |

The exchange of heavy chains between antibody 1 and 2 in the table above provides asymmetric antibodies with a heavy chain from each of the relevant antibodies.

b) Detection and Quantification of Heavy Chain Exchange In Vitro

The presence of functionally active bispecific antibodies was determined using a sandwich MSD assay in which quenched reaction samples provided in Example 5 a), serially diluted in 1% BSA in PBS (PB), were pre-incubated with 1 ug/ml biotinylated-antigen 1 (antigen of first antibody) in PB for 1 h at RT with agitation (200 r.p.m) before being transferred to PB pre-blocked streptavidin coated MSD plates (Meso Scale Diagnostics). After 1 h incubation at RT with agitation, wells were washed three times with PBS/0.1% Tween-20 before being incubated with 1 ug/ml of sulfo-tagged antigen 2 (antigen of second antibody) in PB. After incubation, plates were washed as above and signals revealed and measured using the manufactures read buffer and Image Sector 6000 instrument, respectively. Background values obtained from control parallel reactions in which biotinylated-antigen was substituted for a non-biotinylated alternative, were subtracted from all signals. Duplicate values from at least 3 independent experiments were used in all calculations. The higher the MSD signal the larger the amount of heavy chain exchange that has occurred.

FIG. 16 shows heavy chain exchange at 16 hours wherein the first antibody is selected from IgG1 wild-type, IgG4 wild-type and various mutant antibodies and the second antibody is IgG4 wild-type at two concentrations of GSH. The figures show that the mutants have less exchange than the wild-type IgG4 antibodies and significantly greater exchange than the IgG1 wild-type antibody. This is advantageous in that the exchange can be used to prepare the asymmetric antibodies of the present disclosure in vitro, which in vivo have less susceptibility to undergo exchange than wild type IgG4 antibodies. In some instances increasing the concentration of the reducing agent, such as GSH increases the amount of exchange observed.

In good agreement with the literature (Labrijn 2011, Lewis 2009, Stubenrauch 2010, Labrijn 2009) we show that the S241P mutation in the IgG4 core-hinge represents a tool for preventing Fab-arm exchange (FIG. 16). It can also be seen that mutant bispecific antibodies of the present invention would demonstrate less Fab arm exchange than has been shown at 0.5 mM GSH, which is 100 times higher than the 4-6 uM physiological GSH concentration of plasma (Zilmer. et al, 2005. Drug Design Reviews). Accordingly, bispecific antibodies may be created in vitro by Fab arm exchange under reducing conditions, which would then have significantly reduced Fab arm exchange in vivo compared to IgG4 wt.

FIG. 17 shows that a glycine at position 241 can readily exchange with IgG4 mutants with either an alanine or threonine at this position. An IgG4 with an alanine at position 241 will exchange somewhat more with a mutant with a threonine at this position than a mutant with a glycine at this position. Similarly an IgG4 mutant with a Threonine at position 241 showed reduced exchanged activity if in a reaction with S241G compared to a symmetric assay. Exchange with IgG4 S241A was similar to the symmetric assay. In summary, this suggests that IgG4 S241T exchanges at similar levels to IgG4 WT and is more likely to exchange compared to mutants S241A and S241G.

Antibody Affinity:

The affinity of selected mutant IgG4 antibodies of the present invention to the target soluble cytokine may be measured by BIAiacore™. The assay format is capture of the IgG's on an anti-Fc surface followed by titration of soluble cytokine.

The term "$k_d$" ($s^{-1}$), refers to the dissociation rate constant of the antibody-antigen interaction. Said value is also referred to as the $k_{off}$ value.

The term "$k_a$" ($M^4$ $s^4$), as used herein, refers to the association rate constant of the antibody-antigen interaction.

The term "$K_D$" (M) or "$K_D$" (pM), as used herein, refers to the dissociation equilibrium constant of the antibody-antigen interaction.

Size Exclusion (SEC) HPLC Analysis:

Approximately 50 ug purified antibody was run on the HPLC using a S200 column. Abs 1 to 19 were used for the analysis. This result shows that non-covalently associated H2L2 is formed despite alterations to the DSB arrangements of a human IgG4 molecule.

The invention claimed is:

1. An asymmetric antibody of the class IgG4, comprising (a) a first heavy chain paired to a first light chain and (b) a second heavy chain paired to a second light chain, wherein each of the first and second heavy chains comprises a variable region, and a constant region with a hinge region, and a $C_H1$ domain, wherein in the first heavy chain
  (a) an inter-chain cysteine at position 127 is substituted with serine, threonine, alanine, or glycine; and
  (b) an amino acid at position 227, 228, 229 or 230 is substituted with cysteine, and
wherein the second heavy chain is IgG4 wild type or a mutated IgG4 wild type with an S241P mutation, and wherein amino acid numbering is according to the Kabat numbering system.

2. The antibody according to claim 1, wherein the glycine at position 230 of the first heavy chain is substituted with cysteine.

3. The antibody according to claim 1, wherein the tyrosine at position 229 of the first heavy chain is substituted with cysteine.

4. The antibody according to claim 1, wherein the lysine at position 228 of the first heavy chain is substituted with cysteine.

5. The antibody according to claim 1, wherein the serine at position 227 of the first heavy chain is substituted with cysteine.

6. The antibody according to claim 1, wherein the cysteine at position 239 and the cysteine at position 242 of the first heavy chain are substituted with serine, threonine, alanine, or glycine.

7. The antibody according to claim 1, wherein the cysteine at position 239 of the first heavy chain is substituted with serine, threonine, alanine, or glycine.

8. The antibody according to claim 1, wherein the cysteine at position 242 of the first heavy chain is substituted with serine, threonine, alanine, or glycine.

9. The antibody according to claim 6, wherein the cysteine at position 239 and/or the cysteine at position 242 of the first heavy chain is substituted with serine.

10. The antibody according to claim 1, wherein three alanines are inserted between positions 238 and 239 of the first heavy chain.

11. The antibody according to claim 1, wherein a threonine-histidine-threonine amino acid sequence is inserted between positions 238 and 239 of the first heavy chain.

12. The antibody according to claim 1, wherein the second heavy chain is a mutated IgG4 wild type in which the serine at position 241 is substituted with proline.

13. The antibody according to claim 1, wherein in the first heavy chain the glycine at position 230 is substituted with cysteine, the serine at position 227 is substituted with proline, the tyrosine at position 229 is substituted with serine, the proline at position 237 is substituted with aspartic acid, the proline at position 238 is substituted with lysine, the amino acid sequence threonine-histidine-threonine is inserted between positions 238 and 239 and the serine at position 241 is substituted with proline.

14. The antibody according to claim 1, wherein the two variable regions of the heavy chains are identical.

15. The antibody according to claim 1, wherein the amino acid sequences of the two heavy chain variable regions are not identical.

16. The antibody according to claim 1, wherein the antibody is bi-specific.

17. The antibody according to claim 1, wherein one or both heavy chains comprises an upper hinge region and a core region of 12 to 17 amino acids in length.

18. An asymmetric antibody of the class IgG4, comprising first heavy chain paired to a first light chain and a second heavy chain each paired to a second light chain, wherein each of the first and second heavy chains comprises a variable region, a constant region with a hinge region, and a $C_H1$ domain, wherein in the first heavy chain
  (a) an inter-chain cysteine at position 127 is substituted with serine, threonine, alanine, or glycine; and
  (b) the cysteine at position 239 or cysteine at position 242 is substituted with serine, threonine, alanine, or glycine;
wherein the second heavy chain is an IgG4 wild type or a mutated IgG4 wild type with an S241P mutation, and wherein amino acid numbering is according to the Kabat numbering system.

19. An IgG4 antibody, the improvement comprising
  (a) a first heavy chain paired to a first light chain and a second heavy chain paired to a second light chain, wherein the amino acid sequences of the first and second heavy chains are not identical in the regions outside the variable regions, and
  (b) in the first heavy chain
    (i) an inter-chain cysteine at position 127 is substituted with serine, threonine, alanine, or glycine;
    (ii) an amino acid at position 227, 228, 229 or 230 is substituted with cysteine, and
    (iii) the amino acid at position 242 is substituted with serine, threonine, alanine, or glycine,
wherein amino acid numbering is according to the Kabat numbering system, and the IgG4 antibody has improved stability compared to the corresponding wild-type IgG4 antibody.

20. The antibody according to claim 19, wherein the glycine at position 230 of the first heavy chain is substituted with cysteine.

21. The antibody according to claim 19, wherein the tyrosine at position 229 of the first heavy chain is substituted with cysteine.

22. The antibody according to claim 19, wherein the lysine at position 228 of the first heavy chain is substituted with cysteine.

23. The antibody according to claim 19, wherein the serine at position 227 of the first heavy chain is substituted with cysteine.

24. The antibody according to claim 19, wherein the cysteine at position 239 of the first heavy chain is substituted with serine, threonine, alanine, or glycine.

25. The antibody according to claim 19, wherein the cysteine at position 239 and/or the cysteine at position 242 of the first heavy chain is substituted with serine.

26. The antibody according to claim 19, wherein three alanines are inserted between positions 238 and 239 of the first heavy chain.

27. The antibody according to claim 19, wherein a threonine-histidine-threonine sequence is inserted between positions 238 and 239 of the first heavy chain.

28. The antibody according to claim 19, wherein the serine at position 241 of the first heavy chain is substituted with proline.

29. The antibody according to claim 19, wherein in the first heavy chain the glycine at position 230 is substituted with cysteine, the serine at position 227 is substituted with proline, the tyrosine at position 229 is substituted with serine, the proline at position 237 is substituted with aspartic acid, the proline at position 238 is substituted with lysine, the amino acid sequence threonine-histidine-threonine is inserted between positions 238 and 239 and the serine at position 241 is substituted with proline.

30. The antibody according to claim 19, wherein the two variable regions of the heavy chains are identical.

31. The antibody according to claim 19, wherein the amino acid sequences of the two variable regions of the heavy chains are not identical.

32. The antibody according to claim 19, wherein the antibody is bi-specific.

33. The antibody according to claim 19, wherein the hinge regions of the heavy chains are different.

34. The antibody according to claim 19, wherein the hinge regions of the heavy chains are the same.

35. The antibody according to claim 19, wherein one or both heavy chains comprises an upper hinge region and a core region of 12 to 17 amino acids in length.

36. An expression vector, comprising a sequence encoding an antibody of claim 1.

37. A host cell, comprising a vector as defined in claim 36.

* * * * *

SEQUENCE LISTING

<160> NUMBER OF SEQ ID NOS: 322

<210> SEQ ID NO 1
<211> LENGTH: 120
<212> TYPE: PRT
<213> ORGANISM: Artificial Sequence
<220> FEATURE:
<223> OTHER INFORMATION: IgG1 wild type CH1 & hinge
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 1

```
Xaa Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Xaa Pro Lys Ser Cys Asp Lys Thr His Thr Cys Pro Pro Cys
            100                 105                 110

Pro Ala Pro Glu Leu Gly Gly Pro
            115                 120
```

<210> SEQ ID NO 2
<211> LENGTH: 118
<212> TYPE: PRT
<213> ORGANISM: Artificial Sequence
<220> FEATURE:
<223> OTHER INFORMATION: IgG4 wild type CH1 & hinge
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 2

```
Xaa Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95
```

```
Arg Val Xaa Ser Lys Tyr Gly Pro Pro Cys Pro Ser Cys Pro Ala Pro
            100                 105                 110

Glu Phe Leu Gly Gly Pro
        115

<210> SEQ ID NO 3
<211> LENGTH: 6
<212> TYPE: PRT
<213> ORGANISM: Artificial Sequence
<220> FEATURE:
<223> OTHER INFORMATION: human wild-type kappa light chain

<400> SEQUENCE: 3

Phe Asn Arg Gly Glu Cys
1               5

<210> SEQ ID NO 4
<211> LENGTH: 9
<212> TYPE: PRT
<213> ORGANISM: Artificial Sequence
<220> FEATURE:
<223> OTHER INFORMATION: N-terminal sequence of the CH1 domain of a
      human IgG1

<400> SEQUENCE: 4

Leu Ala Pro Ser Ser Lys Ser Thr Ser
1               5

<210> SEQ ID NO 5
<211> LENGTH: 23
<212> TYPE: PRT
<213> ORGANISM: Artificial Sequence
<220> FEATURE:
<223> OTHER INFORMATION: hinge region of a human IgG1

<400> SEQUENCE: 5

Glu Pro Lys Ser Cys Asp Lys Thr His Thr Cys Pro Pro Cys Pro Ala
1               5                   10                  15

Pro Glu Leu Leu Gly Gly Pro
            20

<210> SEQ ID NO 6
<211> LENGTH: 9
<212> TYPE: PRT
<213> ORGANISM: Artificial Sequence
<220> FEATURE:
<223> OTHER INFORMATION: N-terminal sequence of the CH1 domain of a
      human IgG2

<400> SEQUENCE: 6

Leu Ala Pro Cys Ser Arg Ser Thr Ser
1               5

<210> SEQ ID NO 7
<211> LENGTH: 19
<212> TYPE: PRT
<213> ORGANISM: Artificial Sequence
<220> FEATURE:
<223> OTHER INFORMATION: hinge region of a human IgG2

<400> SEQUENCE: 7

Glu Arg Lys Cys Cys Val Glu Cys Pro Pro Cys Pro Ala Pro Pro Val
1               5                   10                  15

Ala Gly Pro
```

<210> SEQ ID NO 8
<211> LENGTH: 9
<212> TYPE: PRT
<213> ORGANISM: Artificial Sequence
<220> FEATURE:
<223> OTHER INFORMATION: N-terminal sequence of the CH1 domain of a
      human IgG3

<400> SEQUENCE: 8

Leu Ala Pro Cys Ser Arg Ser Thr Ser
1               5

<210> SEQ ID NO 9
<211> LENGTH: 40
<212> TYPE: PRT
<213> ORGANISM: Artificial Sequence
<220> FEATURE:
<223> OTHER INFORMATION: hinge region of a human IgG3 antibody

<400> SEQUENCE: 9

Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
            20                  25                  30

Ala Pro Glu Leu Leu Gly Gly Pro
        35                  40

<210> SEQ ID NO 10
<211> LENGTH: 9
<212> TYPE: PRT
<213> ORGANISM: Artificial Sequence
<220> FEATURE:
<223> OTHER INFORMATION: N-terminal sequence of the CH1 domain of a
      human IgG4

<400> SEQUENCE: 10

Leu Ala Pro Cys Ser Arg Ser Thr Ser
1               5

<210> SEQ ID NO 11
<211> LENGTH: 20
<212> TYPE: PRT
<213> ORGANISM: Artificial Sequence
<220> FEATURE:
<223> OTHER INFORMATION: hinge region of a human IgG4

<400> SEQUENCE: 11

Glu Ser Lys Tyr Gly Pro Pro Cys Pro Ser Cys Pro Ala Pro Glu Phe
1               5                   10                  15

Leu Gly Gly Pro
            20

<210> SEQ ID NO 12
<211> LENGTH: 118
<212> TYPE: PRT
<213> ORGANISM: Artificial Sequence
<220> FEATURE:
<223> OTHER INFORMATION: CH1 domain and hinge region sequences of Ab 6
<220> FEATURE:
<221> NAME/KEY: MISC_FEATURE
<222> LOCATION: (1)..(1)
<223> OTHER INFORMATION: Xaa is absent or A

<400> SEQUENCE: 12

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Cys Pro Pro Ser Pro Ser Cys Pro Ala Pro
            100                 105                 110

Glu Phe Leu Gly Gly Pro
        115

<210> SEQ ID NO 13
<211> LENGTH: 118
<212> TYPE: PRT
<213> ORGANISM: Artificial Sequence
<220> FEATURE:
<223> OTHER INFORMATION: CH1 domain and hinge region sequences of Ab 7
<220> FEATURE:
<221> NAME/KEY: MISC_FEATURE
<222> LOCATION: (1)..(1)
<223> OTHER INFORMATION: Xaa is absent or A

<400> SEQUENCE: 13

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Cys Pro Pro Cys Pro Ser Ser Pro Ala Pro
            100                 105                 110

Glu Phe Leu Gly Gly Pro
        115

<210> SEQ ID NO 14
<211> LENGTH: 118
<212> TYPE: PRT
<213> ORGANISM: Artificial Sequence
<220> FEATURE:
<223> OTHER INFORMATION: CH1 domain and hinge region sequences of Ab 8
<220> FEATURE:
<221> NAME/KEY: MISC_FEATURE
<222> LOCATION: (1)..(1)
<223> OTHER INFORMATION: Xaa is absent or A

<400> SEQUENCE: 14

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Cys Pro Pro Ser Pro Ser Ser Pro Ala Pro
            100                 105                 110

Glu Phe Leu Gly Gly Pro
            115

<210> SEQ ID NO 15
<211> LENGTH: 118
<212> TYPE: PRT
<213> ORGANISM: Artificial Sequence
<220> FEATURE:
<223> OTHER INFORMATION: CH1 domain and hinge region sequences of
      antibodies 15
<220> FEATURE:
<221> NAME/KEY: MISC_FEATURE
<222> LOCATION: (1)..(1)
<223> OTHER INFORMATION: Xaa is absent or A

<400> SEQUENCE: 15

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Cys Pro Pro Cys Pro Ser Cys Pro Ala Pro
            100                 105                 110

Glu Phe Leu Gly Gly Pro
            115

<210> SEQ ID NO 16
<211> LENGTH: 118
<212> TYPE: PRT
<213> ORGANISM: Artificial Sequence
<220> FEATURE:
<223> OTHER INFORMATION: CH1 domain and hinge region sequences of
      antibodies 16
<220> FEATURE:
<221> NAME/KEY: MISC_FEATURE
<222> LOCATION: (1)..(1)
<223> OTHER INFORMATION: Xaa is absent or A

<400> SEQUENCE: 16

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Cys Pro Pro Cys Pro Cys Pro Ala Pro
             100                 105                 110

Glu Phe Leu Gly Gly Pro
        115

<210> SEQ ID NO 17
<211> LENGTH: 118
<212> TYPE: PRT
<213> ORGANISM: Artificial Sequence
<220> FEATURE:
<223> OTHER INFORMATION: CH1 domain and hinge region sequences of
      antibodies 28
<220> FEATURE:
<221> NAME/KEY: MISC_FEATURE
<222> LOCATION: (1)..(1)
<223> OTHER INFORMATION: Xaa is absent or A

<400> SEQUENCE: 17

Xaa Ser Thr Lys Gly Pro Ser Val Phe Pro Leu Ala Pro Ser Ser Arg
 1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Cys Gly Pro Pro Cys Pro Ser Cys Pro Ala Pro
             100                 105                 110

Glu Phe Leu Gly Gly Pro
        115

<210> SEQ ID NO 18
<211> LENGTH: 118
<212> TYPE: PRT
<213> ORGANISM: Artificial Sequence
<220> FEATURE:
<223> OTHER INFORMATION: CH1 domain and hinge region sequences of
      antibodies 29
<220> FEATURE:
<221> NAME/KEY: MISC_FEATURE
<222> LOCATION: (1)..(1)
<223> OTHER INFORMATION: Xaa is absent or A

<400> SEQUENCE: 18

Xaa Ser Thr Lys Gly Pro Ser Val Phe Pro Leu Ala Pro Ser Ser Arg
 1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
```

```
                35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Cys Gly Pro Pro Ser Pro Ser Cys Pro Ala Pro
            100                 105                 110

Glu Phe Leu Gly Gly Pro
        115

<210> SEQ ID NO 19
<211> LENGTH: 118
<212> TYPE: PRT
<213> ORGANISM: Artificial Sequence
<220> FEATURE:
<223> OTHER INFORMATION: CH1 domain and hinge region sequences of
      antibodies 30
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 19

Xaa Ser Thr Lys Gly Pro Ser Val Phe Pro Leu Ala Pro Ser Ser Arg
  1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Xaa Ser Lys Cys Gly Pro Pro Cys Pro Ser Pro Ala Pro
            100                 105                 110

Glu Phe Leu Gly Gly Pro
        115

<210> SEQ ID NO 20
<211> LENGTH: 118
<212> TYPE: PRT
<213> ORGANISM: Artificial Sequence
<220> FEATURE:
<223> OTHER INFORMATION: CH1 domain and hinge region sequences of
      antibodies 31
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 20
```

```
Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Cys Gly Pro Pro Ser Pro Ser Ser Pro Ala Pro
            100                 105                 110

Glu Phe Leu Gly Gly Pro
            115
```

<210> SEQ ID NO 21
<211> LENGTH: 118
<212> TYPE: PRT
<213> ORGANISM: Artificial Sequence
<220> FEATURE:
<223> OTHER INFORMATION: CH1 domain and hinge region sequences of
      antibodies 32
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 21

```
Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Cys Tyr Gly Pro Pro Cys Pro Ser Cys Pro Ala Pro
            100                 105                 110

Glu Phe Leu Gly Gly Pro
            115
```

<210> SEQ ID NO 22
<211> LENGTH: 118
<212> TYPE: PRT
<213> ORGANISM: Artificial Sequence
<220> FEATURE:
<223> OTHER INFORMATION: CH1 domain and hinge region sequences of
      antibodies 33
<220> FEATURE:
<221> NAME/KEY: MISC_FEATURE
<222> LOCATION: (1)..(1)
<223> OTHER INFORMATION: Xaa is absent or A

```
<220> FEATURE:
<221> NAME/KEY: MISC_FEATURE
<222> LOCATION: (99)..(99)
<223> OTHER INFORMATION: Xaa is absent or E

<400> SEQUENCE: 22

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Cys Tyr Gly Pro Pro Ser Pro Ser Cys Pro Ala Pro
            100                 105                 110

Glu Phe Leu Gly Gly Pro
            115

<210> SEQ ID NO 23
<211> LENGTH: 118
<212> TYPE: PRT
<213> ORGANISM: Artificial Sequence
<220> FEATURE:
<223> OTHER INFORMATION: CH1 domain and hinge region sequences of
      antibodies 34
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 23

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Cys Tyr Gly Pro Pro Cys Pro Ser Ser Pro Ala Pro
            100                 105                 110

Glu Phe Leu Gly Gly Pro
            115

<210> SEQ ID NO 24
<211> LENGTH: 118
<212> TYPE: PRT
<213> ORGANISM: Artificial Sequence
```

```
<220> FEATURE:
<223> OTHER INFORMATION: CH1 domain and hinge region sequences of
      antibodies 35
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 24

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Cys Tyr Gly Pro Pro Ser Pro Ser Pro Ala Pro
            100                 105                 110

Glu Phe Leu Gly Gly Pro
            115

<210> SEQ ID NO 25
<211> LENGTH: 118
<212> TYPE: PRT
<213> ORGANISM: Artificial Sequence
<220> FEATURE:
<223> OTHER INFORMATION: CH1 domain and hinge region sequences of
      antibodies 36
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 25

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Cys Lys Tyr Gly Pro Pro Cys Pro Ser Cys Pro Ala Pro
            100                 105                 110

Glu Phe Leu Gly Gly Pro
```

```
<210> SEQ ID NO 26
<211> LENGTH: 118
<212> TYPE: PRT
<213> ORGANISM: Artificial Sequence
<220> FEATURE:
<223> OTHER INFORMATION: CH1 domain and hinge region sequences of
      antibodies 37
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 26

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Cys Lys Tyr Gly Pro Pro Ser Pro Ser Cys Pro Ala Pro
            100                 105                 110

Glu Phe Leu Gly Gly Pro
            115

<210> SEQ ID NO 27
<211> LENGTH: 118
<212> TYPE: PRT
<213> ORGANISM: Artificial Sequence
<220> FEATURE:
<223> OTHER INFORMATION: CH1 domain and hinge region sequences of
      antibodies 38
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 27

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80
```

Tyr Thr Cys Asn Val Asp His Lys Pro Ser Asn Thr Lys Val Asp Lys
                85                  90                  95

Arg Val Xaa Cys Lys Tyr Gly Pro Pro Cys Pro Ser Pro Ala Pro
            100                 105                 110

Glu Phe Leu Gly Gly Pro
        115

<210> SEQ ID NO 28
<211> LENGTH: 118
<212> TYPE: PRT
<213> ORGANISM: Artificial Sequence
<220> FEATURE:
<223> OTHER INFORMATION: CH1 domain and hinge region sequences of
      antibodies 39
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 28

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Cys Lys Tyr Gly Pro Pro Ser Pro Ser Ser Pro Ala Pro
            100                 105                 110

Glu Phe Leu Gly Gly Pro
        115

<210> SEQ ID NO 29
<211> LENGTH: 121
<212> TYPE: PRT
<213> ORGANISM: Artificial Sequence
<220> FEATURE:
<223> OTHER INFORMATION: CH1 domain and hinge region sequences of
      antibodies 44
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 29

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                    85                  90                  95

Arg Val Xaa Ser Lys Tyr Cys Pro Pro Ala Ala Ala Cys Pro Ser Cys
                100                 105                 110

Pro Ala Pro Glu Phe Leu Gly Gly Pro
            115                 120

<210> SEQ ID NO 30
<211> LENGTH: 121
<212> TYPE: PRT
<213> ORGANISM: Artificial Sequence
<220> FEATURE:
<223> OTHER INFORMATION: CH1 domain and hinge region sequences of
      antibodies 45
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 30

Xaa Ser Thr Lys Gly Pro Ser Val Phe Pro Leu Ala Pro Ser Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                    85                  90                  95

Arg Val Xaa Ser Lys Tyr Cys Pro Pro Ala Ala Ala Ser Pro Ser Cys
                100                 105                 110

Pro Ala Pro Glu Phe Leu Gly Gly Pro
            115                 120

<210> SEQ ID NO 31
<211> LENGTH: 121
<212> TYPE: PRT
<213> ORGANISM: Artificial Sequence
<220> FEATURE:
<223> OTHER INFORMATION: CH1 domain and hinge region sequences of
      antibodies 46
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 31

Xaa Ser Thr Lys Gly Pro Ser Val Phe Pro Leu Ala Pro Ser Ser Arg

```
                1               5                  10                  15
        Ser Thr Ser Glu Ser Thr Ala Ala Leu Gly Cys Leu Val Lys Asp Tyr
                        20                  25                  30

Phe Pro Glu Pro Val Thr Val Ser Trp Asn Ser Gly Ala Leu Thr Ser
                        35                  40                  45

Gly Val His Thr Phe Pro Ala Val Leu Gln Ser Ser Gly Leu Tyr Ser
                50                      55                  60

Leu Ser Ser Val Val Thr Val Pro Ser Ser Leu Gly Thr Lys Thr
         65                     70                  75                  80

Tyr Thr Cys Asn Val Asp His Lys Pro Ser Asn Thr Lys Val Asp Lys
                            85                  90                  95

Arg Val Xaa Ser Lys Tyr Cys Pro Pro Ala Ala Ala Cys Pro Ser Ser
                        100                 105                 110

Pro Ala Pro Glu Phe Leu Gly Gly Pro
                    115                 120

<210> SEQ ID NO 32
<211> LENGTH: 121
<212> TYPE: PRT
<213> ORGANISM: Artificial Sequence
<220> FEATURE:
<223> OTHER INFORMATION: CH1 domain and hinge region sequences of
      antibodies 47
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 32

Xaa Ser Thr Lys Gly Pro Ser Val Phe Pro Leu Ala Pro Ser Ser Arg
         1               5                  10                  15

Ser Thr Ser Glu Ser Thr Ala Ala Leu Gly Cys Leu Val Lys Asp Tyr
                        20                  25                  30

Phe Pro Glu Pro Val Thr Val Ser Trp Asn Ser Gly Ala Leu Thr Ser
                        35                  40                  45

Gly Val His Thr Phe Pro Ala Val Leu Gln Ser Ser Gly Leu Tyr Ser
                50                      55                  60

Leu Ser Ser Val Val Thr Val Pro Ser Ser Leu Gly Thr Lys Thr
         65                     70                  75                  80

Tyr Thr Cys Asn Val Asp His Lys Pro Ser Asn Thr Lys Val Asp Lys
                            85                  90                  95

Arg Val Xaa Ser Lys Tyr Cys Pro Pro Ala Ala Ala Ser Pro Ser Ser
                        100                 105                 110

Pro Ala Pro Glu Phe Leu Gly Gly Pro
                    115                 120

<210> SEQ ID NO 33
<211> LENGTH: 118
<212> TYPE: PRT
<213> ORGANISM: Artificial Sequence
<220> FEATURE:
<223> OTHER INFORMATION: CH1 domain and hinge region sequences of
      antibodies 2
<220> FEATURE:
<221> NAME/KEY: MISC_FEATURE
<222> LOCATION: (1)..(1)
<223> OTHER INFORMATION: Xaa is absent or A
<220> FEATURE:
```

<221> NAME/KEY: MISC_FEATURE
<222> LOCATION: (99)..(99)
<223> OTHER INFORMATION: Xaa is absent or E

<400> SEQUENCE: 33

```
Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Gly Pro Pro Ser Pro Ser Cys Pro Ala Pro
            100                 105                 110

Glu Phe Leu Gly Gly Pro
            115
```

<210> SEQ ID NO 34
<211> LENGTH: 118
<212> TYPE: PRT
<213> ORGANISM: Artificial Sequence
<220> FEATURE:
<223> OTHER INFORMATION: CH1 domain and hinge region sequences of
      antibodies 3
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 34

```
Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Gly Pro Pro Cys Pro Ser Ser Pro Ala Pro
            100                 105                 110

Glu Phe Leu Gly Gly Pro
            115
```

<210> SEQ ID NO 35
<211> LENGTH: 121
<212> TYPE: PRT
<213> ORGANISM: Artificial Sequence
<220> FEATURE:

<223> OTHER INFORMATION: CH1 domain and hinge region sequences of
    antibodies 48
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 35

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Pro Lys Ser Cys Asp Lys Thr His Thr Cys Pro Pro Cys
            100                 105                 110

Pro Ala Pro Glu Phe Leu Gly Gly Pro
            115                 120

<210> SEQ ID NO 36
<211> LENGTH: 118
<212> TYPE: PRT
<213> ORGANISM: Artificial Sequence
<220> FEATURE:
<223> OTHER INFORMATION: CH1 domain and hinge region sequences of
    antibodies 28P
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 36

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Cys Gly Pro Pro Cys Pro Pro Cys Pro Ala Pro
            100                 105                 110

Glu Phe Leu Gly Gly Pro
            115

```
<210> SEQ ID NO 37
<211> LENGTH: 121
<212> TYPE: PRT
<213> ORGANISM: Artificial Sequence
<220> FEATURE:
<223> OTHER INFORMATION: CH1 domain and hinge region sequences of
      antibodies 44P
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 37

Xaa Ser Thr Lys Gly Pro Ser Val Phe Pro Leu Ala Pro Ser Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Cys Pro Pro Ala Ala Ala Cys Pro Pro Cys
            100                 105                 110

Pro Ala Pro Glu Phe Leu Gly Gly Pro
        115                 120

<210> SEQ ID NO 38
<211> LENGTH: 327
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 6
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 38

Xaa Ser Thr Lys Gly Pro Ser Val Phe Pro Leu Ala Pro Ser Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
```

```
                85                  90                  95
Arg Val Xaa Ser Lys Tyr Cys Pro Pro Ser Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 39
<211> LENGTH: 327
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 7
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 39

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
```

```
                65                  70                  75                  80
Tyr Thr Cys Asn Val Asp His Lys Pro Ser Asn Thr Lys Val Asp Lys
                    85                  90                  95
Arg Val Xaa Ser Lys Tyr Cys Pro Pro Cys Pro Ser Ser Pro Ala Pro
                100                 105                 110
Glu Phe Leu Gly Gly Pro Ser Val Phe Leu Phe Pro Pro Lys Pro Lys
                115                 120                 125
Asp Thr Leu Met Ile Ser Arg Thr Pro Glu Val Thr Cys Val Val Val
            130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
                180                 185                 190
Trp Leu Asn Gly Lys Glu Tyr Lys Cys Lys Val Ser Asn Lys Gly Leu
            195                 200                 205
Pro Ser Ser Ile Glu Lys Thr Ile Ser Lys Ala Lys Gly Gln Pro Arg
        210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Gln Gly Asn Val Phe Ser
            290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 40
<211> LENGTH: 327
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 8
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 40

Xaa Ser Thr Lys Gly Pro Ser Val Phe Pro Leu Ala Pro Ser Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
```

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Cys Pro Pro Ser Pro Ser Pro Ala Pro
            100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
                290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 41
<211> LENGTH: 327
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 15
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 41

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser

```
                 35                  40                  45
Gly Val His Thr Phe Pro Ala Val Leu Gln Ser Ser Gly Leu Tyr Ser
 50                  55                  60
Leu Ser Ser Val Val Thr Val Pro Ser Ser Leu Gly Thr Lys Thr
 65                  70                  75                  80
Tyr Thr Cys Asn Val Asp His Lys Pro Ser Asn Thr Lys Val Asp Lys
                 85                  90                  95
Arg Val Xaa Ser Lys Tyr Cys Pro Pro Cys Pro Ser Cys Pro Ala Pro
                100                 105                 110
Glu Phe Leu Gly Gly Pro Ser Val Phe Leu Phe Pro Pro Lys Pro Lys
                115                 120                 125
Asp Thr Leu Met Ile Ser Arg Thr Pro Glu Val Thr Cys Val Val Val
130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Gln Phe
                165                 170                 175
Asn Ser Thr Tyr Arg Val Val Ser Val Leu Thr Val Leu His Gln Asp
                180                 185                 190
Trp Leu Asn Gly Lys Glu Tyr Lys Cys Lys Val Ser Asn Lys Gly Leu
                195                 200                 205
Pro Ser Ser Ile Glu Lys Thr Ile Ser Lys Ala Lys Gly Gln Pro Arg
210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
                260                 265                 270
Thr Thr Pro Pro Val Leu Asp Ser Asp Gly Ser Phe Phe Leu Tyr Ser
                275                 280                 285
Arg Leu Thr Val Asp Lys Ser Arg Trp Gln Glu Gly Asn Val Phe Ser
290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 42
<211> LENGTH: 327
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 16
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 42

Xaa Ser Thr Lys Gly Pro Ser Val Phe Pro Leu Ala Pro Ser Ser Arg
 1               5                  10                  15

Ser Thr Ser Glu Ser Thr Ala Ala Leu Gly Cys Leu Val Lys Asp Tyr
```

```
            20                  25                  30
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Cys Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 43
<211> LENGTH: 327
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 28
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 43

Xaa Ser Thr Lys Gly Pro Ser Val Phe Pro Leu Ala Pro Ser Ser Arg
```

```
                1               5                    10                   15
        Ser Thr Ser Glu Ser Thr Ala Ala Leu Gly Cys Leu Val Lys Asp Tyr
                        20                  25                  30

Phe Pro Glu Pro Val Thr Val Ser Trp Asn Ser Gly Ala Leu Thr Ser
                        35                  40                  45

Gly Val His Thr Phe Pro Ala Val Leu Gln Ser Ser Gly Leu Tyr Ser
                        50                  55                  60

Leu Ser Ser Val Val Thr Val Pro Ser Ser Leu Gly Thr Lys Thr
         65                  70                  75                  80

Tyr Thr Cys Asn Val Asp His Lys Pro Ser Asn Thr Lys Val Asp Lys
                            85                  90                  95

Arg Val Xaa Ser Lys Cys Gly Pro Pro Cys Pro Ser Cys Pro Ala Pro
                        100                 105                 110

Glu Phe Leu Gly Gly Pro Ser Val Phe Leu Phe Pro Pro Lys Pro Lys
                        115                 120                 125

Asp Thr Leu Met Ile Ser Arg Thr Pro Glu Val Thr Cys Val Val Val
                    130                 135                 140

Asp Val Ser Gln Glu Asp Pro Glu Val Gln Phe Asn Trp Tyr Val Asp
        145                 150                 155                 160

Gly Val Glu Val His Asn Ala Lys Thr Lys Pro Arg Glu Glu Gln Phe
                            165                 170                 175

Asn Ser Thr Tyr Arg Val Val Ser Val Leu Thr Val Leu His Gln Asp
                        180                 185                 190

Trp Leu Asn Gly Lys Glu Tyr Lys Cys Lys Val Ser Asn Lys Gly Leu
                        195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
        225                 230                 235                 240

Asn Gln Val Ser Leu Thr Cys Leu Val Lys Gly Phe Tyr Pro Ser Asp
                        245                 250                 255

Ile Ala Val Glu Trp Glu Ser Asn Gly Gln Pro Glu Asn Asn Tyr Lys
                        260                 265                 270

Thr Thr Pro Pro Val Leu Asp Ser Asp Gly Ser Phe Phe Leu Tyr Ser
                        275                 280                 285

Arg Leu Thr Val Asp Lys Ser Arg Trp Gln Gln Gly Asn Val Phe Ser
                        290                 295                 300

Cys Ser Val Met His Glu Ala Leu His Asn His Tyr Thr Gln Lys Ser
        305                 310                 315                 320

Leu Ser Leu Ser Leu Gly Lys
                        325

<210> SEQ ID NO 44
<211> LENGTH: 327
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 29
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E
```

<400> SEQUENCE: 44

```
Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Cys Gly Pro Pro Ser Pro Ser Cys Pro Ala Pro
            100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 45
<211> LENGTH: 327
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 30
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 45

| | | | | | | | | | | | | | | |
|---|---|---|---|---|---|---|---|---|---|---|---|---|---|---|
| Xaa | Ser | Thr | Lys | Gly | Pro | Ser | Val | Phe | Pro | Leu | Ala | Pro | Ser | Ser | Arg |
| 1 | | | | 5 | | | | | 10 | | | | | 15 | |
| Ser | Thr | Ser | Glu | Ser | Thr | Ala | Ala | Leu | Gly | Cys | Leu | Val | Lys | Asp | Tyr |
| | | | 20 | | | | | 25 | | | | | 30 | | |
| Phe | Pro | Glu | Pro | Val | Thr | Val | Ser | Trp | Asn | Ser | Gly | Ala | Leu | Thr | Ser |
| | | | 35 | | | | | 40 | | | | | 45 | | |
| Gly | Val | His | Thr | Phe | Pro | Ala | Val | Leu | Gln | Ser | Ser | Gly | Leu | Tyr | Ser |
| | | | 50 | | | | | 55 | | | | | 60 | | |
| Leu | Ser | Ser | Val | Val | Thr | Val | Pro | Ser | Ser | Ser | Leu | Gly | Thr | Lys | Thr |
| 65 | | | | | 70 | | | | | 75 | | | | | 80 |
| Tyr | Thr | Cys | Asn | Val | Asp | His | Lys | Pro | Ser | Asn | Thr | Lys | Val | Asp | Lys |
| | | | | 85 | | | | | 90 | | | | | 95 | |
| Arg | Val | Xaa | Ser | Lys | Cys | Gly | Pro | Pro | Cys | Pro | Ser | Ser | Pro | Ala | Pro |
| | | | 100 | | | | | 105 | | | | | 110 | | |
| Glu | Phe | Leu | Gly | Gly | Pro | Ser | Val | Phe | Leu | Phe | Pro | Pro | Lys | Pro | Lys |
| | | | 115 | | | | | 120 | | | | | 125 | | |
| Asp | Thr | Leu | Met | Ile | Ser | Arg | Thr | Pro | Glu | Val | Thr | Cys | Val | Val | Val |
| | 130 | | | | | 135 | | | | | 140 | | | | |
| Asp | Val | Ser | Gln | Glu | Asp | Pro | Glu | Val | Gln | Phe | Asn | Trp | Tyr | Val | Asp |
| 145 | | | | | 150 | | | | | 155 | | | | | 160 |
| Gly | Val | Glu | Val | His | Asn | Ala | Lys | Thr | Lys | Pro | Arg | Glu | Glu | Gln | Phe |
| | | | | 165 | | | | | 170 | | | | | 175 | |
| Asn | Ser | Thr | Tyr | Arg | Val | Val | Ser | Val | Leu | Thr | Val | Leu | His | Gln | Asp |
| | | | 180 | | | | | 185 | | | | | 190 | | |
| Trp | Leu | Asn | Gly | Lys | Glu | Tyr | Lys | Cys | Lys | Val | Ser | Asn | Lys | Gly | Leu |
| | | | 195 | | | | | 200 | | | | | 205 | | |
| Pro | Ser | Ser | Ile | Glu | Lys | Thr | Ile | Ser | Lys | Ala | Lys | Gly | Gln | Pro | Arg |
| | 210 | | | | | 215 | | | | | 220 | | | | |
| Glu | Pro | Gln | Val | Tyr | Thr | Leu | Pro | Pro | Ser | Gln | Glu | Glu | Met | Thr | Lys |
| 225 | | | | | 230 | | | | | 235 | | | | | 240 |
| Asn | Gln | Val | Ser | Leu | Thr | Cys | Leu | Val | Lys | Gly | Phe | Tyr | Pro | Ser | Asp |
| | | | | 245 | | | | | 250 | | | | | 255 | |
| Ile | Ala | Val | Glu | Trp | Glu | Ser | Asn | Gly | Gln | Pro | Glu | Asn | Asn | Tyr | Lys |
| | | | 260 | | | | | 265 | | | | | 270 | | |
| Thr | Thr | Pro | Pro | Val | Leu | Asp | Ser | Asp | Gly | Ser | Phe | Phe | Leu | Tyr | Ser |
| | | | 275 | | | | | 280 | | | | | 285 | | |
| Arg | Leu | Thr | Val | Asp | Lys | Ser | Arg | Trp | Gln | Glu | Gly | Asn | Val | Phe | Ser |
| | 290 | | | | | 295 | | | | | 300 | | | | |
| Cys | Ser | Val | Met | His | Glu | Ala | Leu | His | Asn | His | Tyr | Thr | Gln | Lys | Ser |
| 305 | | | | | 310 | | | | | 315 | | | | | 320 |
| Leu | Ser | Leu | Ser | Leu | Gly | Lys | | | | | | | | | |
| | | | | 325 | | | | | | | | | | | |

<210> SEQ ID NO 46
<211> LENGTH: 327
<212> TYPE: PRT
<213> ORGANISM: Artificial Sequence
<220> FEATURE:
<223> OTHER INFORMATION: CH1 domain, hinge region, CH2 domain and CH3 domain sequences of antibodies 31
<220> FEATURE:
<221> NAME/KEY: MISC_FEATURE
<222> LOCATION: (1)..(1)

<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 46

```
Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Cys Gly Pro Pro Ser Pro Ser Ser Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 47
<211> LENGTH: 327
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 32

```
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 47

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Cys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 48
<211> LENGTH: 327
<212> TYPE: PRT
<213> ORGANISM: Artificial Sequence
```

<220> FEATURE:
<223> OTHER INFORMATION: CH1 domain, hinge region, CH2 domain and CH3
      domain sequences of antibodies 33
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 48

```
Xaa Ser Thr Lys Gly Pro Ser Val Phe Pro Leu Ala Pro Ser Ser Arg
1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Cys Tyr Gly Pro Pro Ser Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 49

```
<211> LENGTH: 327
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 34
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 49

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Cys Tyr Gly Pro Pro Cys Pro Ser Ser Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

```
<210> SEQ ID NO 50
<211> LENGTH: 327
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 35
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 50

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Cys Tyr Gly Pro Pro Ser Pro Ser Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320
```

-continued

```
Leu Ser Leu Ser Leu Gly Lys
            325

<210> SEQ ID NO 51
<211> LENGTH: 327
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 36
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 51

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Cys Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300
```

-continued

```
Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 52
<211> LENGTH: 327
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 37
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 52

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Cys Lys Tyr Gly Pro Pro Ser Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285
```

```
Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 53
<211> LENGTH: 327
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 38
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 53

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Cys Lys Tyr Gly Pro Pro Cys Pro Ser Ser Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270
```

```
Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 54
<211> LENGTH: 327
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 39
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 54

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Cys Lys Tyr Gly Pro Pro Ser Pro Ser Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255
```

-continued

```
Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 55
<211> LENGTH: 330
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 44
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 55

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
            85                  90                  95

Arg Val Xaa Ser Lys Tyr Cys Pro Pro Ala Ala Cys Pro Ser Cys
            100                 105                 110

Pro Ala Pro Glu Phe Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser Gln Glu Asp Pro Glu Val Gln Phe Asn Trp
145                 150                 155                 160

Tyr Val Asp Gly Val Glu Val His Asn Ala Lys Thr Lys Pro Arg Glu
            165                 170                 175

Glu Gln Phe Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Gly Leu Pro Ser Ser Ile Glu Lys Thr Ile Ser Lys Ala Lys Gly
    210                 215                 220

Gln Pro Arg Glu Pro Gln Val Tyr Thr Leu Pro Pro Ser Gln Glu Glu
225                 230                 235                 240
```

-continued

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Arg Leu Thr Val Asp Lys Ser Arg Trp Gln Glu Gly Asn
290                 295                 300

Val Phe Ser Cys Ser Val Met His Glu Ala Leu His Asn His Tyr Thr
305                 310                 315                 320

Gln Lys Ser Leu Ser Leu Ser Leu Gly Lys
            325                 330

<210> SEQ ID NO 56
<211> LENGTH: 330
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 45
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 56

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
            85                  90                  95

Arg Val Xaa Ser Lys Tyr Cys Pro Pro Ala Ala Ala Ser Pro Ser Cys
            100                 105                 110

Pro Ala Pro Glu Phe Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser Gln Glu Asp Pro Glu Val Gln Phe Asn Trp
145                 150                 155                 160

Tyr Val Asp Gly Val Glu Val His Asn Ala Lys Thr Lys Pro Arg Glu
            165                 170                 175

Glu Gln Phe Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Gly Leu Pro Ser Ser Ile Glu Lys Thr Ile Ser Lys Ala Lys Gly
210                 215                 220

```
Gln Pro Arg Glu Pro Gln Val Tyr Thr Leu Pro Pro Ser Gln Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Glu Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Leu Gly Lys
            325                 330

<210> SEQ ID NO 57
<211> LENGTH: 330
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 46
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 57

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Cys Pro Pro Ala Ala Ala Cys Pro Ser Ser
                100                 105                 110

Pro Ala Pro Glu Phe Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser Gln Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Phe Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
    195                 200                 205
```

-continued

```
Lys Gly Leu Pro Ser Ser Ile Glu Lys Thr Ile Ser Lys Ala Lys Gly
            210                 215                 220

Gln Pro Arg Glu Pro Gln Val Tyr Thr Leu Pro Pro Ser Gln Glu Glu
225                 230                 235                 240

Met Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Arg Leu Thr Val Asp Lys Ser Arg Trp Gln Glu Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Leu Gly Lys
                325                 330
```

<210> SEQ ID NO 58
<211> LENGTH: 330
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 47
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 58

```
Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Cys Pro Pro Ala Ala Ser Pro Ser Ser
                100                 105                 110

Pro Ala Pro Glu Phe Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser Gln Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Phe Asn Ser Thr Tyr Arg Val Val Ser Val Leu Thr Val Leu
            180                 185                 190
```

```
His Gln Asp Trp Leu Asn Gly Lys Glu Tyr Lys Cys Lys Val Ser Asn
            195                 200                 205

Lys Gly Leu Pro Ser Ser Ile Glu Lys Thr Ile Ser Lys Ala Lys Gly
        210                 215                 220

Gln Pro Arg Glu Pro Gln Val Tyr Thr Leu Pro Pro Ser Gln Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Glu Gly Asn
290                 295                 300

Val Phe Ser Cys Ser Val Met His Glu Ala Leu His Asn His Tyr Thr
305                 310                 315                 320

Gln Lys Ser Leu Ser Leu Ser Leu Gly Lys
                325                 330

<210> SEQ ID NO 59
<211> LENGTH: 327
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 2
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 59

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Gly Pro Pro Ser Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175
```

```
Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 60
<211> LENGTH: 327
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 3
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 60

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Gly Pro Pro Cys Pro Ser Ser Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160
```

```
Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 61
<211> LENGTH: 330
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 48
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 61

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Pro Lys Ser Cys Asp Lys Thr His Thr Cys Pro Pro Cys
            100                 105                 110

Pro Ala Pro Glu Phe Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140
```

Val Val Val Asp Val Ser Gln Glu Asp Pro Glu Val Gln Phe Asn Trp
145                 150                 155                 160

Tyr Val Asp Gly Val Glu Val His Asn Ala Lys Thr Lys Pro Arg Glu
            165                 170                 175

Glu Gln Phe Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Gly Leu Pro Ser Ser Ile Glu Lys Thr Ile Ser Lys Ala Lys Gly
210                 215                 220

Gln Pro Arg Glu Pro Gln Val Tyr Thr Leu Pro Pro Ser Gln Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Leu Gly Lys
                325                 330

<210> SEQ ID NO 62
<211> LENGTH: 327
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 28P
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 62

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Cys Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

```
Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 63
<211> LENGTH: 330
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 44P
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 63

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Cys Pro Pro Ala Ala Ala Cys Pro Pro Cys
                100                 105                 110
```

```
Pro Ala Pro Glu Phe Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser Gln Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Phe Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Gly Leu Pro Ser Ser Ile Glu Lys Thr Ile Ser Lys Ala Lys Gly
210                 215                 220

Gln Pro Arg Glu Pro Gln Val Tyr Thr Leu Pro Pro Ser Gln Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Glu Gly Asn
290                 295                 300

Val Phe Ser Cys Ser Val Met His Glu Ala Leu His Asn His Tyr Thr
305                 310                 315                 320

Gln Lys Ser Leu Ser Leu Ser Leu Gly Lys
                325                 330

<210> SEQ ID NO 64
<211> LENGTH: 209
<212> TYPE: PRT
<213> ORGANISM: Artificial Sequence
<220> FEATURE:
<223> OTHER INFORMATION: wild type IgG4 CH2 and CH3

<400> SEQUENCE: 64

Ser Val Phe Leu Phe Pro Pro Lys Pro Lys Asp Thr Leu Met Ile Ser
1               5                   10                  15

Arg Thr Pro Glu Val Thr Cys Val Val Val Asp Val Ser Gln Glu Asp
            20                  25                  30

Pro Glu Val Gln Phe Asn Trp Tyr Val Asp Gly Val Glu Val His Asn
        35                  40                  45

Ala Lys Thr Lys Pro Arg Glu Glu Gln Phe Asn Ser Thr Tyr Arg Val
    50                  55                  60

Val Ser Val Leu Thr Val Leu His Gln Asp Trp Leu Asn Gly Lys Glu
65                  70                  75                  80

Tyr Lys Cys Lys Val Ser Asn Lys Gly Leu Pro Ser Ser Ile Glu Lys
                85                  90                  95

Thr Ile Ser Lys Ala Lys Gly Gln Pro Arg Glu Pro Gln Val Tyr Thr
            100                 105                 110

Leu Pro Pro Ser Gln Glu Glu Met Thr Lys Asn Gln Val Ser Leu Thr
        115                 120                 125

Cys Leu Val Lys Gly Phe Tyr Pro Ser Asp Ile Ala Val Glu Trp Glu
    130                 135                 140
```

```
Ser Asn Gly Gln Pro Glu Asn Asn Tyr Lys Thr Thr Pro Pro Val Leu
145                 150                 155                 160

Asp Ser Asp Gly Ser Phe Phe Leu Tyr Ser Arg Leu Thr Val Asp Lys
                165                 170                 175

Ser Arg Trp Gln Glu Gly Asn Val Phe Ser Cys Ser Val Met His Glu
            180                 185                 190

Ala Leu His Asn His Tyr Thr Gln Lys Ser Leu Ser Leu Ser Leu Gly
        195                 200                 205

Lys

<210> SEQ ID NO 65
<211> LENGTH: 209
<212> TYPE: PRT
<213> ORGANISM: Artificial Sequence
<220> FEATURE:
<223> OTHER INFORMATION: wild type IgG4 CH2 and wild type IgG1 CH3

<400> SEQUENCE: 65

Ser Val Phe Leu Phe Pro Pro Lys Pro Lys Asp Thr Leu Met Ile Ser
1               5                   10                  15

Arg Thr Pro Glu Val Thr Cys Val Val Val Asp Val Ser Gln Glu Asp
            20                  25                  30

Pro Glu Val Gln Phe Asn Trp Tyr Val Asp Gly Val Glu Val His Asn
        35                  40                  45

Ala Lys Thr Lys Pro Arg Glu Glu Gln Phe Asn Ser Thr Tyr Arg Val
    50                  55                  60

Val Ser Val Leu Thr Val Leu His Gln Asp Trp Leu Asn Gly Lys Glu
65                  70                  75                  80

Tyr Lys Cys Lys Val Ser Asn Lys Gly Leu Pro Ser Ser Ile Glu Lys
                85                  90                  95

Thr Ile Ser Lys Ala Lys Gly Gln Pro Arg Glu Pro Gln Val Tyr Thr
            100                 105                 110

Leu Pro Pro Ser Arg Asp Glu Leu Thr Lys Asn Gln Val Ser Leu Thr
        115                 120                 125

Cys Leu Val Lys Gly Phe Tyr Pro Ser Asp Ile Ala Val Glu Trp Glu
130                 135                 140

Ser Asn Gly Gln Pro Glu Asn Asn Tyr Lys Thr Thr Pro Pro Val Leu
145                 150                 155                 160

Asp Ser Asp Gly Ser Phe Phe Leu Tyr Ser Lys Leu Thr Val Asp Lys
                165                 170                 175

Ser Arg Trp Gln Gln Gly Asn Val Phe Ser Cys Ser Val Met His Glu
            180                 185                 190

Ala Leu His Asn His Tyr Thr Gln Lys Ser Leu Ser Leu Ser Pro Gly
        195                 200                 205

Lys

<210> SEQ ID NO 66
<211> LENGTH: 106
<212> TYPE: PRT
<213> ORGANISM: Artificial Sequence
<220> FEATURE:
<223> OTHER INFORMATION: constant region sequence of a human wild-type
      kappa light chain.

<400> SEQUENCE: 66

Thr Val Ala Ala Pro Ser Val Phe Ile Phe Pro Pro Ser Asp Glu Gln
1               5                   10                  15
```

```
Leu Lys Ser Gly Thr Ala Ser Val Val Cys Leu Leu Asn Asn Phe Tyr
             20                  25                  30

Pro Arg Glu Ala Lys Val Gln Trp Lys Val Asp Asn Ala Leu Gln Ser
         35                  40                  45

Gly Asn Ser Gln Glu Ser Val Thr Glu Gln Asp Ser Lys Asp Ser Thr
 50                  55                  60

Tyr Ser Leu Ser Ser Thr Leu Thr Leu Ser Lys Ala Asp Tyr Glu Lys
 65                  70                  75                  80

His Lys Val Tyr Ala Cys Glu Val Thr His Gln Gly Leu Ser Ser Pro
             85                  90                  95

Val Thr Lys Ser Phe Asn Arg Gly Glu Cys
            100                 105

<210> SEQ ID NO 67
<211> LENGTH: 9
<212> TYPE: PRT
<213> ORGANISM: Artificial Sequence
<220> FEATURE:
<223> OTHER INFORMATION: N-terminal sequence of the CH1 domain of a
      human IgD

<400> SEQUENCE: 67

Ile Ile Ser Gly Cys Arg His Pro Lys
1               5

<210> SEQ ID NO 68
<211> LENGTH: 34
<212> TYPE: PRT
<213> ORGANISM: Artificial Sequence
<220> FEATURE:
<223> OTHER INFORMATION: the hinge region of a human IgGD antibody
<220> FEATURE:
<221> NAME/KEY: MISC_FEATURE
<222> LOCATION: (1)..(1)
<223> OTHER INFORMATION: Xaa is absent or E

<400> SEQUENCE: 68

Xaa Ser Pro Lys Ala Gln Ala Ser Ser Val Pro Thr Ala Gln Pro Gln
1               5                  10                  15

Ala Glu Gly Ser Leu Ala Lys Ala Thr Thr Ala Pro Ala Thr Thr Arg
             20                  25                  30

Asn Thr

<210> SEQ ID NO 69
<211> LENGTH: 9
<212> TYPE: PRT
<213> ORGANISM: Artificial Sequence
<220> FEATURE:
<223> OTHER INFORMATION: N-terminal sequence of the CH1 domain of a
      human IgM antibody.

<400> SEQUENCE: 69

Leu Val Ser Cys Glu Asn Ser Pro Ser
1               5

<210> SEQ ID NO 70
<211> LENGTH: 7
<212> TYPE: PRT
<213> ORGANISM: Artificial Sequence
<220> FEATURE:
<223> OTHER INFORMATION: C-terminal sequence of the CH1 domain of a
      human IgM antibody.

<400> SEQUENCE: 70
```

Glu Lys Asn Val Pro Leu Pro
1               5

<210> SEQ ID NO 71
<211> LENGTH: 11
<212> TYPE: PRT
<213> ORGANISM: Artificial Sequence
<220> FEATURE:
<223> OTHER INFORMATION: CH2 domain of a human IgM antibody.
<220> FEATURE:
<221> NAME/KEY: X
<222> LOCATION: (1)..(1)
<223> OTHER INFORMATION: Absent of V

<400> SEQUENCE: 71

Xaa Ile Ala Glu Leu Pro Pro Lys Val Ser Val
1               5                   10

<210> SEQ ID NO 72
<211> LENGTH: 15
<212> TYPE: PRT
<213> ORGANISM: Artificial Sequence
<220> FEATURE:
<223> OTHER INFORMATION: IgG4 hinge

<400> SEQUENCE: 72

Glu Ser Lys Tyr Gly Pro Pro Ala Ala Ala Cys Pro Ser Cys Pro
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: IgG4 hinge

<400> SEQUENCE: 73

Glu Ser Lys Tyr Gly Pro Pro Gly Gly Gly Cys Pro Ser Cys Pro
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: IgG4 hinge

<400> SEQUENCE: 74

Glu Ser Lys Tyr Gly Pro Pro Thr His Thr Cys Pro Ser Cys Pro
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: IgG4 hinge

<400> SEQUENCE: 75

Glu Ser Lys Tyr Gly Asp Lys Thr His Thr Cys Pro Ser Cys Pro
1               5                   10                  15

<210> SEQ ID NO 76
<211> LENGTH: 16
<212> TYPE: PRT
<213> ORGANISM: Artificial Sequence
<220> FEATURE:

<223> OTHER INFORMATION: IgG4 hinge

<400> SEQUENCE: 76

Glu Pro Ser Lys Tyr Gly Pro Pro Ala Ala Ala Cys Pro Ser Cys Pro
1               5                   10                  15

<210> SEQ ID NO 77
<211> LENGTH: 16
<212> TYPE: PRT
<213> ORGANISM: Artificial Sequence
<220> FEATURE:
<223> OTHER INFORMATION: IgG4 hinge

<400> SEQUENCE: 77

Glu Pro Ser Lys Tyr Gly Pro Pro Gly Gly Cys Pro Ser Cys Pro
1               5                   10                  15

<210> SEQ ID NO 78
<211> LENGTH: 16
<212> TYPE: PRT
<213> ORGANISM: Artificial Sequence
<220> FEATURE:
<223> OTHER INFORMATION: IgG4 hinge

<400> SEQUENCE: 78

Glu Pro Ser Lys Tyr Gly Pro Pro Thr His Thr Cys Pro Ser Cys Pro
1               5                   10                  15

<210> SEQ ID NO 79
<211> LENGTH: 16
<212> TYPE: PRT
<213> ORGANISM: Artificial Sequence
<220> FEATURE:
<223> OTHER INFORMATION: IgG4 hinge

<400> SEQUENCE: 79

Glu Pro Ser Lys Tyr Gly Asp Lys Thr His Thr Cys Pro Ser Cys Pro
1               5                   10                  15

<210> SEQ ID NO 80
<211> LENGTH: 16
<212> TYPE: PRT
<213> ORGANISM: Artificial Sequence
<220> FEATURE:
<223> OTHER INFORMATION: IgG4 hinge

<400> SEQUENCE: 80

Glu Ser Lys Ser Tyr Gly Pro Pro Ala Ala Ala Cys Pro Ser Cys Pro
1               5                   10                  15

<210> SEQ ID NO 81
<211> LENGTH: 16
<212> TYPE: PRT
<213> ORGANISM: Artificial Sequence
<220> FEATURE:
<223> OTHER INFORMATION: IgG4 hinge

<400> SEQUENCE: 81

Glu Ser Lys Ser Tyr Gly Pro Pro Gly Gly Gly Cys Pro Ser Cys Pro
1               5                   10                  15

<210> SEQ ID NO 82
<211> LENGTH: 16
<212> TYPE: PRT
<213> ORGANISM: Artificial Sequence
<220> FEATURE:
<223> OTHER INFORMATION: IgG4 hinge

```
<400> SEQUENCE: 82

Glu Ser Lys Ser Tyr Gly Pro Pro Thr His Thr Cys Pro Ser Cys Pro
1               5                   10                  15

<210> SEQ ID NO 83
<211> LENGTH: 16
<212> TYPE: PRT
<213> ORGANISM: Artificial Sequence
<220> FEATURE:
<223> OTHER INFORMATION: IgG4 hinge

<400> SEQUENCE: 83

Glu Ser Lys Ser Tyr Gly Asp Lys Thr His Thr Cys Pro Ser Cys Pro
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: IgG4 hinge

<400> SEQUENCE: 84

Glu Ser Lys Tyr Gly Pro Pro Ala Ala Ala Cys Pro Pro Cys Pro
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: IgG4 hinge

<400> SEQUENCE: 85

Glu Ser Lys Tyr Gly Pro Pro Gly Gly Gly Cys Pro Pro Cys Pro
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: IgG4 hinge

<400> SEQUENCE: 86

Glu Ser Lys Tyr Gly Pro Pro Thr His Thr Cys Pro Pro Cys Pro
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: IgG4 hinge

<400> SEQUENCE: 87

Glu Ser Lys Tyr Gly Asp Lys Thr His Thr Cys Pro Pro Cys Pro
1               5                   10                  15

<210> SEQ ID NO 88
<211> LENGTH: 16
<212> TYPE: PRT
<213> ORGANISM: Artificial Sequence
<220> FEATURE:
<223> OTHER INFORMATION: IgG4 hinge
```

```
<400> SEQUENCE: 88

Glu Pro Ser Lys Tyr Gly Pro Pro Ala Ala Ala Cys Pro Pro Cys Pro
1               5                   10                  15

<210> SEQ ID NO 89
<211> LENGTH: 16
<212> TYPE: PRT
<213> ORGANISM: Artificial Sequence
<220> FEATURE:
<223> OTHER INFORMATION: IgG4 hinge

<400> SEQUENCE: 89

Glu Pro Ser Lys Tyr Gly Pro Pro Gly Gly Gly Cys Pro Pro Cys Pro
1               5                   10                  15

<210> SEQ ID NO 90
<211> LENGTH: 16
<212> TYPE: PRT
<213> ORGANISM: Artificial Sequence
<220> FEATURE:
<223> OTHER INFORMATION: IgG4 hinge

<400> SEQUENCE: 90

Glu Pro Ser Lys Tyr Gly Pro Pro Thr His Thr Cys Pro Pro Cys Pro
1               5                   10                  15

<210> SEQ ID NO 91
<211> LENGTH: 16
<212> TYPE: PRT
<213> ORGANISM: Artificial Sequence
<220> FEATURE:
<223> OTHER INFORMATION: IgG4 hinge

<400> SEQUENCE: 91

Glu Pro Ser Lys Tyr Gly Asp Lys Thr His Thr Cys Pro Pro Cys Pro
1               5                   10                  15

<210> SEQ ID NO 92
<211> LENGTH: 16
<212> TYPE: PRT
<213> ORGANISM: Artificial Sequence
<220> FEATURE:
<223> OTHER INFORMATION: IgG4 hinge

<400> SEQUENCE: 92

Glu Ser Lys Ser Tyr Gly Pro Pro Ala Ala Ala Cys Pro Pro Cys Pro
1               5                   10                  15

<210> SEQ ID NO 93
<211> LENGTH: 16
<212> TYPE: PRT
<213> ORGANISM: Artificial Sequence
<220> FEATURE:
<223> OTHER INFORMATION: IgG4 hinge

<400> SEQUENCE: 93

Glu Ser Lys Ser Tyr Gly Pro Pro Gly Gly Gly Cys Pro Pro Cys Pro
1               5                   10                  15

<210> SEQ ID NO 94
<211> LENGTH: 16
<212> TYPE: PRT
<213> ORGANISM: Artificial Sequence
<220> FEATURE:
<223> OTHER INFORMATION: IgG4 hinge

<400> SEQUENCE: 94
```

```
Glu Ser Lys Ser Tyr Gly Pro Pro Thr His Thr Cys Pro Pro Cys Pro
1               5                   10                  15

<210> SEQ ID NO 95
<211> LENGTH: 16
<212> TYPE: PRT
<213> ORGANISM: Artificial Sequence
<220> FEATURE:
<223> OTHER INFORMATION: IgG4 hinge

<400> SEQUENCE: 95

Glu Ser Lys Ser Tyr Gly Asp Lys Thr His Thr Cys Pro Pro Cys Pro
1               5                   10                  15

<210> SEQ ID NO 96
<211> LENGTH: 14
<212> TYPE: PRT
<213> ORGANISM: Artificial Sequence
<220> FEATURE:
<223> OTHER INFORMATION: hinge

<400> SEQUENCE: 96

Glu Pro Lys Ser Cys Asp Lys Thr His Thr Cys Pro Pro Cys
1               5                   10

<210> SEQ ID NO 97
<211> LENGTH: 15
<212> TYPE: PRT
<213> ORGANISM: Artificial Sequence
<220> FEATURE:
<223> OTHER INFORMATION: Hinge Sequence

<400> SEQUENCE: 97

Glu Pro Lys Ser Cys Asp Lys Ala Ala Ala Cys Pro Pro Cys Pro
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: HINGE

<400> SEQUENCE: 98

Glu Pro Lys Ser Cys Asp Lys Gly Gly Gly Cys Pro Pro Cys Pro
1               5                   10                  15

<210> SEQ ID NO 99
<211> LENGTH: 15
<212> TYPE: PRT
<213> ORGANISM: Artificial Sequence
<220> FEATURE:
<223> OTHER INFORMATION: hinge

<400> SEQUENCE: 99

Glu Pro Lys Ser Cys Asp Lys Thr His Thr Ser Pro Pro Cys Pro
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: hinge

<400> SEQUENCE: 100
```

Glu Pro Lys Ser Cys Asp Lys Thr His Thr Cys Pro Pro Ser Pro
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: hinge

<400> SEQUENCE: 101

Glu Pro Lys Ser Cys Asp Lys Thr His Thr Ser Pro Pro Ser Pro
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: hinge

<400> SEQUENCE: 102

Glu Pro Lys Ser Cys Asp Lys Ala Ala Ala Ser Pro Pro Cys Pro
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: hinge

<400> SEQUENCE: 103

Glu Pro Lys Ser Cys Asp Lys Ala Ala Ala Cys Pro Pro Ser Pro
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: hinge

<400> SEQUENCE: 104

Glu Pro Lys Ser Cys Asp Lys Ala Ala Ala Ser Pro Pro Ser Pro
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: hinge

<400> SEQUENCE: 105

Glu Pro Lys Ser Cys Asp Lys Gly Gly Gly Ser Pro Pro Cys Pro
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: hinge

<400> SEQUENCE: 106

Glu Pro Lys Ser Cys Asp Lys Gly Gly Gly Cys Pro Pro Ser Pro

```
<210> SEQ ID NO 107
<211> LENGTH: 15
<212> TYPE: PRT
<213> ORGANISM: Artificial Sequence
<220> FEATURE:
<223> OTHER INFORMATION: hinge

<400> SEQUENCE: 107

Glu Pro Lys Ser Cys Asp Lys Gly Gly Gly Ser Pro Pro Ser Pro
1               5                   10                  15

<210> SEQ ID NO 108
<211> LENGTH: 12
<212> TYPE: PRT
<213> ORGANISM: Artificial Sequence
<220> FEATURE:
<223> OTHER INFORMATION: hinge

<400> SEQUENCE: 108

Glu Ser Lys Tyr Gly Pro Pro Cys Pro Ser Cys Pro
1               5                   10

<210> SEQ ID NO 109
<211> LENGTH: 12
<212> TYPE: PRT
<213> ORGANISM: Artificial Sequence
<220> FEATURE:
<223> OTHER INFORMATION: hinge

<400> SEQUENCE: 109

Glu Ser Lys Tyr Gly Asp Lys Cys Pro Ser Cys Pro
1               5                   10

<210> SEQ ID NO 110
<211> LENGTH: 13
<212> TYPE: PRT
<213> ORGANISM: Artificial Sequence
<220> FEATURE:
<223> OTHER INFORMATION: hinge

<400> SEQUENCE: 110

Glu Pro Ser Lys Tyr Gly Pro Pro Cys Pro Ser Cys Pro
1               5                   10

<210> SEQ ID NO 111
<211> LENGTH: 13
<212> TYPE: PRT
<213> ORGANISM: Artificial Sequence
<220> FEATURE:
<223> OTHER INFORMATION: hinge

<400> SEQUENCE: 111

Glu Pro Ser Lys Tyr Gly Asp Lys Cys Pro Ser Cys Pro
1               5                   10

<210> SEQ ID NO 112
<211> LENGTH: 13
<212> TYPE: PRT
<213> ORGANISM: Artificial Sequence
<220> FEATURE:
<223> OTHER INFORMATION: hinge

<400> SEQUENCE: 112

Glu Ser Lys Ser Tyr Gly Pro Pro Cys Pro Ser Cys Pro
1               5                   10
```

```
<210> SEQ ID NO 113
<211> LENGTH: 13
<212> TYPE: PRT
<213> ORGANISM: Artificial Sequence
<220> FEATURE:
<223> OTHER INFORMATION: hinge

<400> SEQUENCE: 113

Glu Ser Lys Ser Tyr Gly Asp Lys Cys Pro Ser Cys Pro
1               5                  10

<210> SEQ ID NO 114
<211> LENGTH: 14
<212> TYPE: PRT
<213> ORGANISM: Artificial Sequence
<220> FEATURE:
<223> OTHER INFORMATION: hinge

<400> SEQUENCE: 114

Glu Ser Lys Tyr Gly Pro Pro Ala Ala Cys Pro Ser Cys Pro
1               5                  10

<210> SEQ ID NO 115
<211> LENGTH: 14
<212> TYPE: PRT
<213> ORGANISM: Artificial Sequence
<220> FEATURE:
<223> OTHER INFORMATION: hinge

<400> SEQUENCE: 115

Glu Ser Lys Tyr Gly Pro Pro Gly Gly Cys Pro Ser Cys Pro
1               5                  10

<210> SEQ ID NO 116
<211> LENGTH: 14
<212> TYPE: PRT
<213> ORGANISM: Artificial Sequence
<220> FEATURE:
<223> OTHER INFORMATION: hinge

<400> SEQUENCE: 116

Glu Ser Lys Tyr Gly Pro Pro His Thr Cys Pro Ser Cys Pro
1               5                  10

<210> SEQ ID NO 117
<211> LENGTH: 14
<212> TYPE: PRT
<213> ORGANISM: Artificial Sequence
<220> FEATURE:
<223> OTHER INFORMATION: hinge

<400> SEQUENCE: 117

Glu Ser Lys Tyr Gly Asp Lys His Thr Cys Pro Ser Cys Pro
1               5                  10

<210> SEQ ID NO 118
<211> LENGTH: 15
<212> TYPE: PRT
<213> ORGANISM: Artificial Sequence
<220> FEATURE:
<223> OTHER INFORMATION: hinge

<400> SEQUENCE: 118

Glu Pro Ser Lys Tyr Gly Pro Pro Ala Ala Cys Pro Ser Cys Pro
1               5                  10                  15
```

```
<210> SEQ ID NO 119
<211> LENGTH: 15
<212> TYPE: PRT
<213> ORGANISM: Artificial Sequence
<220> FEATURE:
<223> OTHER INFORMATION: hinge

<400> SEQUENCE: 119

Glu Pro Ser Lys Tyr Gly Pro Pro Gly Gly Cys Pro Ser Cys Pro
1               5                   10                  15

<210> SEQ ID NO 120
<211> LENGTH: 15
<212> TYPE: PRT
<213> ORGANISM: Artificial Sequence
<220> FEATURE:
<223> OTHER INFORMATION: hinge

<400> SEQUENCE: 120

Glu Pro Ser Lys Tyr Gly Pro Pro His Thr Cys Pro Ser Cys Pro
1               5                   10                  15

<210> SEQ ID NO 121
<211> LENGTH: 15
<212> TYPE: PRT
<213> ORGANISM: Artificial Sequence
<220> FEATURE:
<223> OTHER INFORMATION: hinge

<400> SEQUENCE: 121

Glu Pro Ser Lys Tyr Gly Asp Lys His Thr Cys Pro Ser Cys Pro
1               5                   10                  15

<210> SEQ ID NO 122
<211> LENGTH: 15
<212> TYPE: PRT
<213> ORGANISM: Artificial Sequence
<220> FEATURE:
<223> OTHER INFORMATION: hinge

<400> SEQUENCE: 122

Glu Ser Lys Ser Tyr Gly Pro Pro Ala Ala Cys Pro Ser Cys Pro
1               5                   10                  15

<210> SEQ ID NO 123
<211> LENGTH: 15
<212> TYPE: PRT
<213> ORGANISM: Artificial Sequence
<220> FEATURE:
<223> OTHER INFORMATION: hinge

<400> SEQUENCE: 123

Glu Ser Lys Ser Tyr Gly Pro Pro Gly Gly Cys Pro Ser Cys Pro
1               5                   10                  15

<210> SEQ ID NO 124
<211> LENGTH: 15
<212> TYPE: PRT
<213> ORGANISM: Artificial Sequence
<220> FEATURE:
<223> OTHER INFORMATION: hinge

<400> SEQUENCE: 124

Glu Ser Lys Ser Tyr Gly Pro Pro His Thr Cys Pro Ser Cys Pro
1               5                   10                  15
```

```
<210> SEQ ID NO 125
<211> LENGTH: 15
<212> TYPE: PRT
<213> ORGANISM: Artificial Sequence
<220> FEATURE:
<223> OTHER INFORMATION: hinge

<400> SEQUENCE: 125

Glu Ser Lys Ser Tyr Gly Asp Lys His Thr Cys Pro Ser Cys Pro
1               5                   10                  15

<210> SEQ ID NO 126
<211> LENGTH: 13
<212> TYPE: PRT
<213> ORGANISM: Artificial Sequence
<220> FEATURE:
<223> OTHER INFORMATION: hinge

<400> SEQUENCE: 126

Glu Ser Lys Tyr Gly Pro Pro Ala Cys Pro Ser Cys Pro
1               5                   10

<210> SEQ ID NO 127
<211> LENGTH: 13
<212> TYPE: PRT
<213> ORGANISM: Artificial Sequence
<220> FEATURE:
<223> OTHER INFORMATION: hinge

<400> SEQUENCE: 127

Glu Ser Lys Tyr Gly Pro Pro Gly Cys Pro Ser Cys Pro
1               5                   10

<210> SEQ ID NO 128
<211> LENGTH: 14
<212> TYPE: PRT
<213> ORGANISM: Artificial Sequence
<220> FEATURE:
<223> OTHER INFORMATION: hinge

<400> SEQUENCE: 128

Glu Ser Lys Tyr Gly Pro Pro Thr Thr Cys Pro Ser Cys Pro
1               5                   10

<210> SEQ ID NO 129
<211> LENGTH: 14
<212> TYPE: PRT
<213> ORGANISM: Artificial Sequence
<220> FEATURE:
<223> OTHER INFORMATION: hinge

<400> SEQUENCE: 129

Glu Ser Lys Tyr Gly Asp Lys Thr Thr Cys Pro Ser Cys Pro
1               5                   10

<210> SEQ ID NO 130
<211> LENGTH: 14
<212> TYPE: PRT
<213> ORGANISM: Artificial Sequence
<220> FEATURE:
<223> OTHER INFORMATION: hinge

<400> SEQUENCE: 130

Glu Pro Ser Lys Tyr Gly Pro Pro Ala Cys Pro Ser Cys Pro
1               5                   10

<210> SEQ ID NO 131
```

```
<211> LENGTH: 14
<212> TYPE: PRT
<213> ORGANISM: Artificial Sequence
<220> FEATURE:
<223> OTHER INFORMATION: hinge

<400> SEQUENCE: 131

Glu Pro Ser Lys Tyr Gly Pro Pro Gly Cys Pro Ser Cys Pro
1               5                   10

<210> SEQ ID NO 132
<211> LENGTH: 15
<212> TYPE: PRT
<213> ORGANISM: Artificial Sequence
<220> FEATURE:
<223> OTHER INFORMATION: hinge

<400> SEQUENCE: 132

Glu Pro Ser Lys Tyr Gly Pro Pro Thr Thr Cys Pro Ser Cys Pro
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: hinge

<400> SEQUENCE: 133

Glu Pro Ser Lys Tyr Gly Asp Lys Thr Thr Cys Pro Ser Cys Pro
1               5                   10                  15

<210> SEQ ID NO 134
<211> LENGTH: 14
<212> TYPE: PRT
<213> ORGANISM: Artificial Sequence
<220> FEATURE:
<223> OTHER INFORMATION: hinge

<400> SEQUENCE: 134

Glu Ser Lys Ser Tyr Gly Pro Pro Ala Cys Pro Ser Cys Pro
1               5                   10

<210> SEQ ID NO 135
<211> LENGTH: 14
<212> TYPE: PRT
<213> ORGANISM: Artificial Sequence
<220> FEATURE:
<223> OTHER INFORMATION: hinge

<400> SEQUENCE: 135

Glu Ser Lys Ser Tyr Gly Pro Pro Gly Cys Pro Ser Cys Pro
1               5                   10

<210> SEQ ID NO 136
<211> LENGTH: 15
<212> TYPE: PRT
<213> ORGANISM: Artificial Sequence
<220> FEATURE:
<223> OTHER INFORMATION: hinge

<400> SEQUENCE: 136

Glu Ser Lys Ser Tyr Gly Pro Pro Thr Thr Cys Pro Ser Cys Pro
1               5                   10                  15

<210> SEQ ID NO 137
<211> LENGTH: 15
```

```
<212> TYPE: PRT
<213> ORGANISM: Artificial Sequence
<220> FEATURE:
<223> OTHER INFORMATION: hinge

<400> SEQUENCE: 137

Glu Ser Lys Ser Tyr Gly Asp Lys Thr Thr Cys Pro Ser Cys Pro
1               5                   10                  15

<210> SEQ ID NO 138
<211> LENGTH: 14
<212> TYPE: PRT
<213> ORGANISM: Artificial Sequence
<220> FEATURE:
<223> OTHER INFORMATION: hinge

<400> SEQUENCE: 138

Glu Ser Lys Tyr Gly Pro Pro Thr His Cys Pro Ser Cys Pro
1               5                   10

<210> SEQ ID NO 139
<211> LENGTH: 14
<212> TYPE: PRT
<213> ORGANISM: Artificial Sequence
<220> FEATURE:
<223> OTHER INFORMATION: hinge

<400> SEQUENCE: 139

Glu Ser Lys Tyr Gly Asp Lys Thr His Cys Pro Ser Cys Pro
1               5                   10

<210> SEQ ID NO 140
<211> LENGTH: 15
<212> TYPE: PRT
<213> ORGANISM: Artificial Sequence
<220> FEATURE:
<223> OTHER INFORMATION: hinge

<400> SEQUENCE: 140

Glu Pro Ser Lys Tyr Gly Pro Pro Thr His Cys Pro Ser Cys Pro
1               5                   10                  15

<210> SEQ ID NO 141
<211> LENGTH: 15
<212> TYPE: PRT
<213> ORGANISM: Artificial Sequence
<220> FEATURE:
<223> OTHER INFORMATION: hinge

<400> SEQUENCE: 141

Glu Pro Ser Lys Tyr Gly Asp Lys Thr His Cys Pro Ser Cys Pro
1               5                   10                  15

<210> SEQ ID NO 142
<211> LENGTH: 15
<212> TYPE: PRT
<213> ORGANISM: Artificial Sequence
<220> FEATURE:
<223> OTHER INFORMATION: hinge

<400> SEQUENCE: 142

Glu Ser Lys Ser Tyr Gly Pro Pro Thr His Cys Pro Ser Cys Pro
1               5                   10                  15

<210> SEQ ID NO 143
<211> LENGTH: 15
<212> TYPE: PRT
```

```
<213> ORGANISM: Artificial Sequence
<220> FEATURE:
<223> OTHER INFORMATION: hinge

<400> SEQUENCE: 143

Glu Ser Lys Ser Tyr Gly Asp Lys Thr His Cys Pro Ser Cys Pro
1               5                   10                  15

<210> SEQ ID NO 144
<211> LENGTH: 14
<212> TYPE: PRT
<213> ORGANISM: Artificial Sequence
<220> FEATURE:
<223> OTHER INFORMATION: hinge

<400> SEQUENCE: 144

Glu Ser Lys Tyr Gly Pro Pro His Thr Cys Pro Ser Cys Pro
1               5                   10

<210> SEQ ID NO 145
<211> LENGTH: 14
<212> TYPE: PRT
<213> ORGANISM: Artificial Sequence
<220> FEATURE:
<223> OTHER INFORMATION: hinge

<400> SEQUENCE: 145

Glu Ser Lys Tyr Gly Asp Lys His Thr Cys Pro Ser Cys Pro
1               5                   10

<210> SEQ ID NO 146
<211> LENGTH: 15
<212> TYPE: PRT
<213> ORGANISM: Artificial Sequence
<220> FEATURE:
<223> OTHER INFORMATION: hinge

<400> SEQUENCE: 146

Glu Pro Ser Lys Tyr Gly Pro Pro His Thr Cys Pro Ser Cys Pro
1               5                   10                  15

<210> SEQ ID NO 147
<211> LENGTH: 15
<212> TYPE: PRT
<213> ORGANISM: Artificial Sequence
<220> FEATURE:
<223> OTHER INFORMATION: hinge

<400> SEQUENCE: 147

Glu Pro Ser Lys Tyr Gly Asp Lys His Thr Cys Pro Ser Cys Pro
1               5                   10                  15

<210> SEQ ID NO 148
<211> LENGTH: 15
<212> TYPE: PRT
<213> ORGANISM: Artificial Sequence
<220> FEATURE:
<223> OTHER INFORMATION: hinge

<400> SEQUENCE: 148

Glu Ser Lys Ser Tyr Gly Pro Pro His Thr Cys Pro Ser Cys Pro
1               5                   10                  15

<210> SEQ ID NO 149
<211> LENGTH: 15
<212> TYPE: PRT
<213> ORGANISM: Artificial Sequence
```

```
<220> FEATURE:
<223> OTHER INFORMATION: hinge

<400> SEQUENCE: 149

Glu Ser Lys Ser Tyr Gly Asp Lys His Thr Cys Pro Ser Cys Pro
 1               5                  10                  15

<210> SEQ ID NO 150
<211> LENGTH: 13
<212> TYPE: PRT
<213> ORGANISM: Artificial Sequence
<220> FEATURE:
<223> OTHER INFORMATION: hinge

<400> SEQUENCE: 150

Glu Ser Lys Tyr Gly Pro Pro Thr Cys Pro Ser Cys Pro
 1               5                  10

<210> SEQ ID NO 151
<211> LENGTH: 13
<212> TYPE: PRT
<213> ORGANISM: Artificial Sequence
<220> FEATURE:
<223> OTHER INFORMATION: hinge

<400> SEQUENCE: 151

Glu Ser Lys Tyr Gly Asp Lys Thr Cys Pro Ser Cys Pro
 1               5                  10

<210> SEQ ID NO 152
<211> LENGTH: 14
<212> TYPE: PRT
<213> ORGANISM: Artificial Sequence
<220> FEATURE:
<223> OTHER INFORMATION: hinge

<400> SEQUENCE: 152

Glu Pro Ser Lys Tyr Gly Pro Pro Thr Cys Pro Ser Cys Pro
 1               5                  10

<210> SEQ ID NO 153
<211> LENGTH: 14
<212> TYPE: PRT
<213> ORGANISM: Artificial Sequence
<220> FEATURE:
<223> OTHER INFORMATION: hinge

<400> SEQUENCE: 153

Glu Pro Ser Lys Tyr Gly Asp Lys Thr Cys Pro Ser Cys Pro
 1               5                  10

<210> SEQ ID NO 154
<211> LENGTH: 14
<212> TYPE: PRT
<213> ORGANISM: Artificial Sequence
<220> FEATURE:
<223> OTHER INFORMATION: hinge

<400> SEQUENCE: 154

Glu Ser Lys Ser Tyr Gly Pro Pro Thr Cys Pro Ser Cys Pro
 1               5                  10

<210> SEQ ID NO 155
<211> LENGTH: 14
<212> TYPE: PRT
<213> ORGANISM: Artificial Sequence
<220> FEATURE:
```

```
<223> OTHER INFORMATION: hinge

<400> SEQUENCE: 155

Glu Ser Lys Ser Tyr Gly Asp Lys Thr Cys Pro Ser Cys Pro
1               5                   10

<210> SEQ ID NO 156
<211> LENGTH: 13
<212> TYPE: PRT
<213> ORGANISM: Artificial Sequence
<220> FEATURE:
<223> OTHER INFORMATION: hinge

<400> SEQUENCE: 156

Glu Ser Lys Tyr Gly Pro Pro His Cys Pro Ser Cys Pro
1               5                   10

<210> SEQ ID NO 157
<211> LENGTH: 13
<212> TYPE: PRT
<213> ORGANISM: Artificial Sequence
<220> FEATURE:
<223> OTHER INFORMATION: hinge

<400> SEQUENCE: 157

Glu Ser Lys Tyr Gly Asp Lys His Cys Pro Ser Cys Pro
1               5                   10

<210> SEQ ID NO 158
<211> LENGTH: 14
<212> TYPE: PRT
<213> ORGANISM: Artificial Sequence
<220> FEATURE:
<223> OTHER INFORMATION: hinge

<400> SEQUENCE: 158

Glu Pro Ser Lys Tyr Gly Pro Pro His Cys Pro Ser Cys Pro
1               5                   10

<210> SEQ ID NO 159
<211> LENGTH: 14
<212> TYPE: PRT
<213> ORGANISM: Artificial Sequence
<220> FEATURE:
<223> OTHER INFORMATION: hinge

<400> SEQUENCE: 159

Glu Pro Ser Lys Tyr Gly Asp Lys His Cys Pro Ser Cys Pro
1               5                   10

<210> SEQ ID NO 160
<211> LENGTH: 14
<212> TYPE: PRT
<213> ORGANISM: Artificial Sequence
<220> FEATURE:
<223> OTHER INFORMATION: hinge

<400> SEQUENCE: 160

Glu Ser Lys Ser Tyr Gly Pro Pro His Cys Pro Ser Cys Pro
1               5                   10

<210> SEQ ID NO 161
<211> LENGTH: 14
<212> TYPE: PRT
<213> ORGANISM: Artificial Sequence
<220> FEATURE:
<223> OTHER INFORMATION: hinge
```

<400> SEQUENCE: 161

Glu Pro Lys Ser Cys Asp Lys Ala Ala Cys Pro Pro Cys Pro
1               5                   10

<210> SEQ ID NO 162
<211> LENGTH: 14
<212> TYPE: PRT
<213> ORGANISM: Artificial Sequence
<220> FEATURE:
<223> OTHER INFORMATION: hinge

<400> SEQUENCE: 162

Glu Pro Lys Ser Cys Asp Lys Ala Ala Cys Pro Pro Cys Pro
1               5                   10

<210> SEQ ID NO 163
<211> LENGTH: 14
<212> TYPE: PRT
<213> ORGANISM: Artificial Sequence
<220> FEATURE:
<223> OTHER INFORMATION: hinge

<400> SEQUENCE: 163

Glu Pro Lys Ser Cys Asp Lys Gly Gly Cys Pro Pro Cys Pro
1               5                   10

<210> SEQ ID NO 164
<211> LENGTH: 14
<212> TYPE: PRT
<213> ORGANISM: Artificial Sequence
<220> FEATURE:
<223> OTHER INFORMATION: hinge

<400> SEQUENCE: 164

Glu Pro Lys Ser Cys Asp Lys His Thr Ser Pro Pro Cys Pro
1               5                   10

<210> SEQ ID NO 165
<211> LENGTH: 14
<212> TYPE: PRT
<213> ORGANISM: Artificial Sequence
<220> FEATURE:
<223> OTHER INFORMATION: hinge

<400> SEQUENCE: 165

Glu Pro Lys Ser Cys Asp Lys His Thr Cys Pro Pro Ser Pro
1               5                   10

<210> SEQ ID NO 166
<211> LENGTH: 14
<212> TYPE: PRT
<213> ORGANISM: Artificial Sequence
<220> FEATURE:
<223> OTHER INFORMATION: hinge

<400> SEQUENCE: 166

Glu Pro Lys Ser Cys Asp Lys His Thr Ser Pro Pro Ser Pro
1               5                   10

<210> SEQ ID NO 167
<211> LENGTH: 14
<212> TYPE: PRT
<213> ORGANISM: Artificial Sequence
<220> FEATURE:
<223> OTHER INFORMATION: hinge

<400> SEQUENCE: 167

Glu Pro Lys Ser Cys Asp Lys Ala Ala Ser Pro Pro Cys Pro
1               5                   10

<210> SEQ ID NO 168
<211> LENGTH: 14
<212> TYPE: PRT
<213> ORGANISM: Artificial Sequence
<220> FEATURE:
<223> OTHER INFORMATION: hinge

<400> SEQUENCE: 168

Glu Pro Lys Ser Cys Asp Lys Ala Ala Cys Pro Pro Ser Pro
1               5                   10

<210> SEQ ID NO 169
<211> LENGTH: 14
<212> TYPE: PRT
<213> ORGANISM: Artificial Sequence
<220> FEATURE:
<223> OTHER INFORMATION: hinge

<400> SEQUENCE: 169

Glu Pro Lys Ser Cys Asp Lys Ala Ala Ser Pro Pro Ser Pro
1               5                   10

<210> SEQ ID NO 170
<211> LENGTH: 14
<212> TYPE: PRT
<213> ORGANISM: Artificial Sequence
<220> FEATURE:
<223> OTHER INFORMATION: hinge

<400> SEQUENCE: 170

Glu Pro Lys Ser Cys Asp Lys Gly Gly Ser Pro Pro Cys Pro
1               5                   10

<210> SEQ ID NO 171
<211> LENGTH: 14
<212> TYPE: PRT
<213> ORGANISM: Artificial Sequence
<220> FEATURE:
<223> OTHER INFORMATION: hinge

<400> SEQUENCE: 171

Glu Pro Lys Ser Cys Asp Lys Gly Gly Cys Pro Pro Ser Pro
1               5                   10

<210> SEQ ID NO 172
<211> LENGTH: 14
<212> TYPE: PRT
<213> ORGANISM: Artificial Sequence
<220> FEATURE:
<223> OTHER INFORMATION: hinge

<400> SEQUENCE: 172

Glu Pro Lys Ser Cys Asp Lys Gly Gly Ser Pro Pro Ser Pro
1               5                   10

<210> SEQ ID NO 173
<211> LENGTH: 13
<212> TYPE: PRT
<213> ORGANISM: Artificial Sequence
<220> FEATURE:
<223> OTHER INFORMATION: hinge

<400> SEQUENCE: 173

```
Glu Pro Lys Ser Cys Asp Lys Ala Cys Pro Pro Cys Pro
1               5                   10

<210> SEQ ID NO 174
<211> LENGTH: 13
<212> TYPE: PRT
<213> ORGANISM: Artificial Sequence
<220> FEATURE:
<223> OTHER INFORMATION: hinge

<400> SEQUENCE: 174

Glu Pro Lys Ser Cys Asp Lys Gly Cys Pro Pro Cys Pro
1               5                   10

<210> SEQ ID NO 175
<211> LENGTH: 13
<212> TYPE: PRT
<213> ORGANISM: Artificial Sequence
<220> FEATURE:
<223> OTHER INFORMATION: hinge

<400> SEQUENCE: 175

Glu Pro Lys Ser Cys Asp Lys Thr Ser Pro Pro Cys Pro
1               5                   10

<210> SEQ ID NO 176
<211> LENGTH: 13
<212> TYPE: PRT
<213> ORGANISM: Artificial Sequence
<220> FEATURE:
<223> OTHER INFORMATION: hinge

<400> SEQUENCE: 176

Glu Pro Lys Ser Cys Asp Lys Thr Cys Pro Pro Ser Pro
1               5                   10

<210> SEQ ID NO 177
<211> LENGTH: 13
<212> TYPE: PRT
<213> ORGANISM: Artificial Sequence
<220> FEATURE:
<223> OTHER INFORMATION: hinge

<400> SEQUENCE: 177

Glu Pro Lys Ser Cys Asp Lys Thr Ser Pro Pro Ser Pro
1               5                   10

<210> SEQ ID NO 178
<211> LENGTH: 13
<212> TYPE: PRT
<213> ORGANISM: Artificial Sequence
<220> FEATURE:
<223> OTHER INFORMATION: hinge

<400> SEQUENCE: 178

Glu Pro Lys Ser Cys Asp Lys Ala Ser Pro Pro Cys Pro
1               5                   10

<210> SEQ ID NO 179
<211> LENGTH: 13
<212> TYPE: PRT
<213> ORGANISM: Artificial Sequence
<220> FEATURE:
<223> OTHER INFORMATION: hinge

<400> SEQUENCE: 179
```

Glu Pro Lys Ser Cys Asp Lys Ala Cys Pro Pro Ser Pro
1               5                   10

<210> SEQ ID NO 180
<211> LENGTH: 13
<212> TYPE: PRT
<213> ORGANISM: Artificial Sequence
<220> FEATURE:
<223> OTHER INFORMATION: hinge

<400> SEQUENCE: 180

Glu Pro Lys Ser Cys Asp Lys Ala Ser Pro Pro Ser Pro
1               5                   10

<210> SEQ ID NO 181
<211> LENGTH: 13
<212> TYPE: PRT
<213> ORGANISM: Artificial Sequence
<220> FEATURE:
<223> OTHER INFORMATION: hinge

<400> SEQUENCE: 181

Glu Pro Lys Ser Cys Asp Lys Gly Ser Pro Pro Cys Pro
1               5                   10

<210> SEQ ID NO 182
<211> LENGTH: 13
<212> TYPE: PRT
<213> ORGANISM: Artificial Sequence
<220> FEATURE:
<223> OTHER INFORMATION: hinge

<400> SEQUENCE: 182

Glu Pro Lys Ser Cys Asp Lys Gly Cys Pro Pro Ser Pro
1               5                   10

<210> SEQ ID NO 183
<211> LENGTH: 13
<212> TYPE: PRT
<213> ORGANISM: Artificial Sequence
<220> FEATURE:
<223> OTHER INFORMATION: hinge

<400> SEQUENCE: 183

Glu Pro Lys Ser Cys Asp Lys Gly Ser Pro Pro Ser Pro
1               5                   10

<210> SEQ ID NO 184
<211> LENGTH: 12
<212> TYPE: PRT
<213> ORGANISM: Artificial Sequence
<220> FEATURE:
<223> OTHER INFORMATION: hinge

<400> SEQUENCE: 184

Glu Pro Lys Ser Cys Asp Lys Cys Pro Pro Cys Pro
1               5                   10

<210> SEQ ID NO 185
<211> LENGTH: 12
<212> TYPE: PRT
<213> ORGANISM: Artificial Sequence
<220> FEATURE:
<223> OTHER INFORMATION: hinge

<400> SEQUENCE: 185

Glu Pro Lys Ser Cys Asp Lys Cys Pro Pro Cys Pro

```
1               5                   10
```

<210> SEQ ID NO 186
<211> LENGTH: 12
<212> TYPE: PRT
<213> ORGANISM: Artificial Sequence
<220> FEATURE:
<223> OTHER INFORMATION: hinge

<400> SEQUENCE: 186

```
Glu Pro Lys Ser Cys Asp Lys Ser Pro Pro Cys Pro
1               5                   10
```

<210> SEQ ID NO 187
<211> LENGTH: 12
<212> TYPE: PRT
<213> ORGANISM: Artificial Sequence
<220> FEATURE:
<223> OTHER INFORMATION: hinge

<400> SEQUENCE: 187

```
Glu Pro Lys Ser Cys Asp Lys Cys Pro Pro Ser Pro
1               5                   10
```

<210> SEQ ID NO 188
<211> LENGTH: 12
<212> TYPE: PRT
<213> ORGANISM: Artificial Sequence
<220> FEATURE:
<223> OTHER INFORMATION: hinge

<400> SEQUENCE: 188

```
Glu Pro Lys Ser Cys Asp Lys Ser Pro Pro Ser Pro
1               5                   10
```

<210> SEQ ID NO 189
<211> LENGTH: 12
<212> TYPE: PRT
<213> ORGANISM: Artificial Sequence
<220> FEATURE:
<223> OTHER INFORMATION: hinge

<400> SEQUENCE: 189

```
Glu Pro Lys Ser Cys Asp Lys Ser Pro Pro Cys Pro
1               5                   10
```

<210> SEQ ID NO 190
<211> LENGTH: 12
<212> TYPE: PRT
<213> ORGANISM: Artificial Sequence
<220> FEATURE:
<223> OTHER INFORMATION: hinge

<400> SEQUENCE: 190

```
Glu Pro Lys Ser Cys Asp Lys Cys Pro Pro Ser Pro
1               5                   10
```

<210> SEQ ID NO 191
<211> LENGTH: 12
<212> TYPE: PRT
<213> ORGANISM: Artificial Sequence
<220> FEATURE:
<223> OTHER INFORMATION: hinge

<400> SEQUENCE: 191

```
Glu Pro Lys Ser Cys Asp Lys Ser Pro Pro Ser Pro
1               5                   10
```

```
<210> SEQ ID NO 192
<211> LENGTH: 12
<212> TYPE: PRT
<213> ORGANISM: Artificial Sequence
<220> FEATURE:
<223> OTHER INFORMATION: hinge

<400> SEQUENCE: 192

Glu Pro Lys Ser Cys Asp Lys Ser Pro Pro Cys Pro
1               5                   10

<210> SEQ ID NO 193
<211> LENGTH: 12
<212> TYPE: PRT
<213> ORGANISM: Artificial Sequence
<220> FEATURE:
<223> OTHER INFORMATION: hinge

<400> SEQUENCE: 193

Glu Pro Lys Ser Cys Asp Lys Cys Pro Pro Ser Pro
1               5                   10

<210> SEQ ID NO 194
<211> LENGTH: 12
<212> TYPE: PRT
<213> ORGANISM: Artificial Sequence
<220> FEATURE:
<223> OTHER INFORMATION: hinge

<400> SEQUENCE: 194

Glu Pro Lys Ser Cys Asp Lys Ser Pro Pro Ser Pro
1               5                   10

<210> SEQ ID NO 195
<211> LENGTH: 14
<212> TYPE: PRT
<213> ORGANISM: Artificial Sequence
<220> FEATURE:
<223> OTHER INFORMATION: hinge

<400> SEQUENCE: 195

Glu Pro Lys Ser Cys Asp Lys Thr Thr Ser Pro Pro Cys Pro
1               5                   10

<210> SEQ ID NO 196
<211> LENGTH: 14
<212> TYPE: PRT
<213> ORGANISM: Artificial Sequence
<220> FEATURE:
<223> OTHER INFORMATION: hinge

<400> SEQUENCE: 196

Glu Pro Lys Ser Cys Asp Lys Thr Thr Cys Pro Pro Ser Pro
1               5                   10

<210> SEQ ID NO 197
<211> LENGTH: 14
<212> TYPE: PRT
<213> ORGANISM: Artificial Sequence
<220> FEATURE:
<223> OTHER INFORMATION: hinge

<400> SEQUENCE: 197

Glu Pro Lys Ser Cys Asp Lys Thr Thr Ser Pro Pro Ser Pro
1               5                   10
```

<210> SEQ ID NO 198
<211> LENGTH: 14
<212> TYPE: PRT
<213> ORGANISM: Artificial Sequence
<220> FEATURE:
<223> OTHER INFORMATION: hinge

<400> SEQUENCE: 198

Glu Pro Lys Ser Cys Asp Lys Thr His Ser Pro Pro Cys Pro
1               5                   10

<210> SEQ ID NO 199
<211> LENGTH: 14
<212> TYPE: PRT
<213> ORGANISM: Artificial Sequence
<220> FEATURE:
<223> OTHER INFORMATION: hinge

<400> SEQUENCE: 199

Glu Pro Lys Ser Cys Asp Lys Thr His Cys Pro Pro Ser Pro
1               5                   10

<210> SEQ ID NO 200
<211> LENGTH: 14
<212> TYPE: PRT
<213> ORGANISM: Artificial Sequence
<220> FEATURE:
<223> OTHER INFORMATION: hinge

<400> SEQUENCE: 200

Glu Pro Lys Ser Cys Asp Lys Thr His Ser Pro Pro Ser Pro
1               5                   10

<210> SEQ ID NO 201
<211> LENGTH: 12
<212> TYPE: PRT
<213> ORGANISM: Artificial Sequence
<220> FEATURE:
<223> OTHER INFORMATION: hinge

<400> SEQUENCE: 201

Glu Ser Lys Tyr Gly Pro Pro Cys Pro Pro Cys Pro
1               5                   10

<210> SEQ ID NO 202
<211> LENGTH: 12
<212> TYPE: PRT
<213> ORGANISM: Artificial Sequence
<220> FEATURE:
<223> OTHER INFORMATION: hinge

<400> SEQUENCE: 202

Glu Ser Lys Tyr Gly Pro Pro Cys Pro Pro Cys Pro
1               5                   10

<210> SEQ ID NO 203
<211> LENGTH: 12
<212> TYPE: PRT
<213> ORGANISM: Artificial Sequence
<220> FEATURE:
<223> OTHER INFORMATION: hinge

<400> SEQUENCE: 203

Glu Ser Lys Tyr Gly Pro Pro Cys Pro Pro Cys Pro
1               5                   10

```
<210> SEQ ID NO 204
<211> LENGTH: 12
<212> TYPE: PRT
<213> ORGANISM: Artificial Sequence
<220> FEATURE:
<223> OTHER INFORMATION: hinge

<400> SEQUENCE: 204

Glu Ser Lys Tyr Gly Asp Lys Cys Pro Pro Cys Pro
1               5                   10

<210> SEQ ID NO 205
<211> LENGTH: 13
<212> TYPE: PRT
<213> ORGANISM: Artificial Sequence
<220> FEATURE:
<223> OTHER INFORMATION: hinge

<400> SEQUENCE: 205

Glu Pro Ser Lys Tyr Gly Pro Pro Cys Pro Pro Cys Pro
1               5                   10

<210> SEQ ID NO 206
<211> LENGTH: 13
<212> TYPE: PRT
<213> ORGANISM: Artificial Sequence
<220> FEATURE:
<223> OTHER INFORMATION: hinge

<400> SEQUENCE: 206

Glu Pro Ser Lys Tyr Gly Pro Pro Cys Pro Pro Cys Pro
1               5                   10

<210> SEQ ID NO 207
<211> LENGTH: 13
<212> TYPE: PRT
<213> ORGANISM: Artificial Sequence
<220> FEATURE:
<223> OTHER INFORMATION: hinge

<400> SEQUENCE: 207

Glu Pro Ser Lys Tyr Gly Pro Pro Cys Pro Pro Cys Pro
1               5                   10

<210> SEQ ID NO 208
<211> LENGTH: 13
<212> TYPE: PRT
<213> ORGANISM: Artificial Sequence
<220> FEATURE:
<223> OTHER INFORMATION: hinge

<400> SEQUENCE: 208

Glu Pro Ser Lys Tyr Gly Asp Lys Cys Pro Pro Cys Pro
1               5                   10

<210> SEQ ID NO 209
<211> LENGTH: 13
<212> TYPE: PRT
<213> ORGANISM: Artificial Sequence
<220> FEATURE:
<223> OTHER INFORMATION: hinge

<400> SEQUENCE: 209

Glu Ser Lys Ser Tyr Gly Pro Pro Cys Pro Pro Cys Pro
1               5                   10

<210> SEQ ID NO 210
```

<211> LENGTH: 13
<212> TYPE: PRT
<213> ORGANISM: Artificial Sequence
<220> FEATURE:
<223> OTHER INFORMATION: hinge

<400> SEQUENCE: 210

Glu Ser Lys Ser Tyr Gly Pro Pro Cys Pro Pro Cys Pro
1               5                   10

<210> SEQ ID NO 211
<211> LENGTH: 13
<212> TYPE: PRT
<213> ORGANISM: Artificial Sequence
<220> FEATURE:
<223> OTHER INFORMATION: hinge

<400> SEQUENCE: 211

Glu Ser Lys Ser Tyr Gly Pro Pro Cys Pro Pro Cys Pro
1               5                   10

<210> SEQ ID NO 212
<211> LENGTH: 13
<212> TYPE: PRT
<213> ORGANISM: Artificial Sequence
<220> FEATURE:
<223> OTHER INFORMATION: hinge

<400> SEQUENCE: 212

Glu Ser Lys Ser Tyr Gly Asp Lys Cys Pro Pro Cys Pro
1               5                   10

<210> SEQ ID NO 213
<211> LENGTH: 14
<212> TYPE: PRT
<213> ORGANISM: Artificial Sequence
<220> FEATURE:
<223> OTHER INFORMATION: hinge

<400> SEQUENCE: 213

Glu Ser Lys Tyr Gly Pro Pro Ala Ala Cys Pro Pro Cys Pro
1               5                   10

<210> SEQ ID NO 214
<211> LENGTH: 14
<212> TYPE: PRT
<213> ORGANISM: Artificial Sequence
<220> FEATURE:
<223> OTHER INFORMATION: hinge

<400> SEQUENCE: 214

Glu Ser Lys Tyr Gly Pro Pro Gly Gly Cys Pro Pro Cys Pro
1               5                   10

<210> SEQ ID NO 215
<211> LENGTH: 14
<212> TYPE: PRT
<213> ORGANISM: Artificial Sequence
<220> FEATURE:
<223> OTHER INFORMATION: hinge

<400> SEQUENCE: 215

Glu Ser Lys Tyr Gly Pro Pro His Thr Cys Pro Pro Cys Pro
1               5                   10

<210> SEQ ID NO 216
<211> LENGTH: 14

```
<212> TYPE: PRT
<213> ORGANISM: Artificial Sequence
<220> FEATURE:
<223> OTHER INFORMATION: hinge

<400> SEQUENCE: 216

Glu Ser Lys Tyr Gly Asp Lys His Thr Cys Pro Pro Cys Pro
1               5                   10

<210> SEQ ID NO 217
<211> LENGTH: 15
<212> TYPE: PRT
<213> ORGANISM: Artificial Sequence
<220> FEATURE:
<223> OTHER INFORMATION: hinge

<400> SEQUENCE: 217

Glu Pro Ser Lys Tyr Gly Pro Pro Ala Ala Cys Pro Pro Cys Pro
1               5                   10                  15

<210> SEQ ID NO 218
<211> LENGTH: 15
<212> TYPE: PRT
<213> ORGANISM: Artificial Sequence
<220> FEATURE:
<223> OTHER INFORMATION: hinge

<400> SEQUENCE: 218

Glu Pro Ser Lys Tyr Gly Pro Pro Gly Gly Cys Pro Pro Cys Pro
1               5                   10                  15

<210> SEQ ID NO 219
<211> LENGTH: 15
<212> TYPE: PRT
<213> ORGANISM: Artificial Sequence
<220> FEATURE:
<223> OTHER INFORMATION: hinge

<400> SEQUENCE: 219

Glu Pro Ser Lys Tyr Gly Pro Pro His Thr Cys Pro Pro Cys Pro
1               5                   10                  15

<210> SEQ ID NO 220
<211> LENGTH: 15
<212> TYPE: PRT
<213> ORGANISM: Artificial Sequence
<220> FEATURE:
<223> OTHER INFORMATION: hinge

<400> SEQUENCE: 220

Glu Pro Ser Lys Tyr Gly Asp Lys His Thr Cys Pro Pro Cys Pro
1               5                   10                  15

<210> SEQ ID NO 221
<211> LENGTH: 15
<212> TYPE: PRT
<213> ORGANISM: Artificial Sequence
<220> FEATURE:
<223> OTHER INFORMATION: hinge

<400> SEQUENCE: 221

Glu Ser Lys Ser Tyr Gly Pro Pro Ala Ala Cys Pro Pro Cys Pro
1               5                   10                  15

<210> SEQ ID NO 222
<211> LENGTH: 15
<212> TYPE: PRT
```

```
<213> ORGANISM: Artificial Sequence
<220> FEATURE:
<223> OTHER INFORMATION: hinge

<400> SEQUENCE: 222

Glu Ser Lys Ser Tyr Gly Pro Pro Gly Cys Pro Pro Cys Pro
1               5                   10                  15

<210> SEQ ID NO 223
<211> LENGTH: 15
<212> TYPE: PRT
<213> ORGANISM: Artificial Sequence
<220> FEATURE:
<223> OTHER INFORMATION: hinge

<400> SEQUENCE: 223

Glu Ser Lys Ser Tyr Gly Pro Pro His Thr Cys Pro Pro Cys Pro
1               5                   10                  15

<210> SEQ ID NO 224
<211> LENGTH: 15
<212> TYPE: PRT
<213> ORGANISM: Artificial Sequence
<220> FEATURE:
<223> OTHER INFORMATION: hinge

<400> SEQUENCE: 224

Glu Ser Lys Ser Tyr Gly Asp Lys His Thr Cys Pro Pro Cys Pro
1               5                   10                  15

<210> SEQ ID NO 225
<211> LENGTH: 13
<212> TYPE: PRT
<213> ORGANISM: Artificial Sequence
<220> FEATURE:
<223> OTHER INFORMATION: hinge

<400> SEQUENCE: 225

Glu Ser Lys Tyr Gly Pro Pro Ala Cys Pro Pro Cys Pro
1               5                   10

<210> SEQ ID NO 226
<211> LENGTH: 13
<212> TYPE: PRT
<213> ORGANISM: Artificial Sequence
<220> FEATURE:
<223> OTHER INFORMATION: hinge

<400> SEQUENCE: 226

Glu Ser Lys Tyr Gly Pro Pro Gly Cys Pro Pro Cys Pro
1               5                   10

<210> SEQ ID NO 227
<211> LENGTH: 14
<212> TYPE: PRT
<213> ORGANISM: Artificial Sequence
<220> FEATURE:
<223> OTHER INFORMATION: hinge

<400> SEQUENCE: 227

Glu Ser Lys Tyr Gly Pro Pro Thr Thr Cys Pro Pro Cys Pro
1               5                   10

<210> SEQ ID NO 228
<211> LENGTH: 14
<212> TYPE: PRT
<213> ORGANISM: Artificial Sequence
```

-continued

```
<220> FEATURE:
<223> OTHER INFORMATION: Hinge Sequence

<400> SEQUENCE: 228

Glu Ser Lys Tyr Gly Asp Lys Thr Cys Pro Pro Cys Pro
1               5                   10

<210> SEQ ID NO 229
<211> LENGTH: 14
<212> TYPE: PRT
<213> ORGANISM: Artificial Sequence
<220> FEATURE:
<223> OTHER INFORMATION: hinge

<400> SEQUENCE: 229

Glu Pro Ser Lys Tyr Gly Pro Pro Ala Cys Pro Pro Cys Pro
1               5                   10

<210> SEQ ID NO 230
<211> LENGTH: 14
<212> TYPE: PRT
<213> ORGANISM: Artificial Sequence
<220> FEATURE:
<223> OTHER INFORMATION: hinge

<400> SEQUENCE: 230

Glu Pro Ser Lys Tyr Gly Pro Pro Gly Cys Pro Pro Cys Pro
1               5                   10

<210> SEQ ID NO 231
<211> LENGTH: 15
<212> TYPE: PRT
<213> ORGANISM: Artificial Sequence
<220> FEATURE:
<223> OTHER INFORMATION: hinge

<400> SEQUENCE: 231

Glu Pro Ser Lys Tyr Gly Pro Pro Thr Thr Cys Pro Pro Cys Pro
1               5                   10                  15

<210> SEQ ID NO 232
<211> LENGTH: 15
<212> TYPE: PRT
<213> ORGANISM: Artificial Sequence
<220> FEATURE:
<223> OTHER INFORMATION: hinge

<400> SEQUENCE: 232

Glu Pro Ser Lys Tyr Gly Asp Lys Thr Thr Cys Pro Pro Cys Pro
1               5                   10                  15

<210> SEQ ID NO 233
<211> LENGTH: 14
<212> TYPE: PRT
<213> ORGANISM: Artificial Sequence
<220> FEATURE:
<223> OTHER INFORMATION: hinge

<400> SEQUENCE: 233

Glu Ser Lys Ser Tyr Gly Pro Pro Ala Cys Pro Pro Cys Pro
1               5                   10

<210> SEQ ID NO 234
<211> LENGTH: 14
<212> TYPE: PRT
<213> ORGANISM: Artificial Sequence
<220> FEATURE:
```

```
<223> OTHER INFORMATION: hinge

<400> SEQUENCE: 234

Glu Ser Lys Ser Tyr Gly Pro Pro Gly Cys Pro Pro Cys Pro
1               5                   10

<210> SEQ ID NO 235
<211> LENGTH: 15
<212> TYPE: PRT
<213> ORGANISM: Artificial Sequence
<220> FEATURE:
<223> OTHER INFORMATION: hinge

<400> SEQUENCE: 235

Glu Ser Lys Ser Tyr Gly Pro Pro Thr Thr Cys Pro Pro Cys Pro
1               5                   10                  15

<210> SEQ ID NO 236
<211> LENGTH: 15
<212> TYPE: PRT
<213> ORGANISM: Artificial Sequence
<220> FEATURE:
<223> OTHER INFORMATION: hinge

<400> SEQUENCE: 236

Glu Ser Lys Ser Tyr Gly Asp Lys Thr Thr Cys Pro Pro Cys Pro
1               5                   10                  15

<210> SEQ ID NO 237
<211> LENGTH: 14
<212> TYPE: PRT
<213> ORGANISM: Artificial Sequence
<220> FEATURE:
<223> OTHER INFORMATION: hinge

<400> SEQUENCE: 237

Glu Ser Lys Tyr Gly Pro Pro Thr His Cys Pro Pro Cys Pro
1               5                   10

<210> SEQ ID NO 238
<211> LENGTH: 14
<212> TYPE: PRT
<213> ORGANISM: Artificial Sequence
<220> FEATURE:
<223> OTHER INFORMATION: hinge

<400> SEQUENCE: 238

Glu Ser Lys Tyr Gly Asp Lys Thr His Cys Pro Pro Cys Pro
1               5                   10

<210> SEQ ID NO 239
<211> LENGTH: 15
<212> TYPE: PRT
<213> ORGANISM: Artificial Sequence
<220> FEATURE:
<223> OTHER INFORMATION: hinge

<400> SEQUENCE: 239

Glu Pro Ser Lys Tyr Gly Pro Pro Thr His Cys Pro Pro Cys Pro
1               5                   10                  15

<210> SEQ ID NO 240
<211> LENGTH: 15
<212> TYPE: PRT
<213> ORGANISM: Artificial Sequence
<220> FEATURE:
<223> OTHER INFORMATION: hinge
```

<400> SEQUENCE: 240

Glu Pro Ser Lys Tyr Gly Asp Lys Thr His Cys Pro Pro Cys Pro
1               5                   10                  15

<210> SEQ ID NO 241
<211> LENGTH: 15
<212> TYPE: PRT
<213> ORGANISM: Artificial Sequence
<220> FEATURE:
<223> OTHER INFORMATION: hinge

<400> SEQUENCE: 241

Glu Ser Lys Ser Tyr Gly Pro Pro Thr His Cys Pro Pro Cys Pro
1               5                   10                  15

<210> SEQ ID NO 242
<211> LENGTH: 15
<212> TYPE: PRT
<213> ORGANISM: Artificial Sequence
<220> FEATURE:
<223> OTHER INFORMATION: hinge

<400> SEQUENCE: 242

Glu Ser Lys Ser Tyr Gly Asp Lys Thr His Cys Pro Pro Cys Pro
1               5                   10                  15

<210> SEQ ID NO 243
<211> LENGTH: 14
<212> TYPE: PRT
<213> ORGANISM: Artificial Sequence
<220> FEATURE:
<223> OTHER INFORMATION: hinge

<400> SEQUENCE: 243

Glu Ser Lys Tyr Gly Pro Pro His Thr Cys Pro Pro Cys Pro
1               5                   10

<210> SEQ ID NO 244
<211> LENGTH: 14
<212> TYPE: PRT
<213> ORGANISM: Artificial Sequence
<220> FEATURE:
<223> OTHER INFORMATION: hinge

<400> SEQUENCE: 244

Glu Ser Lys Tyr Gly Asp Lys His Thr Cys Pro Pro Cys Pro
1               5                   10

<210> SEQ ID NO 245
<211> LENGTH: 15
<212> TYPE: PRT
<213> ORGANISM: Artificial Sequence
<220> FEATURE:
<223> OTHER INFORMATION: hinge

<400> SEQUENCE: 245

Glu Pro Ser Lys Tyr Gly Pro Pro His Thr Cys Pro Pro Cys Pro
1               5                   10                  15

<210> SEQ ID NO 246
<211> LENGTH: 15
<212> TYPE: PRT
<213> ORGANISM: Artificial Sequence
<220> FEATURE:
<223> OTHER INFORMATION: hinge

```
<400> SEQUENCE: 246

Glu Pro Ser Lys Tyr Gly Asp Lys His Thr Cys Pro Pro Cys Pro
1               5                   10                  15

<210> SEQ ID NO 247
<211> LENGTH: 15
<212> TYPE: PRT
<213> ORGANISM: Artificial Sequence
<220> FEATURE:
<223> OTHER INFORMATION: hinge

<400> SEQUENCE: 247

Glu Ser Lys Ser Tyr Gly Pro Pro His Thr Cys Pro Pro Cys Pro
1               5                   10                  15

<210> SEQ ID NO 248
<211> LENGTH: 15
<212> TYPE: PRT
<213> ORGANISM: Artificial Sequence
<220> FEATURE:
<223> OTHER INFORMATION: hinge

<400> SEQUENCE: 248

Glu Ser Lys Ser Tyr Gly Asp Lys His Thr Cys Pro Pro Cys Pro
1               5                   10                  15

<210> SEQ ID NO 249
<211> LENGTH: 13
<212> TYPE: PRT
<213> ORGANISM: Artificial Sequence
<220> FEATURE:
<223> OTHER INFORMATION: hinge

<400> SEQUENCE: 249

Glu Ser Lys Tyr Gly Pro Pro Thr Cys Pro Pro Cys Pro
1               5                   10

<210> SEQ ID NO 250
<211> LENGTH: 13
<212> TYPE: PRT
<213> ORGANISM: Artificial Sequence
<220> FEATURE:
<223> OTHER INFORMATION: hinge

<400> SEQUENCE: 250

Glu Ser Lys Tyr Gly Asp Lys Thr Cys Pro Pro Cys Pro
1               5                   10

<210> SEQ ID NO 251
<211> LENGTH: 14
<212> TYPE: PRT
<213> ORGANISM: Artificial Sequence
<220> FEATURE:
<223> OTHER INFORMATION: hinge

<400> SEQUENCE: 251

Glu Pro Ser Lys Tyr Gly Pro Pro Thr Cys Pro Pro Cys Pro
1               5                   10

<210> SEQ ID NO 252
<211> LENGTH: 14
<212> TYPE: PRT
<213> ORGANISM: Artificial Sequence
<220> FEATURE:
<223> OTHER INFORMATION: hinge

<400> SEQUENCE: 252
```

```
Glu Pro Ser Lys Tyr Gly Asp Lys Thr Cys Pro Pro Cys Pro
1               5                   10

<210> SEQ ID NO 253
<211> LENGTH: 14
<212> TYPE: PRT
<213> ORGANISM: Artificial Sequence
<220> FEATURE:
<223> OTHER INFORMATION: hinge

<400> SEQUENCE: 253

Glu Ser Lys Ser Tyr Gly Pro Pro Thr Cys Pro Pro Cys Pro
1               5                   10

<210> SEQ ID NO 254
<211> LENGTH: 14
<212> TYPE: PRT
<213> ORGANISM: Artificial Sequence
<220> FEATURE:
<223> OTHER INFORMATION: hinge

<400> SEQUENCE: 254

Glu Ser Lys Ser Tyr Gly Asp Lys Thr Cys Pro Pro Cys Pro
1               5                   10

<210> SEQ ID NO 255
<211> LENGTH: 13
<212> TYPE: PRT
<213> ORGANISM: Artificial Sequence
<220> FEATURE:
<223> OTHER INFORMATION: hinge

<400> SEQUENCE: 255

Glu Ser Lys Tyr Gly Pro Pro His Cys Pro Pro Cys Pro
1               5                   10

<210> SEQ ID NO 256
<211> LENGTH: 13
<212> TYPE: PRT
<213> ORGANISM: Artificial Sequence
<220> FEATURE:
<223> OTHER INFORMATION: hinge

<400> SEQUENCE: 256

Glu Ser Lys Tyr Gly Asp Lys His Cys Pro Pro Cys Pro
1               5                   10

<210> SEQ ID NO 257
<211> LENGTH: 14
<212> TYPE: PRT
<213> ORGANISM: Artificial Sequence
<220> FEATURE:
<223> OTHER INFORMATION: hinge

<400> SEQUENCE: 257

Glu Pro Ser Lys Tyr Gly Pro Pro His Cys Pro Pro Cys Pro
1               5                   10

<210> SEQ ID NO 258
<211> LENGTH: 14
<212> TYPE: PRT
<213> ORGANISM: Artificial Sequence
<220> FEATURE:
<223> OTHER INFORMATION: hinge

<400> SEQUENCE: 258
```

```
Glu Pro Ser Lys Tyr Gly Asp Lys His Cys Pro Pro Cys Pro
1               5                   10
```

<210> SEQ ID NO 259
<211> LENGTH: 14
<212> TYPE: PRT
<213> ORGANISM: Artificial Sequence
<220> FEATURE:
<223> OTHER INFORMATION: hinge

<400> SEQUENCE: 259

```
Glu Ser Lys Ser Tyr Gly Pro Pro His Cys Pro Pro Cys Pro
1               5                   10
```

<210> SEQ ID NO 260
<211> LENGTH: 14
<212> TYPE: PRT
<213> ORGANISM: Artificial Sequence
<220> FEATURE:
<223> OTHER INFORMATION: hinge

<400> SEQUENCE: 260

```
Glu Ser Lys Ser Tyr Gly Asp Lys His Cys Pro Pro Cys Pro
1               5                   10
```

<210> SEQ ID NO 261
<211> LENGTH: 15
<212> TYPE: PRT
<213> ORGANISM: Artificial Sequence
<220> FEATURE:
<223> OTHER INFORMATION: hinge

<400> SEQUENCE: 261

```
Glu Pro Lys Ser Cys Asp Lys Thr His Thr Cys Pro Pro Cys Pro
1               5                   10                  15
```

<210> SEQ ID NO 262
<211> LENGTH: 15
<212> TYPE: PRT
<213> ORGANISM: Artificial Sequence
<220> FEATURE:
<223> OTHER INFORMATION: hinge

<400> SEQUENCE: 262

```
Glu Pro Lys Ser Cys Asp Lys Thr His Thr Cys Pro Ser Cys Pro
1               5                   10                  15
```

<210> SEQ ID NO 263
<211> LENGTH: 13
<212> TYPE: PRT
<213> ORGANISM: Artificial Sequence
<220> FEATURE:
<223> OTHER INFORMATION: hinge

<400> SEQUENCE: 263

```
Glu Ser Lys Tyr Cys Pro Pro Ala Cys Pro Ser Cys Pro
1               5                   10
```

<210> SEQ ID NO 264
<211> LENGTH: 14
<212> TYPE: PRT
<213> ORGANISM: Artificial Sequence
<220> FEATURE:
<223> OTHER INFORMATION: hinge

<400> SEQUENCE: 264

```
Glu Ser Lys Tyr Cys Pro Pro Ala Ala Cys Pro Ser Cys Pro
```

```
1               5                   10
```

```
<210> SEQ ID NO 265
<211> LENGTH: 15
<212> TYPE: PRT
<213> ORGANISM: Artificial Sequence
<220> FEATURE:
<223> OTHER INFORMATION: hinge

<400> SEQUENCE: 265

Glu Ser Lys Tyr Cys Pro Pro Ala Ala Ala Cys Pro Ser Cys Pro
1               5                   10                  15

<210> SEQ ID NO 266
<211> LENGTH: 15
<212> TYPE: PRT
<213> ORGANISM: Artificial Sequence
<220> FEATURE:
<223> OTHER INFORMATION: hinge

<400> SEQUENCE: 266

Glu Ser Lys Tyr Cys Pro Pro Ala Ala Ala Ser Pro Ser Cys Pro
1               5                   10                  15

<210> SEQ ID NO 267
<211> LENGTH: 15
<212> TYPE: PRT
<213> ORGANISM: Artificial Sequence
<220> FEATURE:
<223> OTHER INFORMATION: hinge

<400> SEQUENCE: 267

Glu Ser Lys Tyr Cys Pro Pro Ala Ala Ala Cys Pro Ser Ser Pro
1               5                   10                  15

<210> SEQ ID NO 268
<211> LENGTH: 15
<212> TYPE: PRT
<213> ORGANISM: Artificial Sequence
<220> FEATURE:
<223> OTHER INFORMATION: hinge

<400> SEQUENCE: 268

Glu Ser Lys Cys Gly Pro Pro Ala Ala Ala Cys Pro Ser Cys Pro
1               5                   10                  15

<210> SEQ ID NO 269
<211> LENGTH: 16
<212> TYPE: PRT
<213> ORGANISM: Artificial Sequence
<220> FEATURE:
<223> OTHER INFORMATION: hinge

<400> SEQUENCE: 269

Glu Ser Lys Tyr Cys Pro Pro Ala Ala Ala Ala Cys Pro Ser Cys Pro
1               5                   10                  15

<210> SEQ ID NO 270
<211> LENGTH: 17
<212> TYPE: PRT
<213> ORGANISM: Artificial Sequence
<220> FEATURE:
<223> OTHER INFORMATION: hinge

<400> SEQUENCE: 270

Glu Ser Lys Tyr Cys Pro Pro Ala Ala Ala Ala Ala Cys Pro Ser Cys
1               5                   10                  15
```

Pro

<210> SEQ ID NO 271
<211> LENGTH: 15
<212> TYPE: PRT
<213> ORGANISM: Artificial Sequence
<220> FEATURE:
<223> OTHER INFORMATION: hinge

<400> SEQUENCE: 271

Glu Ser Lys Tyr Cys Pro Pro Gly Gly Gly Cys Pro Ser Cys Pro
1               5                   10                  15

<210> SEQ ID NO 272
<211> LENGTH: 15
<212> TYPE: PRT
<213> ORGANISM: Artificial Sequence
<220> FEATURE:
<223> OTHER INFORMATION: hinge

<400> SEQUENCE: 272

Glu Ser Lys Tyr Cys Pro Pro Ser Ser Ser Cys Pro Ser Cys Pro
1               5                   10                  15

<210> SEQ ID NO 273
<211> LENGTH: 13
<212> TYPE: PRT
<213> ORGANISM: Artificial Sequence
<220> FEATURE:
<223> OTHER INFORMATION: hinge

<400> SEQUENCE: 273

Glu Ser Lys Tyr Cys Pro Pro Thr Cys Pro Ser Cys Pro
1               5                   10

<210> SEQ ID NO 274
<211> LENGTH: 14
<212> TYPE: PRT
<213> ORGANISM: Artificial Sequence
<220> FEATURE:
<223> OTHER INFORMATION: hinge

<400> SEQUENCE: 274

Glu Ser Lys Tyr Cys Pro Pro Thr His Cys Pro Ser Cys Pro
1               5                   10

<210> SEQ ID NO 275
<211> LENGTH: 15
<212> TYPE: PRT
<213> ORGANISM: Artificial Sequence
<220> FEATURE:
<223> OTHER INFORMATION: hinge

<400> SEQUENCE: 275

Glu Ser Lys Tyr Cys Pro Pro Thr His Thr Cys Pro Ser Cys Pro
1               5                   10                  15

<210> SEQ ID NO 276
<211> LENGTH: 15
<212> TYPE: PRT
<213> ORGANISM: Artificial Sequence
<220> FEATURE:
<223> OTHER INFORMATION: hinge

<400> SEQUENCE: 276

Glu Ser Lys Tyr Cys Pro Lys Thr His Thr Cys Pro Ser Cys Pro

```
<210> SEQ ID NO 277
<211> LENGTH: 15
<212> TYPE: PRT
<213> ORGANISM: Artificial Sequence
<220> FEATURE:
<223> OTHER INFORMATION: hinge

<400> SEQUENCE: 277

Glu Ser Lys Tyr Cys Asp Lys Thr His Thr Cys Pro Ser Cys Pro
1               5                   10                  15

<210> SEQ ID NO 278
<211> LENGTH: 14
<212> TYPE: PRT
<213> ORGANISM: Artificial Sequence
<220> FEATURE:
<223> OTHER INFORMATION: hinge

<400> SEQUENCE: 278

Glu Ser Lys Tyr Cys Asp Lys Thr His Cys Pro Ser Cys Pro
1               5                   10

<210> SEQ ID NO 279
<211> LENGTH: 13
<212> TYPE: PRT
<213> ORGANISM: Artificial Sequence
<220> FEATURE:
<223> OTHER INFORMATION: hinge

<400> SEQUENCE: 279

Glu Ser Lys Tyr Cys Asp Lys Thr Cys Pro Ser Cys Pro
1               5                   10

<210> SEQ ID NO 280
<211> LENGTH: 15
<212> TYPE: PRT
<213> ORGANISM: Artificial Sequence
<220> FEATURE:
<223> OTHER INFORMATION: hinge

<400> SEQUENCE: 280

Glu Ser Lys Tyr Cys Asp Lys Ala Ala Ala Cys Pro Ser Cys Pro
1               5                   10                  15

<210> SEQ ID NO 281
<211> LENGTH: 12
<212> TYPE: PRT
<213> ORGANISM: Artificial Sequence
<220> FEATURE:
<223> OTHER INFORMATION: hinge

<400> SEQUENCE: 281

Glu Ser Lys Tyr Cys Asp Lys Cys Pro Ser Cys Pro
1               5                   10

<210> SEQ ID NO 282
<211> LENGTH: 15
<212> TYPE: PRT
<213> ORGANISM: Artificial Sequence
<220> FEATURE:
<223> OTHER INFORMATION: hinge

<400> SEQUENCE: 282

Glu Ser Lys Ser Cys Asp Lys Thr His Thr Cys Pro Ser Cys Pro
1               5                   10                  15
```

```
<210> SEQ ID NO 283
<211> LENGTH: 15
<212> TYPE: PRT
<213> ORGANISM: Artificial Sequence
<220> FEATURE:
<223> OTHER INFORMATION: hinge

<400> SEQUENCE: 283

Glu Pro Lys Tyr Cys Asp Lys Thr His Thr Cys Pro Ser Cys Pro
1               5                   10                  15

<210> SEQ ID NO 284
<211> LENGTH: 12
<212> TYPE: PRT
<213> ORGANISM: Artificial Sequence
<220> FEATURE:
<223> OTHER INFORMATION: hinge

<400> SEQUENCE: 284

Glu Pro Lys Ser Cys Pro Pro Cys Pro Ser Cys Pro
1               5                   10

<210> SEQ ID NO 285
<211> LENGTH: 12
<212> TYPE: PRT
<213> ORGANISM: Artificial Sequence
<220> FEATURE:
<223> OTHER INFORMATION: hinge

<400> SEQUENCE: 285

Glu Ser Lys Ser Cys Pro Pro Cys Pro Ser Cys Pro
1               5                   10

<210> SEQ ID NO 286
<211> LENGTH: 12
<212> TYPE: PRT
<213> ORGANISM: Artificial Sequence
<220> FEATURE:
<223> OTHER INFORMATION: hinge

<400> SEQUENCE: 286

Glu Pro Lys Tyr Cys Pro Pro Cys Pro Ser Cys Pro
1               5                   10

<210> SEQ ID NO 287
<211> LENGTH: 12
<212> TYPE: PRT
<213> ORGANISM: Artificial Sequence
<220> FEATURE:
<223> OTHER INFORMATION: hinge

<400> SEQUENCE: 287

Glu Cys Lys Tyr Gly Pro Pro Cys Pro Ser Cys Pro
1               5                   10

<210> SEQ ID NO 288
<211> LENGTH: 12
<212> TYPE: PRT
<213> ORGANISM: Artificial Sequence
<220> FEATURE:
<223> OTHER INFORMATION: hinge

<400> SEQUENCE: 288

Glu Cys Lys Tyr Gly Pro Pro Ser Pro Ser Cys Pro
1               5                   10
```

<210> SEQ ID NO 289
<211> LENGTH: 12
<212> TYPE: PRT
<213> ORGANISM: Artificial Sequence
<220> FEATURE:
<223> OTHER INFORMATION: hinge

<400> SEQUENCE: 289

Glu Cys Lys Tyr Gly Pro Pro Cys Pro Ser Ser Pro
1               5                   10

<210> SEQ ID NO 290
<211> LENGTH: 12
<212> TYPE: PRT
<213> ORGANISM: Artificial Sequence
<220> FEATURE:
<223> OTHER INFORMATION: hinge

<400> SEQUENCE: 290

Glu Ser Cys Tyr Gly Pro Pro Cys Pro Ser Cys Pro
1               5                   10

<210> SEQ ID NO 291
<211> LENGTH: 12
<212> TYPE: PRT
<213> ORGANISM: Artificial Sequence
<220> FEATURE:
<223> OTHER INFORMATION: hinge

<400> SEQUENCE: 291

Glu Ser Cys Tyr Gly Pro Pro Ser Pro Ser Cys Pro
1               5                   10

<210> SEQ ID NO 292
<211> LENGTH: 12
<212> TYPE: PRT
<213> ORGANISM: Artificial Sequence
<220> FEATURE:
<223> OTHER INFORMATION: hinge

<400> SEQUENCE: 292

Glu Ser Cys Tyr Gly Pro Pro Cys Pro Ser Ser Pro
1               5                   10

<210> SEQ ID NO 293
<211> LENGTH: 12
<212> TYPE: PRT
<213> ORGANISM: Artificial Sequence
<220> FEATURE:
<223> OTHER INFORMATION: hinge

<400> SEQUENCE: 293

Glu Ser Lys Cys Gly Pro Pro Cys Pro Ser Cys Pro
1               5                   10

<210> SEQ ID NO 294
<211> LENGTH: 12
<212> TYPE: PRT
<213> ORGANISM: Artificial Sequence
<220> FEATURE:
<223> OTHER INFORMATION: hinge

<400> SEQUENCE: 294

Glu Ser Lys Cys Gly Pro Pro Ser Pro Ser Cys Pro
1               5                   10

```
<210> SEQ ID NO 295
<211> LENGTH: 12
<212> TYPE: PRT
<213> ORGANISM: Artificial Sequence
<220> FEATURE:
<223> OTHER INFORMATION: hinge

<400> SEQUENCE: 295

Glu Ser Lys Cys Gly Pro Pro Cys Pro Ser Ser Pro
1               5                   10

<210> SEQ ID NO 296
<211> LENGTH: 118
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 1
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 296

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Gly Pro Pro Cys Pro Ser Cys Pro Ala Pro
            100                 105                 110

Glu Phe Leu Gly Gly Pro
        115

<210> SEQ ID NO 297
<211> LENGTH: 118
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 4
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 297

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Gly Pro Pro Ser Pro Ser Ser Pro Ala Pro
                100                 105                 110

Glu Phe Leu Gly Gly Pro
            115

<210> SEQ ID NO 298
<211> LENGTH: 118
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 5
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 298

Xaa Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Cys Pro Pro Cys Pro Ser Cys Pro Ala Pro
                100                 105                 110

Glu Phe Leu Gly Gly Pro
            115

<210> SEQ ID NO 299
<211> LENGTH: 118
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 5P
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E
```

<400> SEQUENCE: 299

Xaa Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Cys Pro Pro Cys Pro Pro Cys Pro Ala Pro
            100                 105                 110

Glu Phe Leu Gly Gly Pro
        115

<210> SEQ ID NO 300
<211> LENGTH: 118
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 9
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 300

Xaa Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Cys Pro Pro Ser Pro Ser Cys Pro Ala Pro
            100                 105                 110

Glu Phe Leu Gly Gly Pro
        115

<210> SEQ ID NO 301
<211> LENGTH: 118
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 10
<220> FEATURE:
<221> NAME/KEY: MISC_FEATURE

```
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 301

Xaa Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Cys Pro Pro Cys Pro Ser Ser Pro Ala Pro
            100                 105                 110

Glu Phe Leu Gly Gly Pro
            115

<210> SEQ ID NO 302
<211> LENGTH: 118
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 11
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 302

Xaa Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Cys Pro Pro Ser Pro Ser Ser Pro Ala Pro
            100                 105                 110

Glu Phe Leu Gly Gly Pro
            115

<210> SEQ ID NO 303
<211> LENGTH: 118
```

-continued

```
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 12
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 303

Xaa Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Gly Pro Pro Ser Pro Ser Cys Pro Ala Pro
            100                 105                 110

Glu Phe Leu Gly Gly Pro
            115

<210> SEQ ID NO 304
<211> LENGTH: 118
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 13
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 304

Xaa Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Gly Pro Pro Cys Pro Ser Pro Ala Pro
            100                 105                 110
```

Glu Phe Leu Gly Gly Pro
        115

<210> SEQ ID NO 305
<211> LENGTH: 118
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 14
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 305

Xaa Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Gly Pro Pro Ser Pro Ser Pro Ala Pro
            100                 105                 110

Glu Phe Leu Gly Gly Pro
        115

<210> SEQ ID NO 306
<211> LENGTH: 327
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 1
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 306

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Lys Thr

```
                65                   70                   75                   80
Tyr Thr Cys Asn Val Asp His Lys Pro Ser Asn Thr Lys Val Asp Lys
                    85                   90                   95

Arg Val Xaa Ser Lys Tyr Gly Pro Pro Cys Pro Ser Cys Pro Ala Pro
                100                 105                  110

Glu Phe Leu Gly Gly Pro Ser Val Phe Leu Phe Pro Pro Lys Pro Lys
                115                  120                 125

Asp Thr Leu Met Ile Ser Arg Thr Pro Glu Val Thr Cys Val Val Val
130                  135                 140

Asp Val Ser Gln Glu Asp Pro Glu Val Gln Phe Asn Trp Tyr Val Asp
145                  150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
                210                 215                 220

Glu Pro Gln Val Tyr Thr Leu Pro Pro Ser Gln Glu Glu Met Thr Lys
225                 230                  235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
                290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 307
<211> LENGTH: 327
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 4
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 307

Xaa Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
```

```
            50                  55                  60
Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Xaa Ser Lys Tyr Gly Pro Pro Ser Pro Ser Ser Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 308
<211> LENGTH: 327
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 5
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 308

Xaa Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
```

```
                    35                  40                  45
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Xaa Ser Lys Tyr Cys Pro Pro Cys Pro Ser Cys Pro Ala Pro
                100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 309
<211> LENGTH: 327
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 5P
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 309

Xaa Ser Thr Lys Gly Pro Ser Val Phe Pro Leu Ala Pro Cys Ser Arg
 1                   5                  10                  15

Ser Thr Ser Glu Ser Thr Ala Ala Leu Gly Cys Leu Val Lys Asp Tyr
```

```
            20                  25                  30
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Cys Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 310
<211> LENGTH: 327
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 9
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 310

Xaa Ser Thr Lys Gly Pro Ser Val Phe Pro Leu Ala Pro Cys Ser Arg
```

```
            1               5                  10                 15
        Ser Thr Ser Glu Ser Thr Ala Ala Leu Gly Cys Leu Val Lys Asp Tyr
                        20                  25                  30

Phe Pro Glu Pro Val Thr Val Ser Trp Asn Ser Gly Ala Leu Thr Ser
                        35                  40                  45

Gly Val His Thr Phe Pro Ala Val Leu Gln Ser Ser Gly Leu Tyr Ser
                        50                  55                  60

Leu Ser Ser Val Val Thr Val Pro Ser Ser Leu Gly Thr Lys Thr
        65                      70                  75                  80

Tyr Thr Cys Asn Val Asp His Lys Pro Ser Asn Thr Lys Val Asp Lys
                        85                  90                  95

Arg Val Xaa Ser Lys Tyr Cys Pro Pro Ser Pro Ser Cys Pro Ala Pro
                        100                 105                 110

Glu Phe Leu Gly Gly Pro Ser Val Phe Leu Phe Pro Pro Lys Pro Lys
                        115                 120                 125

Asp Thr Leu Met Ile Ser Arg Thr Pro Glu Val Thr Cys Val Val Val
                        130                 135                 140

Asp Val Ser Gln Glu Asp Pro Glu Val Gln Phe Asn Trp Tyr Val Asp
        145                     150                 155                 160

Gly Val Glu Val His Asn Ala Lys Thr Lys Pro Arg Glu Glu Gln Phe
                        165                 170                 175

Asn Ser Thr Tyr Arg Val Val Ser Val Leu Thr Val Leu His Gln Asp
                        180                 185                 190

Trp Leu Asn Gly Lys Glu Tyr Lys Cys Lys Val Ser Asn Lys Gly Leu
                        195                 200                 205

Pro Ser Ser Ile Glu Lys Thr Ile Ser Lys Ala Lys Gly Gln Pro Arg
                        210                 215                 220

Glu Pro Gln Val Tyr Thr Leu Pro Pro Ser Gln Glu Glu Met Thr Lys
        225                     230                 235                 240

Asn Gln Val Ser Leu Thr Cys Leu Val Lys Gly Phe Tyr Pro Ser Asp
                        245                 250                 255

Ile Ala Val Glu Trp Glu Ser Asn Gly Gln Pro Glu Asn Asn Tyr Lys
                        260                 265                 270

Thr Thr Pro Pro Val Leu Asp Ser Asp Gly Ser Phe Phe Leu Tyr Ser
                        275                 280                 285

Arg Leu Thr Val Asp Lys Ser Arg Trp Gln Glu Gly Asn Val Phe Ser
                        290                 295                 300

Cys Ser Val Met His Glu Ala Leu His Asn His Tyr Thr Gln Lys Ser
        305                     310                 315                 320

Leu Ser Leu Ser Leu Gly Lys
                        325

<210> SEQ ID NO 311
<211> LENGTH: 327
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 10
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E
```

-continued

<400> SEQUENCE: 311

```
Xaa Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Cys Pro Pro Cys Pro Ser Ser Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 312
<211> LENGTH: 327
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 11
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 312

```
Xaa Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Cys Pro Pro Ser Pro Ser Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 313
<211> LENGTH: 327
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 12
<220> FEATURE:
<221> NAME/KEY: MISC_FEATURE
<222> LOCATION: (1)..(1)

<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 313

Xaa Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Gly Pro Pro Ser Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 314
<211> LENGTH: 327
<212> TYPE: PRT
<213> ORGANISM: Artificial Sequence
<220> FEATURE:
<223> OTHER INFORMATION: CH1 domain, hinge region, CH2 domain and CH3
      domain sequences of antibodies 13

```
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 314
```

| | | | | | | | | | | | | | | | |
|---|---|---|---|---|---|---|---|---|---|---|---|---|---|---|---|
| Xaa | Ser | Thr | Lys | Gly | Pro | Ser | Val | Phe | Pro | Leu | Ala | Pro | Cys | Ser | Arg |
| 1 | | | | 5 | | | | | 10 | | | | | 15 | |
| Ser | Thr | Ser | Glu | Ser | Thr | Ala | Ala | Leu | Gly | Cys | Leu | Val | Lys | Asp | Tyr |
| | | | 20 | | | | | 25 | | | | | 30 | | |
| Phe | Pro | Glu | Pro | Val | Thr | Val | Ser | Trp | Asn | Ser | Gly | Ala | Leu | Thr | Ser |
| | | 35 | | | | | 40 | | | | | 45 | | | |
| Gly | Val | His | Thr | Phe | Pro | Ala | Val | Leu | Gln | Ser | Ser | Gly | Leu | Tyr | Ser |
| | 50 | | | | | 55 | | | | | 60 | | | | |
| Leu | Ser | Ser | Val | Val | Thr | Val | Pro | Ser | Ser | Ser | Leu | Gly | Thr | Lys | Thr |
| 65 | | | | | 70 | | | | | 75 | | | | | 80 |
| Tyr | Thr | Cys | Asn | Val | Asp | His | Lys | Pro | Ser | Asn | Thr | Lys | Val | Asp | Lys |
| | | | | 85 | | | | | 90 | | | | | 95 | |
| Arg | Val | Xaa | Ser | Lys | Tyr | Gly | Pro | Pro | Cys | Pro | Ser | Ser | Pro | Ala | Pro |
| | | | 100 | | | | | 105 | | | | | 110 | | |
| Glu | Phe | Leu | Gly | Gly | Pro | Ser | Val | Phe | Leu | Phe | Pro | Pro | Lys | Pro | Lys |
| | | | 115 | | | | | 120 | | | | | 125 | | |
| Asp | Thr | Leu | Met | Ile | Ser | Arg | Thr | Pro | Glu | Val | Thr | Cys | Val | Val | Val |
| | | 130 | | | | | 135 | | | | | 140 | | | |
| Asp | Val | Ser | Gln | Glu | Asp | Pro | Glu | Val | Gln | Phe | Asn | Trp | Tyr | Val | Asp |
| 145 | | | | | 150 | | | | | 155 | | | | | 160 |
| Gly | Val | Glu | Val | His | Asn | Ala | Lys | Thr | Lys | Pro | Arg | Glu | Glu | Gln | Phe |
| | | | | 165 | | | | | 170 | | | | | 175 | |
| Asn | Ser | Thr | Tyr | Arg | Val | Val | Ser | Val | Leu | Thr | Val | Leu | His | Gln | Asp |
| | | | 180 | | | | | 185 | | | | | 190 | | |
| Trp | Leu | Asn | Gly | Lys | Glu | Tyr | Lys | Cys | Lys | Val | Ser | Asn | Lys | Gly | Leu |
| | | | 195 | | | | | 200 | | | | | 205 | | |
| Pro | Ser | Ser | Ile | Glu | Lys | Thr | Ile | Ser | Lys | Ala | Lys | Gly | Gln | Pro | Arg |
| | | 210 | | | | | 215 | | | | | 220 | | | |
| Glu | Pro | Gln | Val | Tyr | Thr | Leu | Pro | Pro | Ser | Gln | Glu | Glu | Met | Thr | Lys |
| 225 | | | | | 230 | | | | | 235 | | | | | 240 |
| Asn | Gln | Val | Ser | Leu | Thr | Cys | Leu | Val | Lys | Gly | Phe | Tyr | Pro | Ser | Asp |
| | | | | 245 | | | | | 250 | | | | | 255 | |
| Ile | Ala | Val | Glu | Trp | Glu | Ser | Asn | Gly | Gln | Pro | Glu | Asn | Asn | Tyr | Lys |
| | | | 260 | | | | | 265 | | | | | 270 | | |
| Thr | Thr | Pro | Pro | Val | Leu | Asp | Ser | Asp | Gly | Ser | Phe | Phe | Leu | Tyr | Ser |
| | | 275 | | | | | 280 | | | | | 285 | | | |
| Arg | Leu | Thr | Val | Asp | Lys | Ser | Arg | Trp | Gln | Glu | Gly | Asn | Val | Phe | Ser |
| | | 290 | | | | | 295 | | | | | 300 | | | |
| Cys | Ser | Val | Met | His | Glu | Ala | Leu | His | Asn | His | Tyr | Thr | Gln | Lys | Ser |
| 305 | | | | | 310 | | | | | 315 | | | | | 320 |
| Leu | Ser | Leu | Ser | Leu | Gly | Lys | | | | | | | | | |
| | | | | 325 | | | | | | | | | | | |

```
<210> SEQ ID NO 315
<211> LENGTH: 327
<212> TYPE: PRT
<213> ORGANISM: Artificial Sequence
```

<220> FEATURE:
<223> OTHER INFORMATION: CH1 domain, hinge region, CH2 domain and CH3 domain sequences of antibodies 14
<220> FEATURE:
<221> NAME/KEY: MISC_FEATURE
<222> LOCATION: (1)..(1)
<223> OTHER INFORMATION: Xaa is absent or A
<220> FEATURE:
<221> NAME/KEY: MISC_FEATURE
<222> LOCATION: (99)..(99)
<223> OTHER INFORMATION: Xaa is absent or E

<400> SEQUENCE: 315

```
Xaa Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Xaa Ser Lys Tyr Gly Pro Pro Ser Pro Ser Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 316

```
<211> LENGTH: 15
<212> TYPE: PRT
<213> ORGANISM: Artificial Sequence
<220> FEATURE:
<223> OTHER INFORMATION: wild-type IgG1 upper and core hinge

<400> SEQUENCE: 316

Glu Pro Lys Ser Cys Asp Lys Thr His Thr Cys Pro Pro Cys Pro
1               5                   10                  15

<210> SEQ ID NO 317
<211> LENGTH: 12
<212> TYPE: PRT
<213> ORGANISM: Artificial Sequence
<220> FEATURE:
<223> OTHER INFORMATION: wild-type IgG4 upper and core hinge

<400> SEQUENCE: 317

Glu Ser Lys Tyr Gly Pro Pro Cys Pro Ser Cys Pro
1               5                   10

<210> SEQ ID NO 318
<211> LENGTH: 7
<212> TYPE: PRT
<213> ORGANISM: Artificial Sequence
<220> FEATURE:
<223> OTHER INFORMATION: hinge

<400> SEQUENCE: 318

Glu Pro Lys Tyr Gly Pro Pro
1               5

<210> SEQ ID NO 319
<211> LENGTH: 10
<212> TYPE: PRT
<213> ORGANISM: Artificial Sequence
<220> FEATURE:
<223> OTHER INFORMATION: IgG1 upper hinge

<400> SEQUENCE: 319

Glu Pro Lys Ser Cys Asp Lys Thr His Thr
1               5                   10

<210> SEQ ID NO 320
<211> LENGTH: 15
<212> TYPE: PRT
<213> ORGANISM: Artificial Sequence
<220> FEATURE:
<223> OTHER INFORMATION: hinge

<400> SEQUENCE: 320

Glu Pro Lys Ser Cys Asp Lys Thr His Thr Cys Pro Pro Cys Pro
1               5                   10                  15

<210> SEQ ID NO 321
<211> LENGTH: 8
<212> TYPE: PRT
<213> ORGANISM: Artificial Sequence
<220> FEATURE:
<223> OTHER INFORMATION: IgG4 lower hinge

<400> SEQUENCE: 321

Ala Pro Glu Phe Leu Gly Gly Pro
1               5

<210> SEQ ID NO 322
<211> LENGTH: 5
```

```
<212> TYPE: PRT
<213> ORGANISM: Artificial Sequence
<220> FEATURE:
<223> OTHER INFORMATION: hinge

<400> SEQUENCE: 322

Cys Pro Pro Cys Pro
1               5
```